(12) United States Patent
Weterings et al.

(10) Patent No.: US 10,196,664 B2
(45) Date of Patent: Feb. 5, 2019

(54) ***NICOTIANA BENTHAMIANA* PLANTS DEFICIENT IN FUCOSYLTRANSFERASE ACTIVITY**

(71) Applicant: ICON GENETICS GMBH, Halle (Saale) (DE)

(72) Inventors: Koen Weterings, Raleigh, NC (US); Gerben Van Eldik, Zwijnaarde (BE)

(73) Assignee: Icon Genetics GmbH, Halle (Saale) (DE)

( * ) Notice: Subject to any disclaimer, the term of this patent is extended or adjusted under 35 U.S.C. 154(b) by 654 days.

(21) Appl. No.: 14/347,752

(22) PCT Filed: Oct. 4, 2012

(86) PCT No.: PCT/EP2012/004160
§ 371 (c)(1),
(2) Date: Mar. 27, 2014

(87) PCT Pub. No.: WO2013/050155
PCT Pub. Date: Apr. 11, 2013

(65) Prior Publication Data
US 2015/0080553 A1   Mar. 19, 2015

Related U.S. Application Data

(60) Provisional application No. 61/542,965, filed on Oct. 4, 2011.

(30) Foreign Application Priority Data

Oct. 6, 2011 (EP) .................................. 11075218

(51) Int. Cl.
| | | |
|---|---|---|
| *C12P 21/00* | (2006.01) | |
| *C12N 9/10* | (2006.01) | |
| *C12N 15/82* | (2006.01) | |
| *C12N 15/113* | (2010.01) | |
| *C07K 16/00* | (2006.01) | |

(52) U.S. Cl.
CPC ............ *C12P 21/005* (2013.01); *C07K 16/00* (2013.01); *C12N 9/1051* (2013.01); *C12N 15/8245* (2013.01); *C12N 15/8246* (2013.01); *C12N 15/8257* (2013.01); *C12Y 204/01214* (2013.01)

(58) Field of Classification Search
None
See application file for complete search history.

(56) References Cited

U.S. PATENT DOCUMENTS

| | | | | |
|---|---|---|---|---|
| 2005/0223430 A1* | 10/2005 | Bakker | ................ | C12N 9/1051 800/288 |
| 2010/0154081 A1* | 6/2010 | Weterings | .......... | C12N 15/8257 800/298 |
| 2010/0242128 A1* | 9/2010 | Steinkellner | ......... | C12N 9/1051 800/260 |

FOREIGN PATENT DOCUMENTS

| | | | |
|---|---|---|---|
| WO | WO 2008/141806 A1 | 11/2008 | |
| WO | WO 2009/056155 A1 | 5/2009 | |
| WO | WO 2010/145846 A1 | 12/2010 | |
| WO | 2011/117249 A1 * | 9/2011 | ............... C12N 9/10 |

OTHER PUBLICATIONS

Strasser et al (Plant Biotechnology J., 2008, 6(4): 392-402).*
GenEmbl AB498916, published Jun. 2, 2010; alignment appended to Non-Final Rejection.*
Matsuo et al (Plant Biotechnology J., 2011, 9(2): 264-281; published online Aug. 19, 2010).*
Goodin et al (MPMI, 2008, 21(8): 1015-1026).*
GenBank EF562630.1, published Jan. 2008; alignment appended to Non-Final Rejection.*
Zhai et al (Plant Physiol., 2009, 149(2): 642-652).*
Kang, J., et al., "Salt tolerance of *Arabidopsis thaliana* requires maturation of N-glycosylated proteins in the Golgi apparatus," *PNAS*, 2008, vol. 105(15), pp. 5933-5938.

* cited by examiner

*Primary Examiner* — Stephen Uyeno
(74) *Attorney, Agent, or Firm* — David M. Saravitz; Williams Mullen, P.C.

(57) ABSTRACT

The invention provides methods for reducing the levels of alfa (1,3)-fucosylated N-glycans on glycoproteins produced in plants or plant cells. In addition, the invention provides alfa(1,3)-fucosyltransferase genes from *Nicotiana benthamiana*, and mutant *N. benthamiana* plants in which the levels of alfa(1,3)-fucosylated N-glycans are reduced.

8 Claims, 19 Drawing Sheets
Specification includes a Sequence Listing.

| generation | selected genotypes | crosses |
|---|---|---|
| 1 | x14/x14 x19/x19 | x14/x14 x19/x19 ✕ a/a |
|  | a/a | b/b ✕ c/c |
|  | b/b | c/c ✕ d/d |
|  | c/c | d/d ✕ e/e |
|  | d/d | a/a ✕ b/b |
|  | e/e |  |
| 2 | selected genotypes | crosses |
|  | X14/x14 X19/x19 A/a | X14/x14 X19/x19 A/a ✕ B/b C/c |
|  | B/b C/c | X14/x14 X19/x19 A/a ✕ C/c D/d |
|  | C/c D/d | X14/x14 X19/x19 A/a ✕ D/d E/e |
|  | D/d E/e | X14/x14 X19/x19 A/a ✕ A/a B/b |
| 3 | selected genotypes | crosses |
|  | X14/x14 X19/x19 A/a B/b C/c | X14/x14 X19/x19 A/a B/b C/c ✕ X14/x14 X19/x19 A/a D/d E/e |
|  | X14/x14 X19/x19 A/a C/c D/d | X14/x14 X19/x19 A/a C/c D/d ✕ X14/x14 X19/x19 A/a C/c D/d |
|  | X14/x14 X19/x19 A/a D/d E/e |  |
| 4 | selected genotypes | crosses |
|  | x14/x14 X19/x19 a/a c/c d/d |  |
|  | x14/x14 x19/x19 a/a B/b C/c D/d E/e | x14/x14 x19/x19 a/a B/b C/c D/d E/e ✕ x14/x14 x19/x19 a/a B/b C/c D/d E/e |
| 5 | selected genotypes |  |
|  | x14/x14 x19/x19 a/a b/b c/c d/d e/e |  |

Fig. 4

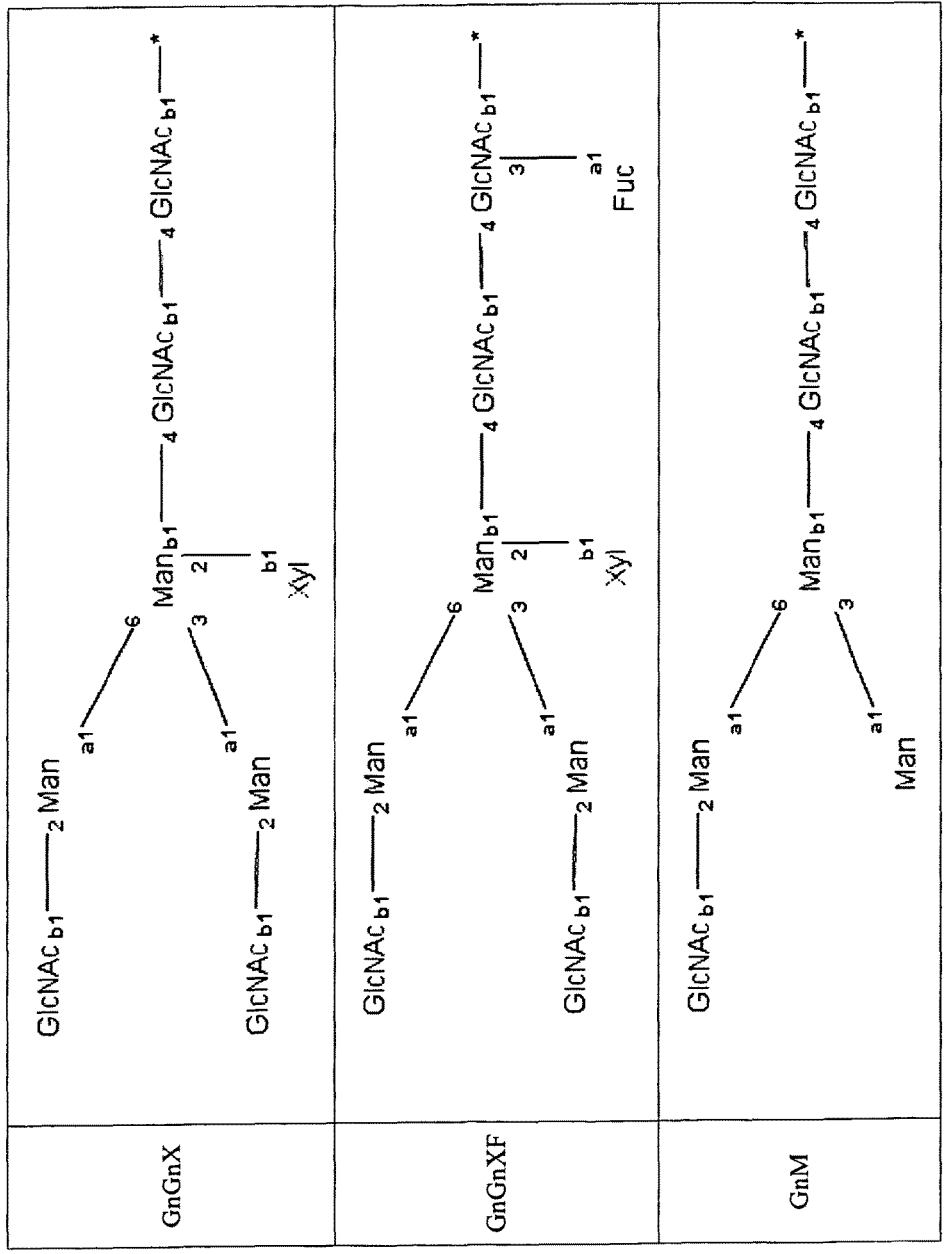
Fig. 10, continued

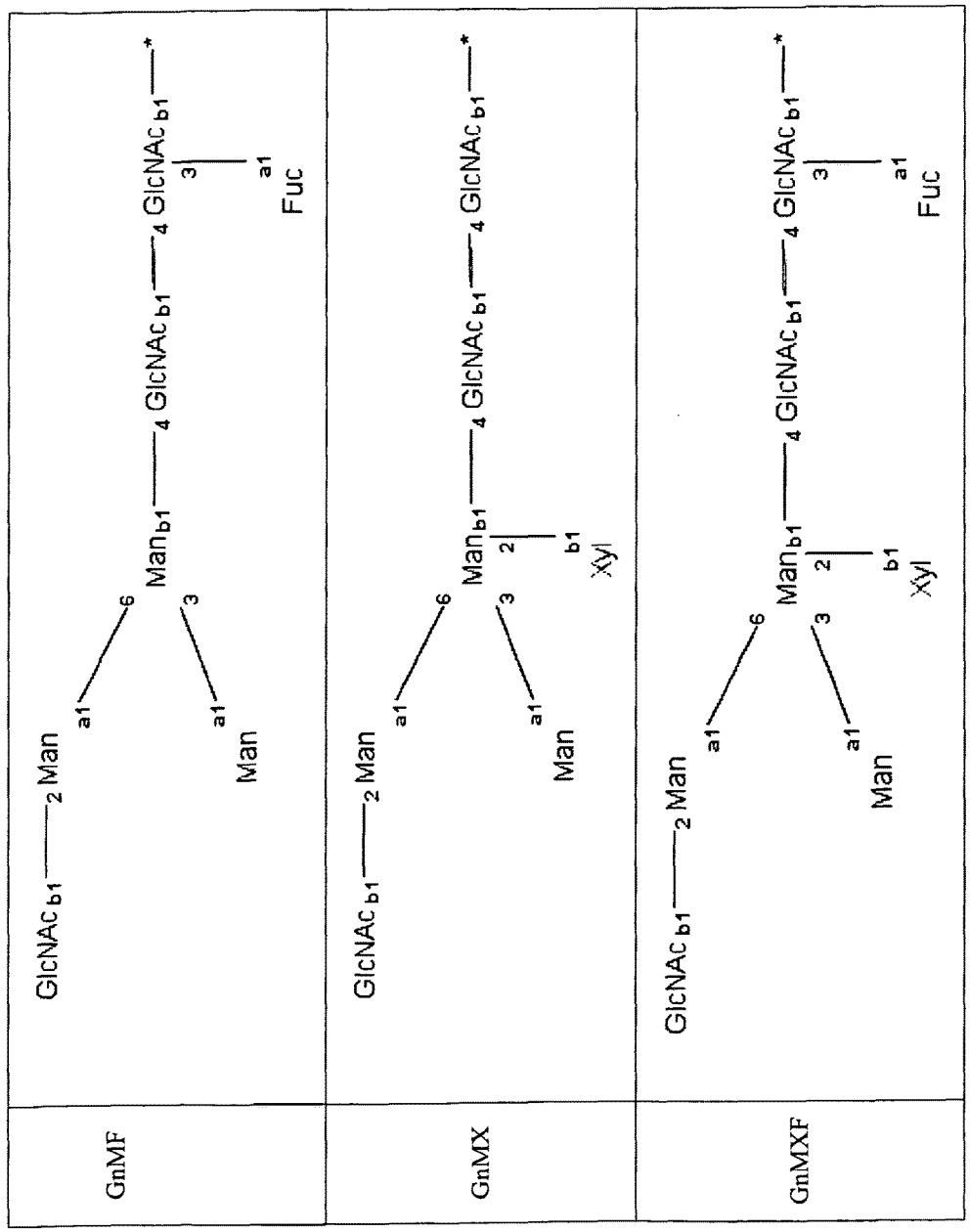
Fig. 10, continued

| | |
|---|---|
| GnU | GlcNAc b1—2 Man a1,6 Man b1—4 GlcNAc b1—4 GlcNAc b1—* |
| GnUX | GlcNAc b1—2 Man a1,6 Man b1(2, b1 Xyl)—4 GlcNAc b1—4 GlcNAc b1—* |
| GnUXF | GlcNAc b1—2 Man a1,6 Man b1(2, b1 Xyl)—4 GlcNAc b1(3, a1 Fuc)—4 GlcNAc b1—* |

Fig. 10, continued

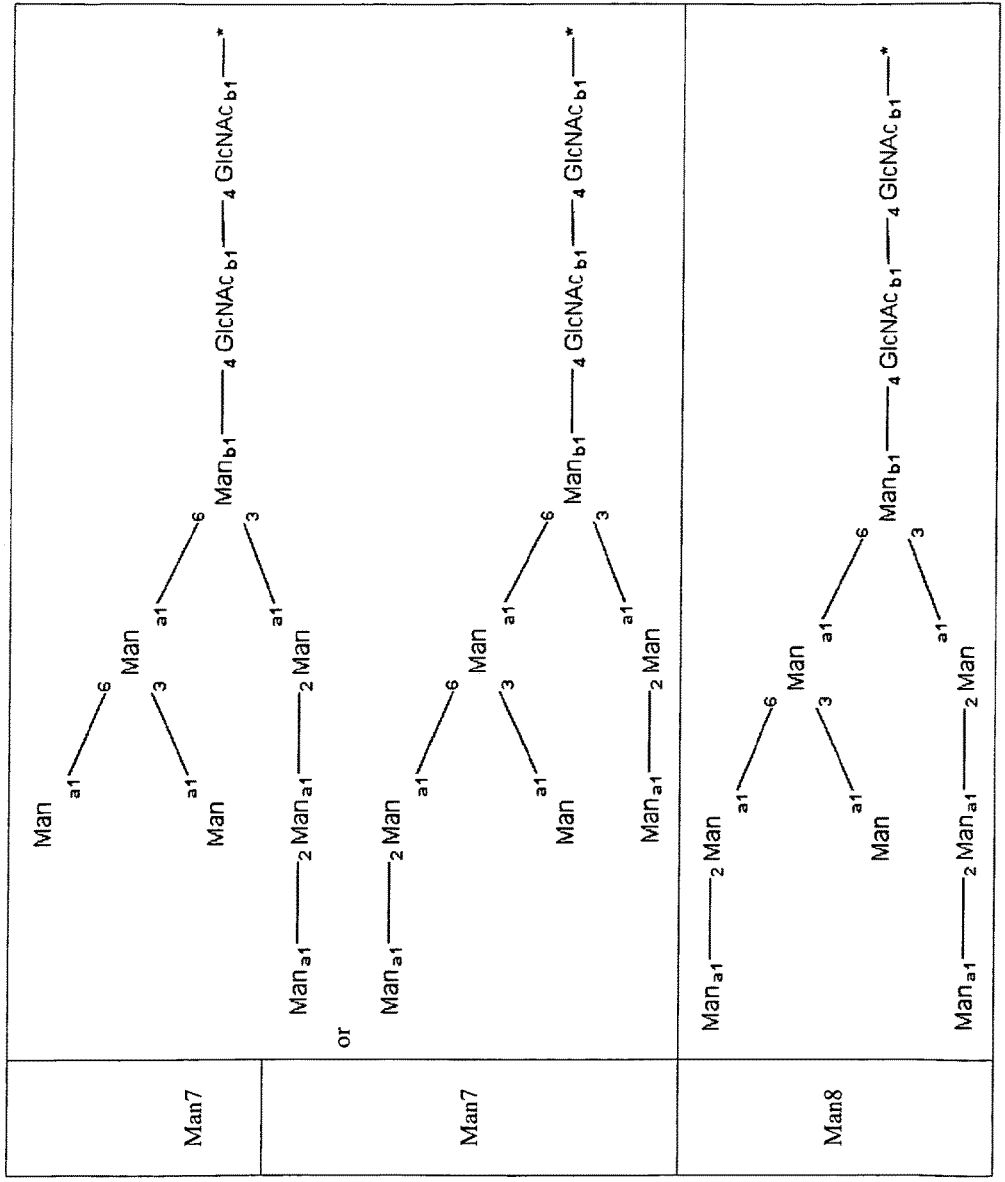
Fig. 10, continued

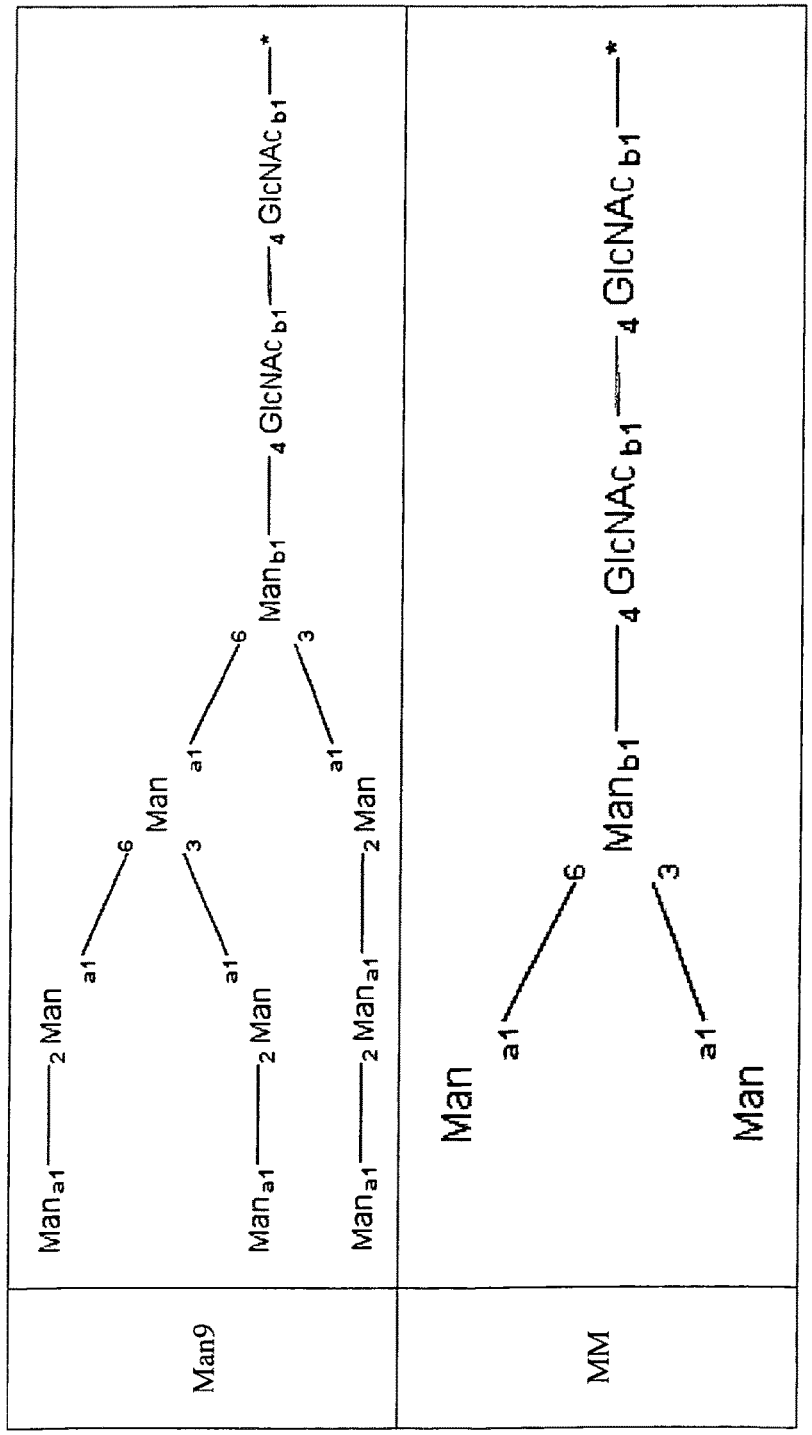
Fig. 10, continued

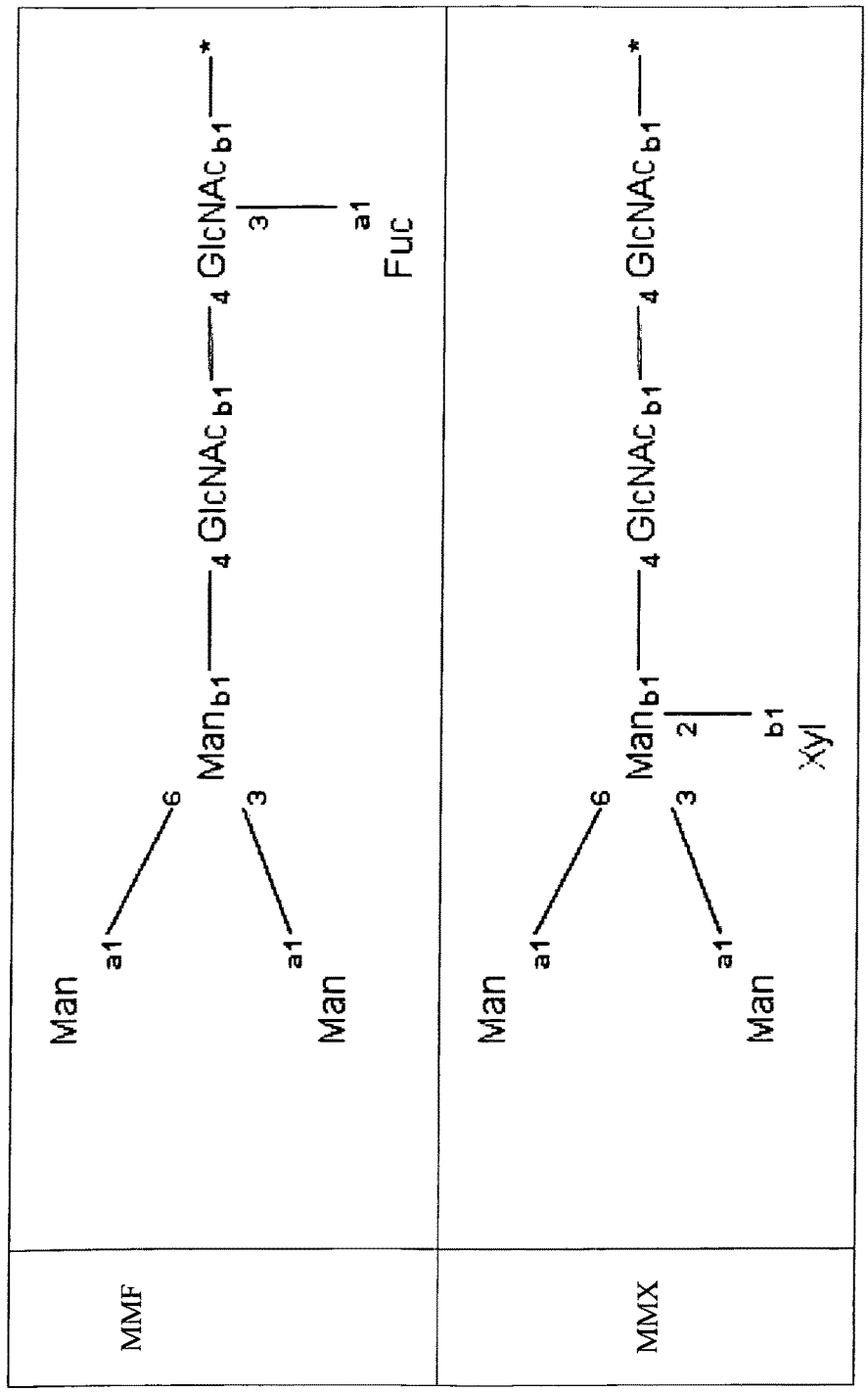
Fig. 10, continued

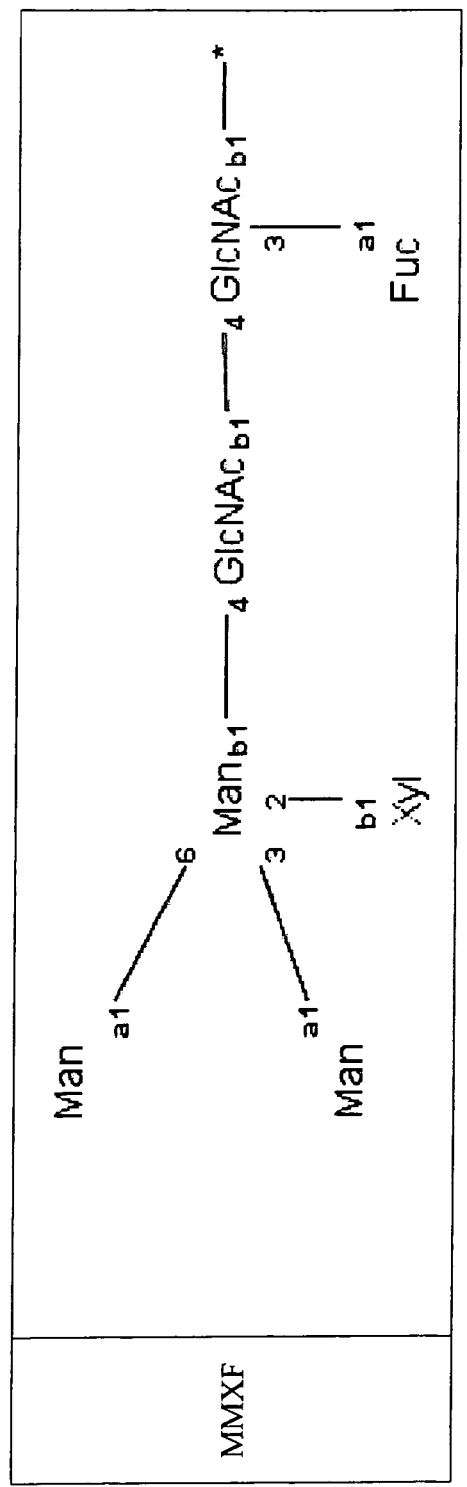
Fig. 10, continued

NICOTIANA BENTHAMIANA PLANTS DEFICIENT IN FUCOSYLTRANSFERASE ACTIVITY

CROSS-REFERENCE TO RELATED APPLICATIONS

This application is the U.S. National Stage of International Application No. PCT/EP2012/004160, filed Oct. 4, 2012, which designates the U.S. and was published by the International Bureau in English on Apr. 11, 2013, and which claims the benefit of U.S. Provisional Application No. 61/542,965, filed Oct. 4, 2011, and European Application 11075218.5, filed Oct. 6, 2011, the contents of which are hereby incorporated herein in their entirety by reference.

FIELD OF THE INVENTION

The current invention relates to the field of molecular farming, i.e. the use of plants and plant cells as bioreactors to produce peptides and proteins, including biopharmaceuticals, particularly polypeptides and proteins with pharmaceutical interest such as therapeutic proteins, which have an altered N-glycosylation pattern resulting in a lower level of immunogenic protein-bound N-glycans, particularly a lower level of beta(1,2)-xylose residues and core alfa(1,3)-fucose residues on the protein-bound N-glycans, than counterpart unmodified plants. The invention relates to plants of the genus *Nicotiana* which are deficient in alfa(1,3)-fucosyltransferase and beta(1,2)-xylosyltransferase activity, which plants may be applied as host plants or host cells to produce heterologous glycoproteins.

BACKGROUND

Glycosylation is the covalent linkage of an oligosaccharide chain to a protein resulting in a glycoprotein. In many glycoproteins, the oligosaccharide chain is attached to the amide nitrogen of an asparagine (Asn) residue and leads to N-glycosylation. Glycosylation represents the most widespread post-translational modification found in natural and biopharmaceutical proteins. It is estimated that more than half of the human proteins are glycosylated and their function frequently depends on particular glycoforms (glycans), which can affect their plasma half life, tissue targeting or even their biological activity. Similarly, more than one-third of approved biopharmaceuticals are glycoproteins and both their function and efficiency are affected by the presence and composition of their N-glycans.

Leafy crops, such as the tobacco plant *Nicotiana benthamiana*, are an attractive system for the production of therapeutic proteins, as plants are generally considered to have several advantages, including the lack of animal pathogens such as prions and viruses, low cost and the large-scale production of safe and biologically active valuable recombinant proteins, the case of scale-up, efficient harvesting and storage possibilities. However, N-linked glycans from plants differ from those of mammalian cells. In plants, beta(1,2)-xylose and alfa(1,3)-fucose residues have been shown to be linked to the core Man3GlucNAc2-Asn of glycans, whereas they are not detected on mammalian glycans, where sialic acid residues and terminal beta(1,4)-galactosyl structures occur instead. The unique N-glycans added by plants could impact both immunogenicity and functional activity of the protein and, consequently, may represent a limitation for plants to be used as a protein production platform. Indeed, the immunogenicity of beta(1,2)-xylose residues and alfa(1,3)-fucose in mammals has been described (Bardor et al., 2003, Glycobiology 13: 427).

The enzyme that catalyses the transfer of xylose from UDP-xylose to the core β-linked mannose of protein-bound N-glycans is beta(1,2)-xylosyltransferase ("XylT", EC 2.4.2.38). The beta-1,2-xylosyltransferase is an enzyme unique to plants and some non-vertebrate animal species and does not occur in human beings or in other vertebrates. WO2007107296 describes the identification and cloning of beta-1,2-xylosyltransferases from the genus *Nicotiana* such as *Nicotiana benthamiana*.

The enzyme that catalyses the transfer of fucose from GDP-fucose to the core β-linked N-acetyl glucosamine (GlcNAc) of protein-bound N-glycans is alfa(1,3)-fucosyltransferase ("FucT", EC 2.4.1.214). WO2009056155 describes an alfa(1,3)-fucosyltransferase cDNA sequence from *Nicotiana benthamiana*.

Various strategies have been applied to avoid alfa(1,3)-fucosyl and beta(1,2)-xylosyl structures on glycoproteins produced by plants. WO2008141806 describes knock-outs in two alfa(1,3)-fucosyltransferase genes and in one beta(1,2)-xylosyltransferase gene in *Arabidopsis thaliana*. WO2009056155 describes an RNA interference strategy for the generation of *Nicotiana benthamiana* plants which are deficient in the formation of beta-1,2-xylosyl structures as well as devoid of alfa-1,3-fucosyl structures on heterologous glycoproteins. Yin et al. (2011, Protein Cell 2:41) report downregulation of the expression of the endogenous xylosyltranferase and fucosyltransferase in *Nicotiana tabacum* using RNA interference (RNAi) strategy. They found that xylosylated and core fucosylated N-glycans were significantly, but not completely, reduced in the glycoengineered lines. WO2010145846 describes knock-outs of the two beta(1,2)-xylosyltransferase genes in *Nicotiana benthamiana*. The homozygous combination of the four beta(1,2)-xylosyltransferase null alleles proved to be sufficient for the elimination of the complete beta-1,2-xylosyltransferase activity in *Nicotiana benthamiana*.

Knock-out alleles of the alfa(1,3)-fucosyltransferase genes of *Nicotiana benthamiana* have not been described thus far.

The current invention provides methods and means to reduce the levels of core alfa(1,3)-fucose residues on N-glycans on glycoproteins in *Nicotiana benthamiana*, as will become apparent from the following description, examples, drawings and claims provided herein.

SUMMARY OF THE INVENTION

In a first embodiment, the invention provides a method to produce glycoproteins with reduced levels of core alfa(1,3)-fucose residues in *Nicotiana benthamiana*, said method comprising the steps of providing a plant or plant cell comprising at least three knock-out alfa(1,3)-fucosyltransferase genes, and cultivating said cell and isolating glycoproteins from said cell. In another embodiment, said method further comprises a reduction of the level of beta(1,2)-xylosyltransferase activity. In yet another embodiment, said reduction of the level of beta(1,2)-xylosyltransferase activity is the result of a knock-out mutation in endogenous beta(1,2)-fucosyltransferase genes.

In another embodiment of the invention, a method is provided to produce glycoproteins with reduced levels of core alfa(1,3)-fucose residues in *Nicotiana benthamiana*, said method comprising the steps of providing a plant or plant cell comprising at least five knock-out alfa(1,3)-fucosyltransferase genes, and cultivating said cell and isolating glycoproteins from said cell. In a further embodiment, said knock-out alfa(1,3)-fucosyltransferase genes occur in a homozygous state in the genome.

In yet another embodiment, the methods according to the invention are further characterized in that the expression of at least five endogenous alfa(1,3)-fucosyltransferase encoding genes is reduced through transcriptional or post-transcriptional silencing. In a further embodiment, the plant or plant cell according to the invention further comprises at least one chimeric gene comprising the following operably linked DNA fragments: a plant-expressible promoter, a DNA region, which when transcribed yields an RNA molecule inhibitory to at least one alfa(1,3)-fucosyltransferase encoding gene, and a DNA region comprising a transcription termination and polyadenylation signal functional in plants. In yet a further embodiment, said DNA region comprises the sequence of SEQ ID No. 19.

In yet another embodiment of the method of the invention, said glycoprotein is a heterologous protein. In yet a further embodiment, said heterologous glycoprotein is expressed from a chimeric gene comprising the following operably linked nucleic acid molecules: a plant-expressible promoter, a DNA region encoding said heterologous glycoprotein, and a DNA region involved in transcription termination and polyadenylation. In yet another embodiment, the method according to the invention further comprises the step of purification of said heterologous glycoprotein.

In another embodiment of the invention, a glycoprotein is provided which is obtained by the methods according to the invention. In yet another embodiment of the invention, a glycoprotein with reduced levels of core alfa(1,3)-fucose residues is provided which is obtained by the methods according to the invention. In yet a further embodiment, a glycoprotein with reduced levels of core alfa(1,3)-fucose and beta(1,2)-xylose residues is provided which is obtained by the methods according to the invention.

Another embodiment of the invention provides a *Nicotiana benthamiana* plant, or a cell, part, seed or progeny thereof, comprising at least three knock-out alfa(1,3)-fucosyltransferase genes. Yet another embodiment of the invention provides a *Nicotiana benthamiana* plant, or a cell, part, seed or progeny thereof, comprising at least five knock-out alfa(1,3)-fucosyltransferase genes. In yet a further embodiment, said plant or plant cell is homozygous for the knock-out alfa(1,3)-fucosyltransferase genes. In another embodiment, said plant or plant cell further comprises at least one knock-out beta(1,2)-xylosyltransferase gene, wherein said knock-out beta(1,2)-xylosyltransferase gene comprises a mutated DNA region consisting of one or more inserted, deleted or substituted nucleotides compared to a corresponding wild-type DNA region in the beta(1,2)-xylosyltransferase gene and wherein said knock-out beta(1,2)-xylosyltransferase gene does not encode a functional beta(1,2)-xylosyltransferase protein.

In yet another embodiment, the said plant or plant cell further comprises at least one chimeric gene comprising the following operably linked DNA fragments: a plant-expressible promoter; a DNA region, which when transcribed yields an RNA molecule inhibitory to at least one alfa(1,3)-fucosyltransferase encoding gene; and a DNA region comprising a transcription termination and polyadenylation signal functional in plants. In a further embodiment, said DNA region comprises the sequence of SEQ ID No. 19.

In a further embodiment, said plant or plant cell further comprises a glycoprotein foreign to said plant or plant cell. In yet another embodiment, said glycoprotein is expressed from a chimeric gene comprising the following operably linked nucleic acid molecules: a plant-expressible promoter, a DNA region encoding said heterologous glycoprotein, and a DNA region involved in transcription termination and polyadenylation.

In another embodiment of the invention, knock-out alleles of alfa(1,3)-fucosyltransferase genes are provided.

Yet another embodiment provides the use of the methods according to the invention to obtain glycoproteins with a reduced level of core alfa(1,3)-fucose residues. A further embodiment provides the use of the methods according to the invention to obtain glycoproteins with a reduced level of core alfa(1,3)-fucose residues and with a reduced level of beta(1,2)-xylose residues.

BRIEF DESCRIPTION OF THE FIGURES

FIG. 4: Crossing scheme used to obtain homozygous seven-fold knock out plants. x14: mutant allele XYL001 (XylTg14-1 as described in WO2010145846), x19: XYL002 (XylTg19-1 as described in WO2010145846), a: FucT004, b: FucT006, c: FucT007, d: FucT009, e: FucT003. The "x14/x14 x19/x19" refers to the double knock XylT mutant previously described in WO2010145846.

In the full knock-out *N. benthamiana* plant, all XylT and/or FucT genes have been knocked out (FucT004, -006, -007, -009, and -003, and XylTg14-1 and XylTg19-1 as described in WO2010145846). IgG1 was expressed in these full knock-out plants using magnICON®. IgG1 was isolated from leaf extract nine days after infiltration using protein G. The heavy chain of the purified antibody was isolated by cutting the corresponding band from a reducing SDS-PAGE. The heavy chain protein in this band was used for glycan analysis by LC-MS as described by Kolarich et al. (2006) Proteomics 6:3369.

The upper panel shows a wider mass spectrum to illustrate the presence of non-glycosylated peptides. Peptide 1 (EEQYNSTY) and peptide 2 (TKPREEQYNSTYR) are two variants from the same trypsin digestion. They differ in length caused by steric hindrance of the trypsin by the presence of N-glycans. As a result, all peptide-glycans produce two peaks in this LC-MS spectrum; those for glycopeptide 2 in the lower panel are indicated with an arrow.

Figure 10:
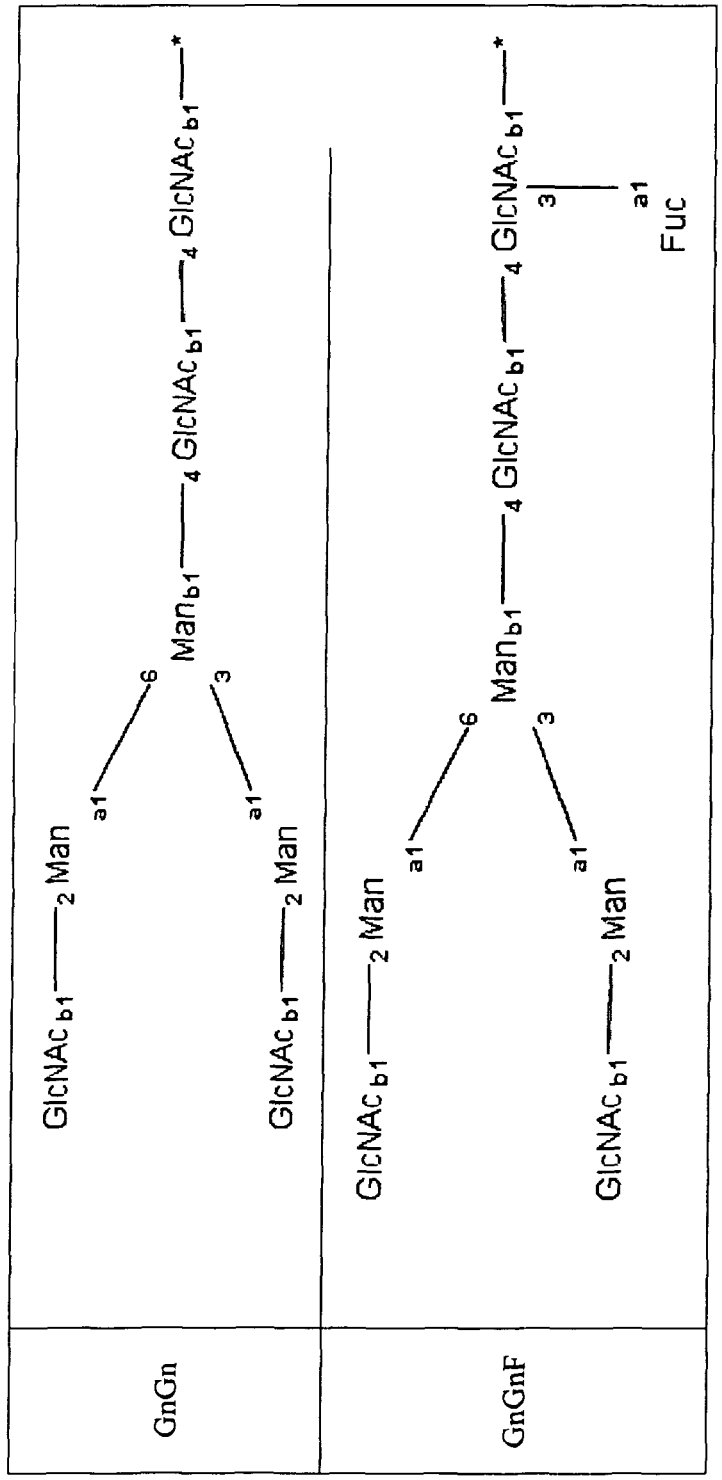

FIG. 10: Structure of N-glycans (See also http://www.proglycan.com for a current nomenclature of N-glycans). * indicates the bond between the indicated sugar chain and an asparagine of the peptidic part of the resulting glycoprotein.

Figure 11:
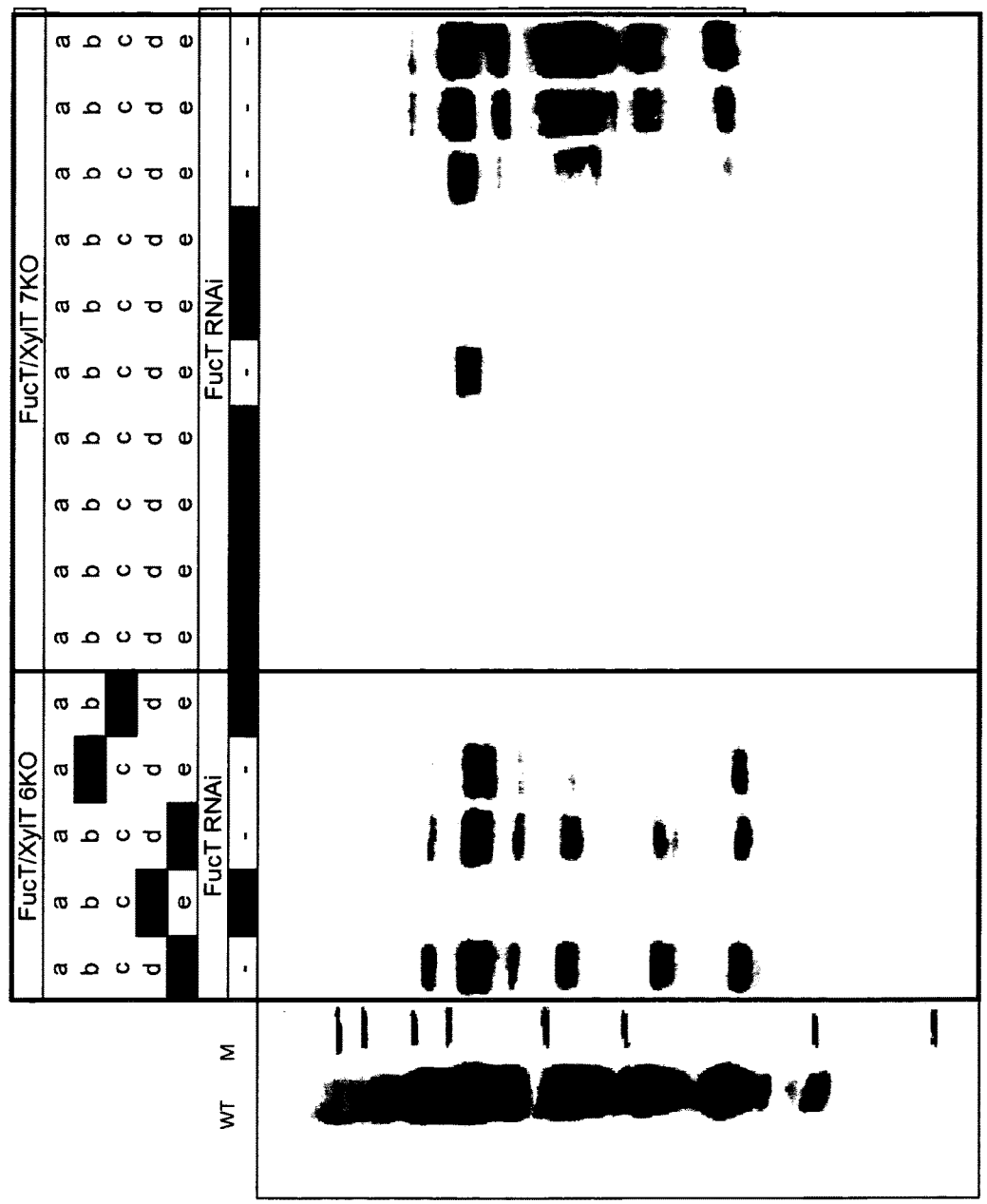

FIG. 11: Comparison of fucosylation levels of protein samples from *N. benthamiana* plants in which 6 or 7 genes have been knocked out. Plants containing the FucT RNAi gene are compared with plants which do not contain this gene. Western blot analysis of leaf protein samples. Probed with anti-α1,3 fucose antibody (1/500 dilution); 1 hour exposure for chemoluminescence. WT: Wild Type plant; M: Protein Marker. Knocked-out versions of the gene are indicated in the table as lower case; wild type version as upper case.

Figure 12:
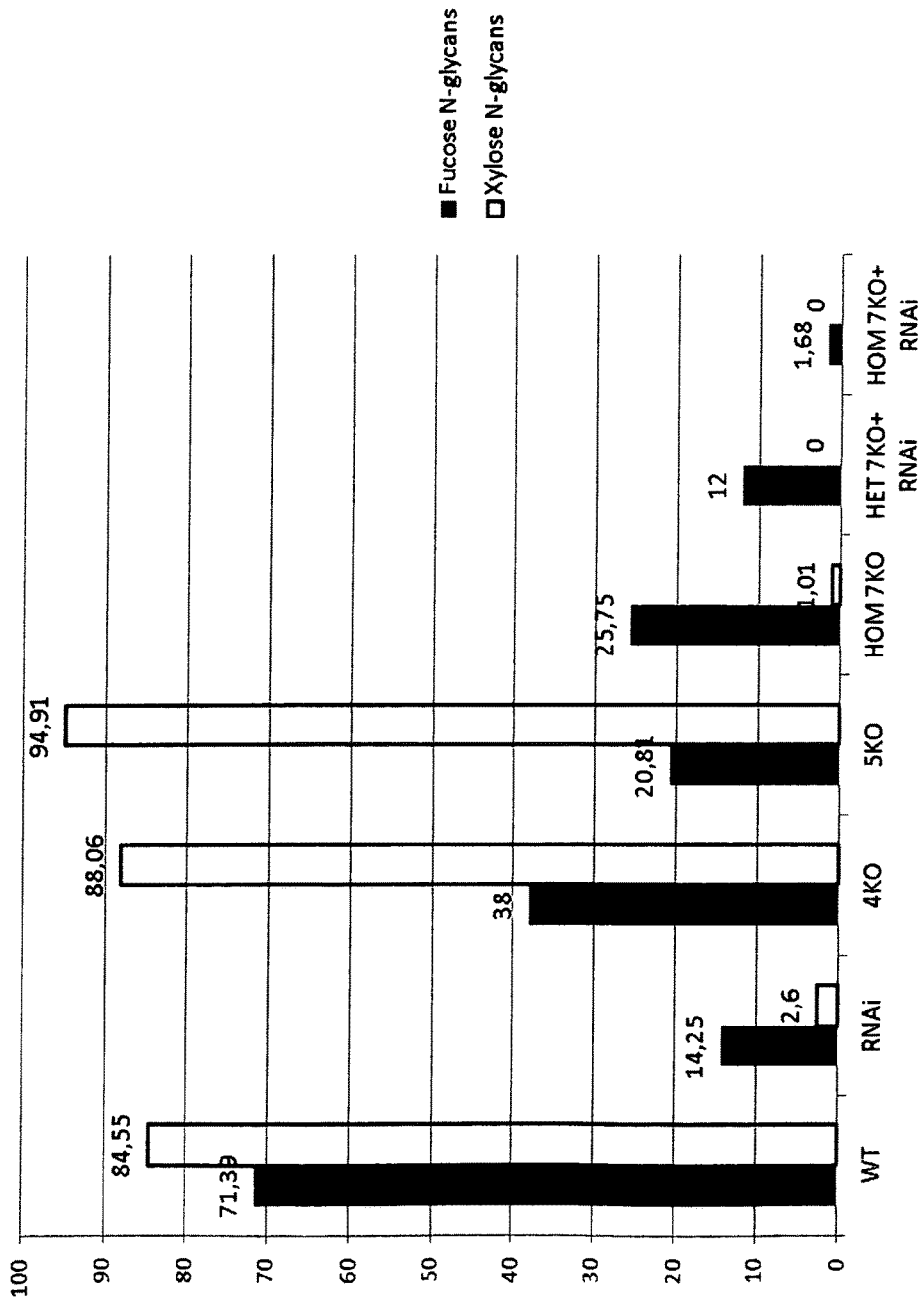

FIG. 12: Quantitative overview of fucosylated respectively xylosylated N-glycans present on the endogenous proteins of WT, 4-, 5-, 7-fold KO, RNAi and 7KO/FucT RNAi plants. Total protein was isolated from leaves of plants and glycans were isolated and analyzed by MALDI-TOF. Glycan levels are expressed as the sum of all different fucosylated respectively xylosylated N-glycan peaks as determined from the MALDI-TOF spectra. WT: wild-type (average of two lines). RNAi: plants expressing XylT and FucT RNAi genes (Strasser et al. 2008, Plant Biotech J 6:392) (average of two lines). 4KO: all FucT genes except FucTE knocked out (average of six lines). 5KO: all FucT genes knocked out (average of three lines). HOM7KO: all FucT and XylT genes knocked out (average of three lines). HET7KO+RNAi: XylT and FucTA genes knocked out and other FucT genes are heterozygously knocked out combined with the FucT RNAi gene (average of four lines). HOM7KO+FucT RNAi: plants homozygous for all seven knock-out genes and containing the FucT RNAi gene (average of four lines).

DETAILED DESCRIPTION OF DIFFERENT EMBODIMENTS OF THE INVENTION

The current invention is based on the identification of five genes encoding alfa(1,3)-fucosyltransferase in *Nicotiana benthamiana*, and that knocking-out more of these genes progressively reduces the levels of core alfa(1,3)-fucose residues on proteins produced in said plant.

In a first embodiment, the invention provides a method to produce glycoproteins with reduced levels of core alfa(1,3)-fucose residues in *Nicotiana benthamiana*, said method comprising the steps of providing a plant or plant cell comprising at least three knock-out alfa(1,3)-fucosyltransferase genes, and cultivating said cell and isolating glycoproteins from said cell.

"Reduced levels of core alfa(1,3)-fucose residues" or "a reduced level of core alfa(1,3)-fucose residues" as used herein is meant to be a reduction of levels of core alfa(1,3)-fucose residues with respect to levels as obtained in control plants. The "control plant" is generally a selected target plant which may be any plant, and may advantageously be selected among tobacco and related species like *Nicotiana*, including *N. benthamiana*, *N. tabacum*, and *S. tuberosum*, or other plants such as *M. sativa*. Generally, in the control plant the alfa(1,3)-fucosyltransferase gene is unmodified and it has wild-type levels of alfa(1,3)-fucosyltransferase activity.

"Wild type levels of alfa(1,3)-fucosyltransferase activity" (also written "wildtype" or "wild-type"), as used herein, refers to the typical level of alfa(1,3)-fucosyltransferase activity in a plant as it most commonly occurs in nature. Said control plant has thus not been provided either with a silencing nucleic acid molecule targeted to the endogenous alfa(1,3)-fucosyltransferase encoding gene or with an allele of an alfa(1,3)-fucosyltransferase gene associated with a low level of α-1,3-fucosyltransferase activity, such as a knockout allele.

Said reduced levels of core alfa(1,3)-fucose residues can consist of a reduction of at least 50%, or at least 60%, or at least 70%, or at least 80%, or at least 90%, or at least 95%, or at least 97%, or at least 99%. The amount of alfa(1,3)-fucosylated glycan structures associated with a produced glycoprotein can be determined according to the methods described in this invention.

"Core alfa(1,3)-fucose residues", also "alfa(1,3)-fucose residues", or "alpha(1,3)-fucose residues" or "α(1,3)-fucose residues" as used herein refers to a fucose that is alpha 1,3-linked to the core region of N-glycans.

"Alfa(1,3)-fucosyltransferase" or "alpha(1,3)-fucosyltransferase", or α(1,3)-fucosyltransferase", or "FucT" is an enzyme that catalyses the transfer of fucose from GDP-fucose to the core β-linked N-acetyl glucosamine (GlcNAc) of protein-bound N-glycans (EC 2.4.1.214).

Genes encoding alfa(1,3) fucosyltransferase (FucT) in plants include the following database entries identifying experimentally demonstrated and putative FucT cDNA and gene sequences, parts thereof or homologous sequences: NM 112815 (*Arabidopsis thaliana*), NM103858 (*Arabidop-*

*sis thaliana*), AJ 618932 (*Physcomitrella patens*) At1g49710 (*Arabidopsis thaliana*), At3g19280 (*Arabidopsis thaliana*). DQ789145 (*Lemna minor*), AY557602 (*Medicago truncatula*) Y18529 (*Vigna radiata*) AP004457 (*Oryza sativa*), AJ891040 encoding protein CAI70373 (*Populus alba*× *Populus tremula*) AY082445 encoding protein AAL99371 (*Medicago sativa*) AJ582182 encoding protein CAE46649 (*Triticum aestivum*) AJ582181 encoding protein CAE46648 (*Hordeum vulgare*), and EF562630.1 (*Nicotiana benthamiana*) (all sequences herein incorporated by reference).

A "Knock-out alfa(1,3)-fucosyltransferase gene" or "knock-out alfa(1,3)-fucosyltransferase allele" or "knock-out allele of the alfa(1,3)-fucosyltransferase gene" or "knock-out FucT gene" or "knock-out FucT allele" as used herein refers to a gene or an allele of said gene which does not complement the *Arabidopsis thaliana* triple knock-out as described by Kang et al. (2008, Proc Natl Acad Sci USA 105: 5933), using the methods as described in this invention. Said "knock-out alfa(1,3)-fucosyltransferase gene" is a wild-type alfa(1,3)-fucosyltransferase gene or allele, which comprises one or more mutations in its nucleic acid sequence. Said knock-out gene can, for example, be a gene that is not transcribed into a functional mRNA, or a gene of which the encoded RNA is not spliced correctly, or a gene not encoding a functional protein. Knock-out genes may thus comprise, for example, genes with mutations in promoter regions, with mutations in splice-sites, or with mutations coding sequences resulting in amino acid substitutions or resulting in premature translation termination.

A mutation can be a deletion, an insertion or a substitution of one or more nucleotides. Mutations can be either "natural mutations" which are mutations found in nature (e.g. produced spontaneously without human application of mutagens) or "induced mutations", which are induced by human intervention, e.g. by mutagenesis and are called non-natural mutant null alleles.

"Mutagenesis", as used herein, refers to the process in which plant cells (e.g., a plurality of *Nicotiana benthamiana* seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more alfa(1, 3)-fucosyltransferase genes may be accomplished by use of chemical means such as by contact of one or more plant tissues with ethylmethylsulfonate (EMS), ethylnitrosourea, etc., by the use of physical means such as x-ray, etc, or by gamma radiation, such as that supplied by a Cobalt 60 source. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, *Nicotiana benthamiana* plants are regenerated from the treated cells using known techniques. For instance, the resulting *Nicotiana benthamiana* seeds may be planted in accordance with conventional growing procedures and following self-pollination seed is formed on the plants. Additional seed that is formed as a result of such self-pollination in the present or a subsequent generation may be harvested and screened for the presence of mutant alfa(1,3)-fucosyltransferase genes. Several techniques are known to screen for specific mutant genes, e.g., Deleteagene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, *Nat Biotechnol* 18:455-457) identifies EMS-induced point mutations, direct sequencing, etc.

Mutant alfa(1,3)-fucosyltransferase genes may be generated (for example induced by mutagenesis) and/or identified using a range of methods, which are conventional in the art, for example using PCR based methods to amplify part or all of the alfa(1,3)-fucosyltransferase genomic or cDNA and direct sequencing.

Following mutagenesis, plants are grown from the treated seeds, or regenerated from the treated cells using known techniques. For instance, mutagenized seeds may be planted in accordance with conventional growing procedures and following self-pollination seed is formed on the plants. Additional seed which is formed as a result of such self-pollination in the present or a subsequent generation may be harvested and screened for the presence of mutant alfa(1, 3)-fucosyltransferase genes, using techniques which are conventional in the art, for example polymerase chain reaction (PCR) based techniques (amplification of the alfa(1,3)-fucosyltransferase genes) or hybridization based techniques, e.g. Southern blot analysis, BAC library screening, and the like, and/or direct sequencing of alfa(1,3)-fucosyltransferase genes. To screen for the presence of point mutations (so called Single Nucleotide Polymorphisms or SNPs) in mutant alfa(1,3)-fucosyltransferase genes, SNP detection methods conventional in the art can be used, for example oligo-ligation-based techniques, single base extension-based techniques, techniques based on differences in restriction sites, such as TILLING, or direct sequencing and comparing the sequences to wild-type sequeces using, for example, NovoSNP (Weckx et al, 2005, Genome Res 15: 436).

As described above, mutagenization (spontaneous as well as induced) of a specific wild-type alfa(1,3)-fucosyltransferase gene results in the presence of one or more deleted, inserted, or substituted nucleotides (hereinafter called "mutation region") in the resulting mutant alfa(1,3)-fucosyltransferase gene. The mutant alfa(1,3)-fucosyltransferase gene can thus be characterized by the location and the configuration of the one or more deleted, inserted, or substituted nucleotides in the wild type alfa(1,3)-fucosyltransferase gene.

Once a specific mutant alfa(1,3)-fucosyltransferase gene has been sequenced, primers and probes can be developed which specifically recognize the mutant alfa(1,3)-fucosyltransferase gene in biological samples (such as samples of plants, plant material or products comprising plant material).

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

In another embodiment, a method is provided to produce glycoproteins with reduced levels of core alfa(1,3)-fucose residues and reduced levels of beta(1,2)-xylose residues in *Nicotiana benthamiana*, said method comprising the steps of: providing a plant cell comprising at least three knock-out alpha(1,3)-fucosyltransferase genes; and having a reduced level of beta(1,2)-xylosyltransferase activity; and cultivating said cell and isolating glycoproteins from said cell.

"Reduced levels of beta(1,2)-xylose residues" as used herein is meant to be a reduction of levels of core beta(1,2)-xylose residues with respect to levels as obtained in control plants. The "control" plant is generally a selected target plant which may be any plant and may advantageously be selected among tobacco and related species like *Nicotiana*, including *N. benthamiana*, *N. tabacum*, and *S. tuberosum*, or other plants such as *M. sativa*. Generally, in the control plant the beta(1,2)-xylosyltransferase gene is unmodified and it has wild-type levels of beta(1,2)-xylosyltransferase activity. "Wild type levels of beta(1,2)-xylosyltransferase activity" (also written "wildtype" or "wild-type"), as used herein, refers to the typical level of beta(1,2)-xylosyltransferase activity in a plant as it most commonly occurs in nature. Said control plant has thus not been provided either with a silencing nucleic acid molecule targeted to the endogenous beta(1,2)-xylosyltransferase encoding gene or with an allele of an beta(1,2)-xylosyltransferase gene associated with a low level of beta(1,2)-xylosyltransferase activity, such as a knock-out allele.

Said reduced levels of beta(1,2)-xylosyltransferase residues can consist of a reduction of at least 50%, or at least 60%, or at least 70%, or at least 80%, or at least 90%, or at least 95%, or at least 97%, or at least 99%. The amount of beta(1,2)-xylosylated glycan structures associated with a produced glycoprotein can be determined according to the methods described in this invention.

"Reduced levels of core alfa(1,3)-fucose residues and reduced levels of beta(1,2)-xylose residues" can consist of a reduction of the levels of glycans comprising alfa(1,3)-fucose residues, beta(1,2)-xylose residues, or alfa(1,3)-fucose and beta(1,2)-xylose residues. Said reduction can consist of a reduction of at least 50%, or at least 60%, or at least 70%, or at least 80%, or at least 90%, or at least 95%, or at least 97%, or at least 99%. The amount of alfa(1,3)-fucosylated and beta(1,2)-xylosylated glycan structures associated with a produced glycoprotein can be determined according to the methods described in this invention.

The level of beta(1,2)-xylosyltransferase activity can be reduced by reducing the expression of endogenous beta(1,2)-xylosyltransferase encoding genes.

By "reducing the expression" of a stated integer it is meant that transcription and/or translation and/or post-translational modification of the integer is inhibited or prevented or knocked-down or knocked-out or interrupted such that the specified integer has a reduced biological effect on a cell, tissue, organ or organism in which it would otherwise be expressed.

Those skilled in the art will be aware of whether expression is inhibited, interrupted or reduced, without undue experimentation. For example, the level of expression of a particular gene may be determined by polymerase chain reaction (PCR) following reverse transcription of an mRNA template molecule. Alternatively, the expression level of a genetic sequence may be determined by northern hybridisation analysis or dot-blot hybridisation analysis or in situ hybridisation analysis or similar technique, wherein mRNA is transferred to a membrane support and hybridised to a "probe" molecule which comprises a nucleotide sequence complementary to the nucleotide sequence of the mRNA transcript encoded by the gene-of-interest, labeled with a suitable reporter molecule such as a radioactively-labelled dNTP (eg [alpha-32P] dCTP or [alpha-35S] dCTP) or biotinylated dNTP, amongst others. Expression of the gene-of-interest may then be determined by detecting the appearance of a signal produced by the reporter molecule bound to the hybridised probe molecule.

Alternatively, the rate of transcription of a particular gene may be determined by nuclear run-on and/or nuclear run-off experiments, wherein nuclei are isolated from a particular cell or tissue and the rate of incorporation of rNTPs into specific mRNA molecules is determined. Alternatively, the expression of the gene-of-interest may be determined by RNase protection assay, wherein a labelled RNA probe or "riboprobe" which is complementary to the nucleotide sequence of mRNA encoded by said gene-of-interest is annealed to said mRNA for a time and under conditions sufficient for a double-stranded mRNA molecule to form, after which time the sample is subjected to digestion by RNase to remove single-stranded RNA molecules and in particular, to remove excess unhybridised riboprobe. Such approaches are described in detail by Sambrook, J., Fritsch, E. F. and Maniatis, T. Molecular Cloning: a laboratory manual. 2nd ed. N.Y., Cold Spring Harbor Laboratory, Cold Spring Harbor Laboratory Press, 1989. 1659 p. ISBN 0-87969-309-6.

Those skilled in the art will also be aware of various immunological and enzymatic methods for detecting the level of expression of a particular gene at the protein level, for example using rocket immunoelectrophoresis, ELISA, radioimmunoassay and western blot immunoelectrophoresis techniques, amongst others.

The level of beta(1,2)-xylosyltransferase activity can conveniently be reduced or eliminated by transcriptional or post-transcriptional silencing of the expression of endogenous beta(1,2)-xylosyltransferase encoding genes. To this end a silencing RNA molecule is introduced in the plant cells targeting the endogenous beta(1,2)-xylosyltransferase encoding genes.

As used herein, "silencing RNA" or "silencing RNA molecule" refers to any RNA molecule, which upon introduction into a plant cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having 95% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 bp (see WO04/073390, herein incorporated by reference). Silencing RNA may also be artificial micro-RNA molecules as described e.g. in WO2005/052170, WO2005/047505 or US 2005/0144667, or ta-siRNAs as described in WO2006/074400 (all documents incorporated herein by reference).

A suitable method for silencing the beta(1,2)-xylosyltransferase is the method as described in WO2009056155.

In a particular embodiment of the invention, the reduced level of beta(1,2)-xylosyltransferase is activity is the result of a knock-out mutation in endogenous beta(1,2)-xylosyltransferase genes.

"A knock-out mutation in endogenous beta(1,2)-xylosyltransferase genes" as used herein is a mutation that renders the beta(1,2)-xylosyltransferase gene inactive, wherein the inactive gene is characterized in that the gene does not encode a functional alfa(1,3)-fucosyltransferase protein. Said gene, also referred to as "knock-out gene" or "knock-out allele" can either be a gene that is not transcribed into a functional mRNA, or a gene of which the encoded RNA is not spliced correctly, or a gene not encoding a functional protein. Mutations that render the beta(1,2)-xylosyltransferase gene inactive thus comprise, for example, mutations in the promoter regions, mutations in the splice-sites, or mutations in the coding sequences resulting in amino acid substitutions or premature translation termination.

Suitable knock-out mutations in endogenous beta(1,2)-xylosyltransferase genes of *Nicotiana benthamiana* are the knock-outs as described in WO2010145846.

The alfa(1,3)-fucosyltransferase and the beta(1,2)-xylosyltransferase activity can be evaluated by determining the level of alfa(1,3)-fucose and the level of beta(1,2)-xylose residues on protein-bound N-glycans from a plant, respectively. The level of alfa(1,3)-fucose and the level of beta(1,2)-xylose residues on protein-bound N-glycans from a plant can be measured e.g. by Western blot analysis using fucose- or xylose specific antibodies, as described e.g. by Faye et al. (Analytical Biochemistry (1993) 209: 104-108) or by mass spectrometry on glycans isolated from the plant's glycoproteins using Matrix-Assisted Laser Desorption/Ionization Time-of-Flight Mass Spectrometry (MALDI-TOF-MS) as described e.g. by Kolarich and Altmann (Anal. Biochem. (2000) 285: 64-75), or using Liquid-Chromatography-ElectroSpray Ionization-Mass Spectrometry (LC/ESI/MS) as described by Pabst et al. (Analytical Chemistry (2007) 79: 5051-5057) or using Liquid Chromatography Tandem Mass Spectrometry (LC/MS/MS) as described e.g. by Henriksson et al. (Biochem. J. (2003) 375: 61-73).

In yet another embodiment of the method of the invention, said plant or plant cell comprises at least five knock-out alfa(1,3)-fucosyltransferase genes.

At least five knock-out alfa(1,3)-fucosyltransferase genes can be five knock-out alfa(1,3)-fucosyltransferase genes, or six alfa(1,3)-fucosyltransferase genes, or seven alfa(1,3)-fucosyltransferase genes, or more than seven alfa(1,3)-fucosyltransferase genes.

Suitable knock-out alfa(1,3)-fucosyltransferase genes can be mutated versions of the native alfa(1,3)-fucosyltransferase genes selected from the group consisting of nucleic acids encoding the amino acid sequence of SEQ ID No. 3, SEQ ID No. 6, SEQ ID No. 9, SEQ ID No. 12, SEQ ID No. 14, or of nucleic acids encoding amino acid sequences having at least 80%, or at least 85%, or at least 90%, or at least 95%, or at least 97%, or at least 98%, or at least 99% identity to these amino acid sequences.

Suitable knock-out alfa(1,3)-fucosyltransferase genes can further be mutated versions of the native alfa(1,3)-fucosyltransferase genes selected from the group consisting of SEQ ID No. 1, SEQ ID No. 4, SEQ ID No. 7, SEQ ID No. 10, SEQ ID No. 13, or of nucleic acids having at least 80%, or at least 85%, or at least 90%, or at least 95%, or at least 97%, or at least 98%, or at least 99% identity to these sequences.

In yet another embodiment of the method of the invention, said knock-out alfa(1,3)-fucosyltransferase genes are mutated versions of the native alfa(1,3)-fucosyltransferase genes selected from the group consisting of:
  a nucleic acid molecule encoding an amino acid sequence comprising at least 90% sequence identity to SEQ ID NO: 3;
  a nucleic acid molecule encoding an amino acid sequence comprising at least 90% sequence identity to SEQ ID NO: 6;
  a nucleic acid molecule encoding an amino acid sequence comprising at least 90% sequence identity to SEQ ID NO: 9;
  a nucleic acid molecule encoding an amino acid sequence comprising at least 90% sequence identity to SEQ ID NO: 12;
  a nucleic acid molecule encoding an amino acid sequence comprising at least 90% sequence identity to SEQ ID NO: 14.

In a further embodiment, said knock-out alfa(1,3)-fucosyltransferase genes are mutated versions of the native alfa(1,3)-fucosyltransferase genes selected from the group consisting of:
  a nucleic acid molecule comprising at least 90% sequence identity to SEQ ID NO: 1;
  a nucleic acid molecule comprising at least 90% sequence identity to SEQ ID NO: 4;
  a nucleic acid molecule comprising at least 90% sequence identity to SEQ ID NO: 7;
  a nucleic acid molecule comprising at least 90% sequence identity to SEQ ID NO: 10;
  a nucleic acid molecule comprising at least 90% sequence identity to SEQ ID NO: 13.

Suitable knock-out alfa(1,3)-fucosyltransferase genes for the invention are genes with one or more mutations selected from the group of mutations as depicted in Table 2 and Table 4.

In yet a further embodiment, said knock-out alfa(1,3)-fucosyltransferase gene is selected from the group consisting of:
  FucTA gene containing a G to A substitution at position 355 of SEQ ID NO: 1;
  FucTB gene containing a G to A substitution at position 3054 of SEQ ID NO: 4;
  FucTC gene containing a G to A substitution at position 2807 of SEQ ID NO: 7;
  FucTD gene containing a G to A substitution at position 224 of SEQ ID NO: 10;
  FucTE gene containing a G to A substitution at position 910 of SEQ ID NO: 13.

A "mutated version" of a gene as used herein is a version of a gene which contains one or more mutations. A "native alfa(1,3)-fucosyltransferase", also "wild-type alfa(1,3)-fucosyltransferase" as used herein refers to a typical form of an alfa(1,3)-fucosyltransferase gene as it most commonly occurs in nature.

In another specific embodiment, said knock-out alfa(1,3)-fucosyltransferase genes occur in a homozygous state in the genome.

In another embodiment according to the invention, the method according to the invention is further characterized in that the expression of at least five endogenous alfa(1,3)-fucosyltransferase encoding genes is reduced through transcriptional or post-transcriptional silencing. Transcriptional and post-transcriptional silencing can suitably be achieved by introducing a silencing RNA molecule in the plant cells targeting the endogenous alfa(1,3)-fucosyltransferase encoding genes.

For silencing at least five endogenous alfa(1,3)-fucosyltransferase encoding genes, it is suitable to introduce more than one chimeric gene into the plant cells, characterized in that each of the chimeric genes encodes a silencing RNA molecule, each of which is suitable to silence at least one of the alfa(1,3)-fucosyltransferase genes. Alternatively, one chimeric gene can be introduced in the plant cells which encodes a silencing RNA molecule capable of silencing at least five alfa(1,3)-fucosyltransferase genes. Said one chimeric gene can comprise several regions of 21 consecutive nucleotides, each of which having at least 85% sequence identity to a region of 21 nucleotides occurring in at least one of the alfa(1,3)-fucosyltransferase genes. Alternatively, said one chimeric gene can comprise a region of 21 consecutive nucleotides characterized that at least five alfa(1,3)-fucosyltransferase genes comprise a sequence of 21 nucleotides having 85% identity to said region of 21 consecutive nucleotides.

A suitable methods for silencing the alfa(1,3)-fucosyltransferase genes of *Nicotiana benthamiana* are the methods as described in WO2009056155.

In yet a further embodiment, the plant cell according to the invention comprises at least one chimeric gene comprising the following operably linked DNA fragments: a plant-expressible promoter, a DNA region, which when transcribed yields an RNA molecule inhibitory to at least one alfa(1,3)-fucosyltransferase encoding gene, a DNA region comprising a transcription termination and polyadenylation signal functional in plants. In a further embodiment, said DNA region yields an RNA molecule capable of forming a double-stranded RNA region at least between an RNA region transcribed from a first sense DNA region comprising a nucleotide sequence of at least 18 out of 21 nucleotides selected from SEQ ID NO: 2, SEQ ID NO: 5, SEQ ID NO: 8, SEQ ID NO: 11, SEQ ID NO: 13, or the complement thereof, and an RNA region transcribed from a second antisense DNA region comprising a nucleotide sequence of at least 18 consecutive nucleotides which have at least 95% sequence identity to the complement of said first sense DNA region.

"An RNA molecule inhibitory to at least one alfa(1,3)-fucosyltransferase encoding gene" as used herein refers to a silencing RNA molecule which reduces the expression of at least one alfa(1,3)-fucosyltransferase encoding gene.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al. (1988) *Mol Gen Genet.* 212(1):182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) *Plant Cell* 8(1):15-30), stem-specific promoters (Keller et al., (1988) *EMBO J.* 7(12): 3625-3633), leaf specific promoters (Hudspeth et al. (1989) *Plant Mol Biol.* 12: 579-589), mesophyl-specific promoters (such as the light-inducible Rubisco promoters), root-specific promoters (Keller et al. (1989) *Genes Dev.* 3: 1639-1646), tuber-specific promoters (Keil et al. (1989) *EMBO J.* 8(5): 1323-1330), vascular tissue specific promoters (Peleman et al. (1989) *Gene* 84: 359-369), stamen-selective promoters (WO 89/10396, WO 92/13956), dehiscence zone specific promoters (WO 97/13865) and the like.

A "transcription termination and polyadenylation region" as used herein is a sequence that drives the cleavage of the nascent RNA, whereafter a poly(A) tail is added at the resulting RNA 3' end, functional in plants. Transcription termination and polyadenylation signals functional in plants include, but are not limited to, 3'nos, 3'35S, 3'his and 3'g7.

In yet a further embodiment, the plant cell according to the invention comprises a chimeric gene comprising a plant-expressible promoter, a DNA region, which when transcribed yields an RNA molecule inhibitory to at least one alfa(1,3)-fucosyltransferase encoding gene, and a DNA region comprising a transcription termination and polyadenylation signal functional in plants, characterized in that said DNA region comprises the sequence of SEQ ID No. 19.

In another embodiment of the invention, the glycoproteins produced according to the methods of the invention are heterologous glycoproteins. In yet another embodiment, said heterologous proteins are expressed from a chimeric gene comprising the following operably linked nucleic acid molecules: a plant-expressible promoter, a DNA region encoding said heterologous glycoprotein, a DNA region involved in transcription termination and polyadenylation. In yet another embodiment, the methods according to the invention further comprise the step of purification of said heterologous proteins.

The word "expression" as used herein shall be taken in its widest context to refer to the transcription of a particular genetic sequence to produce sense or antisense mRNA or the translation of a sense mRNA molecule to produce a peptide, polypeptide, oligopeptide, protein or enzyme molecule. In the case of expression comprising the production of a sense mRNA transcript, the word "expression" may also be construed to indicate the combination of transcription and translation processes, with or without subsequent post-translational events which modify the biological activity, cellular or sub-cellular localization, turnover or steady-state level of the peptide, polypeptide, oligopeptide, protein or enzyme molecule.

Heterologous glycoproteins, i.e. glycoproteins which are not normally expressed in such plant cells in nature, may include mammalian or human proteins, which can be used as therapeutics such as e.g. monoclonal antibodies. Conveniently, the foreign glycoproteins may be expressed from chimeric genes comprising a plant-expressible promoter and the coding region of the glycoprotein of interest, whereby the chimeric gene is stably integrated in the genome of the plant cell. Methods to express foreign proteins in plant cells are well known in the art. Alternatively, the foreign glycoproteins may also be expressed in a transient manner, e.g.

using the viral vectors and methods described in WO02/088369, WO2006/079546 and WO2006/012906 or using the viral vectors described in WO89/08145, WO93/03161 and WO96/40867 or WO96/12028.

By "heterologous protein" it is understood a protein (i.e. a polypeptide) that is not expressed by the plant or plant cells in nature. This is in contrast with a homologous protein which is a protein naturally expressed by a plant or plant cell. Heterologous and homologous polypeptides that undergo post-translational N-glycosylation are referred to herein as heterologous or homologous glycoproteins.

Examples of heterologous proteins of interest that can be advantageously produced by the methods of this invention include, without limitation, cytokines, cytokine receptors, growth factors (e.g. EGF, HER-2, FGF-alpha, FGF-beta, TGF-alpha, TGF-beta, PDGF, IGF-I, IGF-2, NGF), growth factor receptors. Other examples include growth hormones (e.g. human growth hormone, bovine growth hormone); insulin (e.g., insulin A chain and insulin B chain), pro-insulin, erythropoietin (EPO), colony stimulating factors (e.g. G-CSF, GM-CSF, M-CSF); interleukins; vascular endothelial growth factor (VEGF) and its receptor (VEGF-R), interferons, tumor necrosis factor and its receptors, thrombopoietin (TPO), thrombin, brain natriuretic peptide (BNP); clotting factors (e.g. Factor VIII, Factor IX, von Willebrands factor and the like), anti-clotting factors; tissue plasminogen activator (TPA), urokinase, follicle stimulating hormone (FSH), luteinizing hormone (LH), calcitonin, CD proteins (e.g., CD2, CD3, CD4, CD5, CD7, CD8, CDI Ia, CDI Ib, CD18, CD19, CD20, CD25, CD33, CD44, CD45, CD71, etc.), CTLA proteins (e.g.CTLA4); T-cell and B-cell receptor proteins, bone morphogenic proteins (BNPs, e.g. BMP-I, BMP-2, BMP-3, etc.), neurotrophic factors, e.g. bone derived neurotrophic factor (BDNF), neurotrophins, e.g. rennin, rheumatoid factor, RANTES, albumin, relaxin, macrophage inhibitory protein (e.g. MIP-I, MIP-2), viral proteins or antigens, surface membrane proteins, ion channel proteins, enzymes, regulatory proteins, immunomodulatory proteins, (e.g. HLA, MHC, the B7 family), homing receptors, transport proteins, superoxide dismutase (SOD), G-protein coupled receptor proteins (GPCRs), neuromodulatory proteins, Alzheimer's Disease associated proteins and peptides. Fusion proteins and polypeptides, chimeric proteins and polypeptides, as well as fragments or portions, or mutants, variants, or analogs of any of the aforementioned proteins and polypeptides are also included among the suitable proteins, polypeptides and peptides that can be produced by the methods of the present invention. The protein of interest can be a glycoprotein. One class of glycoproteins are viral glycoproteins, in particular subunits, than can be used to produce for example a vaccine. Some examples of viral proteins comprise proteins from rhinovirus, poliomyelitis virus, herpes virus, bovine herpes virus, influenza virus, newcastle disease virus, respiratory syncitio virus, measles virus, retrovirus, such as human immunodeficiency virus or a parvovirus or a papovavirus, rotavirus or a coronavirus, such as transmissable gastroenteritisvirus or a flavivirus, such as tick-borne encephalitis virus or yellow fever virus, a togavirus, such as rubella virus or eastern-, western-, or venezuelean equine encephalomyelitis virus, a hepatitis causing virus, such as hepatitis A or hepatitis B virus, a pestivirus, such as hog cholera virus or a rhabdovirus, such as rabies virus.

The heterologous glycoprotein can be an antibody or a fragment thereof. The term "antibody" refers to recombinant antibodies (for example of the classes IgD, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatised variants thereof that retain the ability to specifically bind an epitope. Antibody derivatives may comprise a protein or chemical moiety conjugated to an antibody. A monoclonal antibody is capable of selectively binding to a target antigen or epitope. Antibodies include, monoclonal antibodies (mAbs), humanized or chimeric antibodies, camelized antibodies, camelid antibodies (Nanobodies®), single chain antibodies (scFvs), Fab fragments, F(ab')$_2$ fragments, disulfide-linked Fvs (sdFv) fragments, anti-idiotypic (anti-Id) antibodies, intra-bodies, synthetic antibodies, and epitope-binding fragments of any of the above. The term "antibody" also refers to fusion protein that includes a region equivalent to the Fc region of an immunoglobulin. Also envisaged is the production in the plant or plant cells of the invention of so called dual-specificity antibodies (Bostrom J et al (2009) *Science* 323, 1610-1614).

Antibodies within the scope of the present invention include those comprising the amino acid sequences of the following antibodies: anti-HER2 antibodies including antibodies comprising the heavy and light chain variable regions (see U.S. Pat. No. 5,725,856) or Trastuzumab such as HERCEPTIN™; anti-CD20 antibodies such as chimeric anti-CD20 as in U.S. Pat. No. 5,736,137, a chimeric or humanized variant of the 2H7 antibody as in U.S. Pat. No. 5,721,108; anti-VEGF antibodies including humanized and/or affinity matured anti-VEGF antibodies such as the humanized anti-VEGF antibody huA4.6.1 AVASTIN™ (WO 96/30046 and WO 98/45331); anti-EGFR (chimerized or humanized antibody as in WO 96/40210); anti-CD3 antibodies such as OKT3 (U.S. Pat. No. 4,515,893); anti-CD25 or anti-tac antibodies such as CHI-621 (SIMULECT) and (ZENAPAX) (U.S. Pat. No. 5,693,762). The present invention provides a method for the production of an antibody which comprises culturing a transformed plant cell or growing a transformed plant of the present invention. The produced antibody may be purified and formulated in accordance with standard procedures.

The DNA region encoding the heterologous glycoproteins may be codon optimized to increase the level of expression within the plant. By codon optimization it is meant the selection of appropriate DNA nucleotides for the synthesis of oligonucleotide building blocks, and their subsequent enzymatic assembly, of a structural gene or fragment thereof in order to approach codon usage in plants.

"Purification" as used herein is to isolate the heterologous protein from the mixture of total plant proteins. The level of purification can be to at least 50% purity, or to at least 60% purity, or to at least 70% purity, or to at least 80% purity, or to at least 85% purity, or to at least 90% purity, or to at least 95% purity, or to at least 98% purity, or to at least 99% purity. Methods for protein purification are well-known in the art and may consist of, but are not limited to, differential precipitation, ultracentrifugation, chromatography, or affinity purification.

Another embodiment of the invention provides a glycoprotein obtained by the methods according to the invention. In yet another embodiment, said glycoprotein has reduced levels of alfa(1,3)-fucose residues. In yet a further embodiment, said glycoprotein has reduced levels of alfa(1,3)-fucose residues and reduced levels of beta(1,2)-xylose residues.

Another embodiment according to the invention provides a *Nicotiana benthamiana* plant, or a cell, part, seed or progeny thereof, comprising at least three knock-out alfa(1,3)-fucosyltransferase genes. In yet another embodiment, said plant comprises at least five knock-out alfa(1,3)-fucosyltransferase genes.

At least five knock-out alfa(1,3)-fucosyltransferase genes can be five knock-out alfa(1,3)-fucosyltransferase genes, or six knock-out alfa(1,3)-fucosyltransferase genes, or seven knock-out alfa(1,3)-fucosyltransferase genes, or at least seven knock-out alfa(1,3)-fucosyltransferase genes.

Suitable knock-out alfa(1,3)-fucosyltransferase genes can be mutated versions of the native alfa(1,3)-fucosyltransferase genes selected from the group consisting of nucleic acids encoding the amino acid sequence of SEQ ID No. 3, SEQ ID No. 6, SEQ ID No. 9, SEQ ID No. 12, SEQ ID No. 14, or of nucleic acids encoding amino acid sequences having at least 80%, or at least 85%, or at least 90%, or at least 95%, or at least 97%, or at least 98%, or at least 99% identity to these amino acid sequences.

Suitable knock-out alfa(1,3)-fucosyltransferase genes can further be mutated versions of the native alfa(1,3)-fucosyltransferase genes selected from the group consisting of SEQ ID No. 1, SEQ ID No. 4, SEQ ID No. 7, SEQ ID No. 10, SEQ ID No. 13, or of nucleic acids having at least 80%, or at least 85%, or at least 90%, or at least 95%, or at least 97%, or at least 98%, or at least 99% identity to these sequences.

Another embodiment provides plants according to invention, wherein one or more of the knock-out alfa(1,3)-fucosyltransferase genes is a mutated version of the native alfa(1,3)-fucosyltransferase gene selected from the group consisting of:
  a nucleic acid molecule encoding an amino acid sequence comprising at least 90% sequence identity to SEQ ID NO: 3;
  a nucleic acid molecule encoding an amino acid sequence comprising at least 90% sequence identity to SEQ ID NO: 6;
  a nucleic acid molecule encoding an amino acid sequence comprising at least 90% sequence identity to SEQ ID NO: 9;
  a nucleic acid molecule encoding an amino acid sequence comprising at least 90% sequence identity to SEQ ID NO: 12;
  a nucleic acid molecule encoding an amino acid sequence comprising at least 90% sequence identity to SEQ ID NO: 14.

Yet another embodiment provides plants according to the invention, wherein one or more of the knock-out alfa(1,3)-fucosyltransferase genes is a mutated version of the native alfa(1,3)-fucosyltransferase gene selected from the group consisting of:
  a nucleic acid molecule comprising at least 90% sequence identity to SEQ ID NO: 1;
  a nucleic acid molecule comprising at least 90% sequence identity to SEQ ID NO: 4;
  a nucleic acid molecule comprising at least 90% sequence identity to SEQ ID NO: 7;
  a nucleic acid molecule comprising at least 90% sequence identity to SEQ ID NO: 10;
  a nucleic acid molecule comprising at least 90% sequence identity to SEQ ID NO: 13.

Yet another embodiment provides plants according to the invention wherein the knock-out alfa(1,3)-fucosyltransferase gene is selected from the group consisting of:
  FucTA gene containing a G to A substitution at position 355 of SEQ ID NO: 1;
  FucTB gene containing a G to A substitution at position 3054 of SEQ ID NO: 4;
  FucTC gene containing a G to A substitution at position 2807 of SEQ ID NO: 7;
  FucTD gene containing a G to A substitution at position 224 of SEQ ID NO: 10;
  FucTE gene containing a G to A substitution at position 910 of SEQ ID NO: 13.

In a further embodiment, the plant or plant cell according to the invention is homozygous for the knock-out alfa(1,3)-fucosyltransferase genes.

In yet another embodiment, the plant or plant cell according to the invention further comprises at least one knock-out beta(1,2)-xylosyltransferase gene, wherein said knock-out beta(1,2)-xylosyltransferase gene comprises a mutated DNA region consisting of one or more inserted, deleted or substituted nucleotides compared to a corresponding wild-type DNA region in the beta(1,2)-xylosyltransferase gene and wherein said knock-out beta(1,2)-xylosyltransferase gene does not encode a functional beta(1,2)-xylosyltransferase protein.

In yet another embodiment, the said plant or plant cell further comprises at least one chimeric gene comprising the following operably linked DNA fragments: a plant-expressible promoter; a DNA region, which when transcribed yields an RNA molecule inhibitory to at least one alfa(1,3)-fucosyltransferase encoding gene; and a DNA region comprising a transcription termination and polyadenylation signal functional in plants.

Suitably, said DNA region yields an RNA molecule capable of forming a double-stranded RNA region at least between an RNA region transcribed from a first sense DNA region comprising a nucleotide sequence of at least 18 out of 21 nucleotides selected from SEQ ID NO: 2, SEQ ID NO: 5, SEQ ID NO: 8, SEQ ID NO: 11, SEQ ID NO: 13, or the complement thereof, and an RNA region transcribed from a second antisense DNA region comprising a nucleotide sequence of at least 18 consecutive nucleotides which have at least 95% sequence identity to the complement of said first sense DNA region.

In a further embodiment, said DNA region comprises the sequence of SEQ ID No. 19.

In a further embodiment, the plant or plant cell according to the invention further comprises a glycoprotein foreign to said plant or plant cell. In yet another embodiment, said glycoprotein is expressed from a chimeric gene comprising the following operably linked nucleic acid molecules: a plant-expressible promoter, a DNA region encoding said heterologous glycoprotein, a DNA region involved in transcription termination and polyadenylation.

Another embodiment according to the invention provides a knock-out allele of an alfa(1,3)-fucosyltransferase gene selected from the group consisting of:
  FucTA gene containing a G to A substitution at position 355 of SEQ ID NO: 1;
  FucTB gene containing a G to A substitution at position 3054 of SEQ ID NO: 4;
  FucTC gene containing a G to A substitution at position 2807 of SEQ ID NO: 7;
  FucTD gene containing a G to A substitution at position 224 of SEQ ID NO: 10;
  FucTE gene containing a G to A substitution at position 910 of SEQ ID NO: 13.

Yet another embodiment provides the use of the methods according to the invention to obtain glycoproteins with a reduced level of core alfa(1,3)-fucose residues. A further embodiment provides the use of the methods according to the invention to obtain glycoproteins with a reduced level of core alfa(1,3)-fucose residues and with a reduced level of beta(1,2)-xylose residues.

Plants according to the invention can be further crossed by traditional breeding techniques and can be used to produce seeds to obtain progeny plants comprising glycoproteins with reduced levels of alfa(1,3)-fucosylation and/or reduced levels of beta(1,2)-xylosylation.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

Unless stated otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York". Standard materials and references are described in "Croy R D D (ed.) (1993) Plant Molecular Biology LabFax, BIOS Scientific Publishers Ltd., Oxford and Blackwell Scientific Publications, Oxford" and in "Brown T A, (1998) Molecular Biology LabFax, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com".

All patents, patent applications, and publications or public disclosures (including publications on internet) referred to or cited herein are incorporated by reference in their entirety.

Throughout the description and Examples, reference is made to the following sequences:

```
SEQ ID No 1:        FucTA genomic DNA

SEQ ID No 2:        FucTA coding sequence

SEQ ID No 3:        FucTA protein

SEQ ID No 4:        FucTB genomic DNA

SEQ ID No 5:        FucTB coding sequence

SEQ ID No 6:        FucTB protein

SEQ ID No 7:        FucTC genomic DNA

SEQ ID No 8:        FucTC coding sequence

SEQ ID No 9:        FucTC protein

SEQ ID No 10:       FucTD genomic DNA

SEQ ID No 11:       FucTD coding sequence

SEQ ID No 12:       FucTD protein

SEQ ID No 13:       FucTE genomic DNA

SEQ ID No 14:       FucTE protein

SEQ ID No 15:       Primer VH031

SEQ ID No 16:       Primer VH032

SEQ ID No 17:       Primer VH033

SEQ ID No 18:       Primer VH034

SEQ ID No 19:       Sequence encoding FucT silencing RNA

SEQ ID No 20:       Sequence encoding FucT silencing RNA: part of the Nicotiana
                    benthamiana FucTB coding sequence from 1183 to 1265:
                    gaaactgtctatcatgtatatgtacgtgaaagagggaggtttgagatggattccattttcttaagg
                    tcgagtgatttgtcttt SEQ ID No 21:       Sequence encoding FucT silencing RNA:

FH Key              Location/Qualifiers

FH

FT intron           84 . . . 307

FT                  /vntifkey = "15"
```

```
FT                      /label = intron\2
FT                      /note = "Arabidopsis XylT gene intron 2"
FT    misc_feature      1 . . . 83
FT                      /vntifkey = "21"
FT                      /label = Nb\FucTB
FT                      /note = "Part of N. benthamiana FucTB coding sequence
                        from 1183-1265"
FT    misc_feature      complement(308 . . . 390)
FT                      /vntifkey = "21"
FT                      /label = Nb\FucTB
FT                      /note = "Inverse complement of part of N. benthamiana
                        FucTB coding sequence from 1183-1265"
SQ                      Sequence 390 BP; 100 A; 71 C; 79 G; 140 t;

gaaactgtct atcatgtata tgtacgtgaa agagggaggt ttgagatgga ttccattttc        60
ttaaggtcga gtgatttgtc tttgatccac tgcacggtat gctcctcttc ttgttcatgg       120
tcatgatcct tatatgagca gggaaagtcc agtttagact tgtagttagt tactcttcgt       180
tataggattt ggatttcttg cgtgtttatg gttttagttt ccctcctttg atgaataaaa       240
ttgaatcttg tatgagtttc atatccatgt tgtgaatctt tttgcagacg cagctaggta       300
ccggatcaaa gacaaatcac tcgaccttaa gaaaatggaa tccatctcaa acctccctct       360
ttcacgtaca tatacatgat agacagtttc
```

EXAMPLES

1. Isolating the FucT Genes from *Nicotiana benthamiana*

Figure 1:
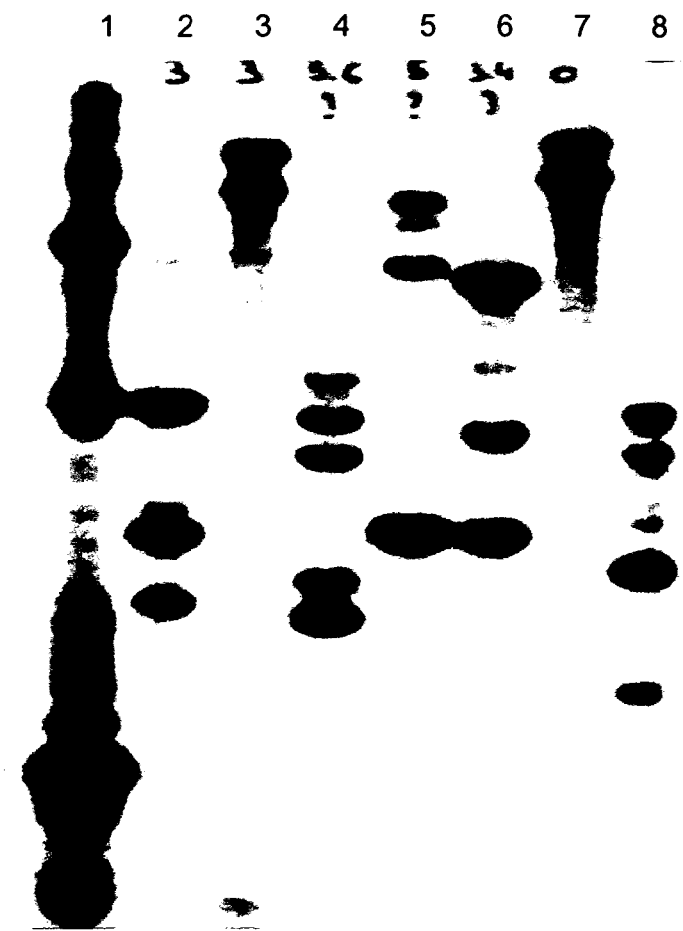
FIG. 1: Results from Southern blot hybridization of *N. benthamiana* genomic DNA hybridized with a cDNA probe of FucTA from *N. benthamiana*. lane 1=lambda marker, lanes 2-7: *N. benthamiana* genomic DNA digested with EcoRV (lane 2), HindIII (lane 3), EcoRI (lane 4), NsiI (lane 5), AseI (lane 6), PstI (lane 7); lane 8=*Nicotiana tabacum* cv. SR1 digested with EcoRV and HindIII.

To produce a FucT KO plant, it was needed to identify and isolate all members of the FucT gene family. Therefore, we first determined the gene family size by Southern blot analysis. Genomic DNA from *N. benthamiana* was digested with EcoRI, EcoRV, PstI, HindIII, NsiI, or AseI, run on 1% agarose gel and blotted on nylon membrane. The blots were hybridized with a cDNA clone of FucTA from *N. benthamiana* (Strasser et al. (2008) Plant Biotech J. 6:392). After exposure, the autoradiogram showed up to seven hybridizing bands per lane indicating a family of maximum seven genes (FIG. 1).

Figure 2:
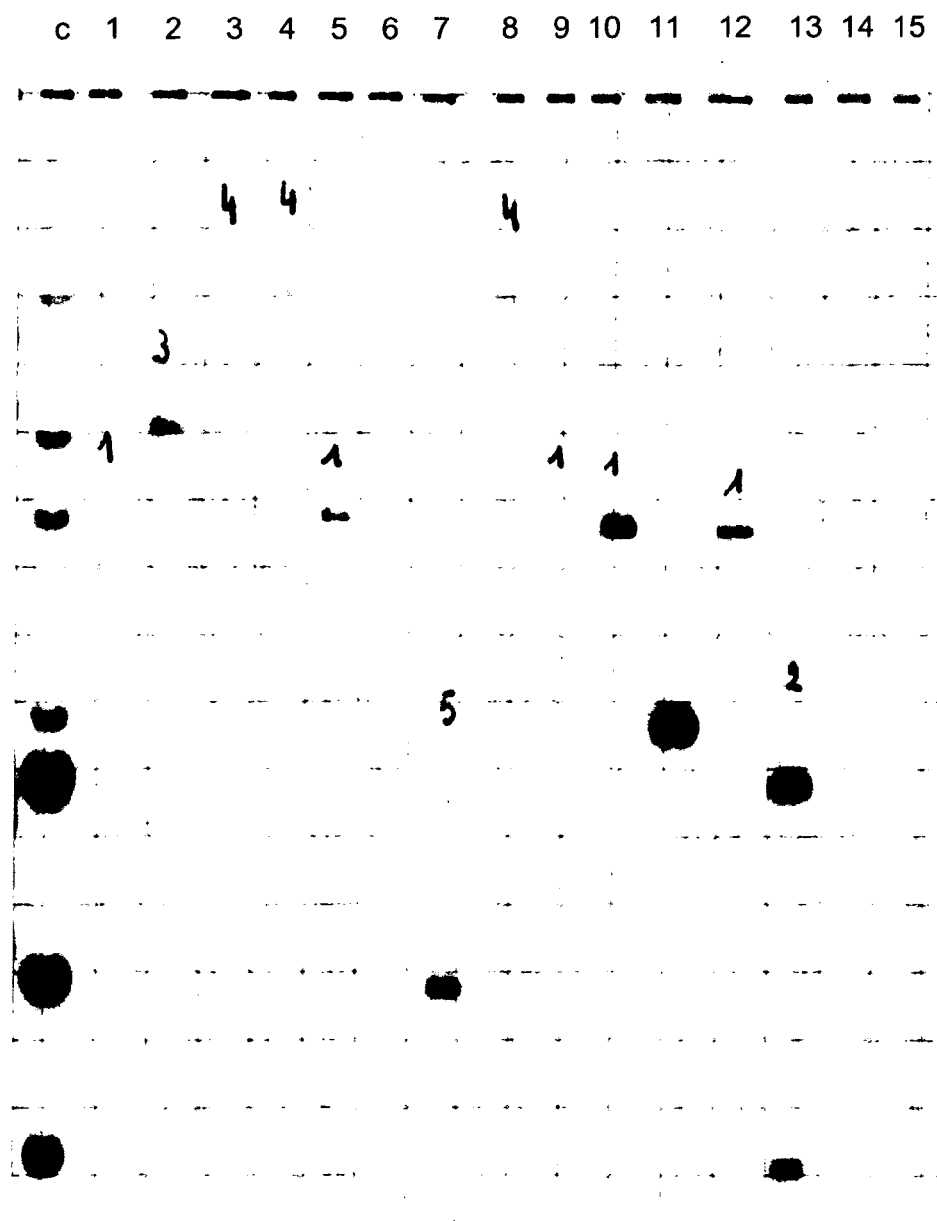
FIG. 2: Example of a Southern blot comparing hybridization patterns of BAC clones (lanes 1-15) with the hybridization pattern of *N. benthamiana* genomic DNA (c).

To isolate all members of this FucT gene family, 2 BAC libraries were constructed by Amplicon Express. Each covered the genome 2.5 fold using MboI and HindIII as cloning enzymes, respectively. The libraries were screened with the FucTA cDNA probe. In total, 32 BAC clones were found. These clones were classified into different families based on Southern blot analyses comparing the hybridization pattern of each individual clone with the hybridization pattern of *N. benthamiana* genomic DNA (FIG. 2). Of the 32 clones, 8 did not hybridize. The remaining clones could be classified into 8 families. Five of these families displayed hybridization patterns that overlapped with bands in the *N. benthamiana* genomic Southern blot hybridization.

One representative of each BAC clone family was sequenced using 454 sequencing technology and analyzed for the presence of a FucT gene by BLAST homology search using the FucTA cDNA sequence. Of the 8 families tested in this way, five contained FucT sequences that were all full length with respect to the FucTA coding sequence. These five genes were named FucTA, -B, -C, -D, and -E. The sequences of these five FucT genes are represented in SEQ ID No 1, SEQ ID No 4, SEQ ID No 7, SEQ ID No 10, and SEQ ID No 13, respectively.

EST2Genome (Mott (1997) Comput. Applic. 13:477) analysis using these contigs and the published FucTA cDNA sequence, showed that all genes except FucTE have the same number of introns as compared to the *A. thaliana* FucT-A and -B genes and that the intron-exon boundaries are also preserved between these two species. Surprisingly, no introns were found in the *N. benthamiana* FucTE gene. The FucT-D gene was found to contain an unusually large intron 1 of 7833 bp.

Analysis of the upstream sequences for promoter elements using TSSP (Shahmuradov et al. (2005) Nucl. Acids Res. 33:1069) showed that all genes except FucTE had TATA regions predicted with high confidence levels. In addition, analysis of the amino acid sequence of FucTE gene showed that it contains a Tyrosine to Aspartic Acid substitution at position 288 (Y288D). This position is part of the highly conserved donor substrate binding site ("MOTIFII") and mutation of this Tyrosine residue has been shown to completely inactivate the enzyme activity of human FucT VI (Jost et al. 2005 Glycobiology 15:165). By contrast, all other *N. benthamiana* FucT genes contain the conserved Tyrosine residue at this position. Together, this indicates that FucTE is likely an inactive gene coding for an inactive FucT enzyme.

Finally, to determine the homology between the genes, we aligned the derived coding sequences of the genes on the nucleotide level using the Clonemanager program, resulting in a FucT gene family divided in two groups: FucTA and FucTB form one group, FucTA has 100% identity to the previously published *N. benthamiana* FucTA cDNA (Strasser et al. (2008) Plant Biotech J. 6:392). The coding regions of FucTA and -B have 96% identity. The main striking difference between the two genes is that FucTB has a shorter coding sequence due to a premature stop codon. FucTC, FucTD and FucTE form the second group. All three genes have 96% identity in the coding regions. Genes from the two groups share 80% relative identity.

2. EMS Mutagenesis

We used EMS mutagenesis to come to a selection of null mutations for each FucT gene. Ethyl MethaneSulfonate (EMS) causes G→A and C→T point mutations by alkylating Guanine (G). These point mutations can knock out genes if they generate null mutations by inducing stop codons or splice site mutations. Using this method we can screen for knock outs for all FucT genes. A total knock out will be achieved after crossing these mutants.

Determination of the Optimal EMS Dosage for M2 Seed Production.

Different EMS dosages and the effect on seed set, germination and plant phenotype were tested. This was needed to find out the optimal EMS dose to find EMS induced FucT knock outs in *N. benthamiana*.

Figure 3:
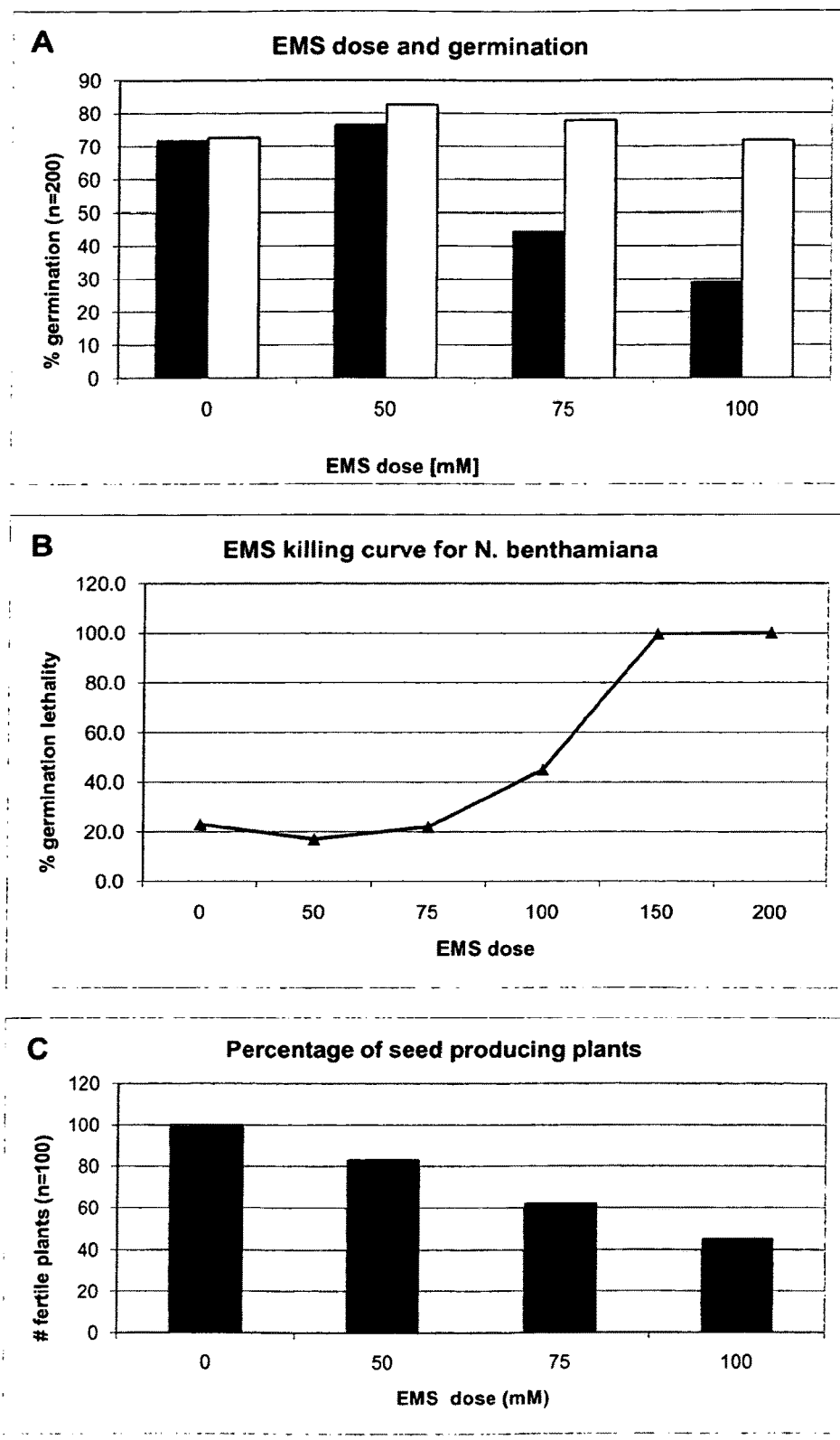
FIG. 3: Determining optimum EMS dose for production of M2 seeds in *N. benthamiana*. Seeds were treated with different concentrations of EMS. A: Germination rate 6 days (black bars) and 12 days (white bars) after sowing. B: Seed survival. C: plant fertility.

The optimum dose for EMS mutagenesis was determined by treating seeds with 0, 50, 75, 100, 150, and 200 mM EMS. Briefly, seeds were imbibed for 2 hours at room temperature, treated with EMS for 4 hours at room temperature and washed 5 times for 15 minutes at room temperature. Seeds were dried overnight and sown immediately. The effects on germination, seedling lethality and plant fertility were recorded. As *N. benthamiana* most probably is an amphidiploid species from a combination of *N. debneyi* and *N. suaveolens* (Goodspeed, T. H. 1954 Pages 485-487 in: The Genus *Nicotiana*: Origins, Relationships and Evolution of its Species in the Light of Their Distribution, Morphology and Cytogenetics. Chronica Botanica, Waltham, Mass., U.S.A.) they initially were also included in the tests. However, as they showed to be less sensitive to EMS as compared to *N. bethamiana* (data not shown) they were not used for the fertility tests. Although EMS treatment caused a delay in germination (FIG. 3A), no lethality was detected up to 75 mM EMS. At higher EMS doses, lethality rose quickly and at 150 mM no seeds survived the treatment (FIG. 3B). Fertility already was affected at 50 mM. By treating the seeds with 75 mM approximately 60% of the M1 plants were infertile (FIG. 3C). Based on these results, the optimum EMS dose was set at 75 mM.

Production of EMS-Mutagenized Plants and DNA Samples of M2 Populations to Screen for FucT Mutants.

To have a good chance finding our mutants, we needed to screen about 10000 plants. To obtain more than 10000 M2 plants by using the EMS dosage of 75 mM, we needed to grow at least 20000 M1 plants. At the determined density and generation time, 7000 M1 plants could be grown in 4 months. Therefore, at least 3 M1 populations needed to be grown. M2 seed was sown and a DNA extraction on leaf samples of the M2 *N. benthamiana* plants was done. The DNA extraction was done in-house, extracting 4 leaf discs per plant following the in-house Edwards and Kingfisher method. DNA plates coming from 1 EMS treatment were defined as EMS batch.

In total we made 6 EMS batches. Two batches failed: batch 2 due to a bad mutation frequency, batch 4 due to the plant death unrelated to EMS mutagenesis. Together, four batches were left, comprising 99 plates of 95 DNA samples each extracted from M2 *N. benthamiana* leaf samples. On position H12 of each plate we included an internal control DNA sample of *N. benthamiana* accession NBNPGS2 from the USDA National Germplasm System (accession code PI555684). This accession contained several known SNPs compared to the *benthamiana* accession used for EMS mutagenesis (i.e. Cultivar "BENTHAMIANA" supplied by Icon Genetics GmbH). The positions of these SNPs are summarized in Table 1. Plates were stored at −70° C.

TABLE 1

SNP's in the sequences of the FucT genes between Bayer's "*BENTHAMIANA*" and NBNPGS2 accessions (USDA National Germplasm System accession PI555684).

| | exon 3(target 1) | | exon 1 (target2) | |
|---|---|---|---|---|
| | position | SNP | position | SNP |
| FucTA | 3080 | T/C | 32 | A/T |
| | | | 63 | C/G |
| | | | 76 | A/G |
| FucTB | | | 218 | T/A |
| | | | 296 | A/C |
| | | | 307 | G/T |
| FucTC | 2809 | C/T | | |
| FucTD | 9653 | G/A | 34 | A/C |
| | 9656 | C/A | 56 | T/C |
| | 9710 | G/A | 107 | T/C |
| | 9833 | T/C | 192 | T/C |
| FucTE | 582 | T/A | 353 | G/A |
| | 708 | T/C | 427 | A/T |
| | 723 | A/G | | |
| | 725 | C/A | | |
| | 783 | C/T | | |
| | 912 | G/T | | |

Detecting EMS-Induced Point Mutations by Direct Sequencing and Single Nucleotide Polymorphism (SNP) Detection.

For high throughput detection of the EMS-induced point mutations by direct sequence analysis, we used the method described by Smits et al. (2006), Pharmacogenet. Genomics 16:159. The method was adapted for us by Agowa GmbH (currently part of LGC laboratory services). Briefly, specific gene fragments were amplified by PCR from DNA of leaf tissue of individual plants using gene specific primers. Each primer carried an to additional sequence at its 5' end that would allow the sequence of both strands of the resulting PCR fragment to be analyzed.

The chromatograms of sequences were analyzed for Single Nucleotide Polymorphisms (SNPs) by comparing them to the FucTA, FucTB, FucTC, FucTD and FucTE sequences in NovoSNP (Weckx, S. et al. 2005 Genome Research 15:436).

Defining the Target Area for Mutagenesis Detection.

Because the SNP detection by direct sequencing was limited to sequence fragments of 500 bp, it was necessary to identify a 500 bp region in the FucTA-E genes that had the highest chance to produce a null mutation when mutagenized with EMS. Therefore we needed to identify a region that (1) had the highest density of codons that can change into stop codons by one G to A or C to T mutation and/or splice donor and acceptor sites and (2) was placed in or upstream of a catalytic or conserved domain.

In order to find the highest density of candidate stop or splice mutations, we used an algorithm that identifies all codons in a coding sequence that can be mutated to a stop codon or a splice mutant by one EMS mutation.

Two general targets were defined for mutagenesis detection within the FucT genes:

For our first target our choice was based on a shared conserved amino acid sequence for the α1,3-FucT's "MOTIF II" and 2 other motifs, "Mn binding" and "SSD motif", upstream of "MOTIFII" (Jost et al. 2005 Glycobiology 15:165; Wilson et al. 2001 Biochim Biophys Acta. 1527:88). Therefore as target we took an exon between "MOTIFII" and the "Mn binding, SSD motif" described above. For the FucTA-D genes this was exon3 (nt 2833-3074 of SEQ ID No 1 for FucTA; nt 2813-3054 of SEQ ID No 4 for FucTB, nt 2565-2806 of SEQ ID No 7 for FucTC, and nt 9685-9926 of SEQ ID No 10 for FucTD), all having a length of 241 bp; for FucTE (consisting of only one exon) we took a fragment of 320 bp (nt 592-912 of SEQ ID No 13).

We screened a second target to have more chance in finding mutations. We took exon1, having the highest density of codons that can change into stop codons (nt 1-354 of SEQ ID No 1 for FucTA, nt 1-354 of SEQ ID No 4 for FucTB, nt 1-396 of SEQ ID No 7 for FucTC, nt 1-396 of SEQ ID No 10 for FucTD), and a fragment of 396 bp for FucTE (nt 1-396 of SEQ ID No 13).

As screening for mutants delivered stop codon mutants for all genes except FucTE and FucTA, of which the latter only delivered splice site mutants, it was decided to include a third target for the FucTA gene. This target was located in exon 2 (nt 1098-1258 of SEQ ID No 1).

For each gene, the possible SNP's causing a stop codon or splice site mutation are listed per target in Tables 2 and 3. It is clear that using exon1 as target should give a lot more possible stop codon- or splice site mutation positions. However these mutations had a lower confidence level to produce an effective knock out mutant, because it is possible that an ATG downstream of the mutation might function as a new start codon. This then could produce a protein devoid of a transmembrane domain which still could have an active glycosyltransferase activity (Jost et al., 2005, Glycobiology 15:165).

TABLE 2

Exon3, splice-site/stopcodon mutation prediction list of FucT genes.

| | FucTA | | | FucTB | | | FucTC | | | FucTD | | | FucTE | |
|---|---|---|---|---|---|---|---|---|---|---|---|---|---|---|
| | bas | pos. gen | pos. CD | bas | pos. gen | pos. CD | bas | pos. gen | pos. CD | bas | pos. gen | pos. CD | bas | pos. gen |
| SPLICE | A | 283 | 514 | A | 281 | 514 | A | 256 | 556 | A | 968 | 556 | T | 622 |
| | G | 283 | 515 | G | 281 | 515 | G | 256 | 557 | G | 968 | 557 | G | 623 |
| | A | 283 | 516 | A | 281 | 516 | A | 256 | 558 | A | 968 | 558 | G | 624 |
| | T | 289 | 580 | T | 287 | 580 | T | 262 | 622 | C | 977 | 652 | C | 652 |
| | G | 289 | 581 | G | 287 | 581 | G | 263 | 623 | A | 978 | 653 | A | 653 |
| | G | 289 | 582 | G | 287 | 582 | G | 263 | 624 | A | 978 | 654 | A | 654 |
| | C | 299 | 679 | C | 297 | 679 | C | 265 | 652 | C | 984 | 721 | C | 721 |
| | A | 299 | 680 | A | 297 | 680 | A | 266 | 653 | A | 984 | 722 | A | 722 |
| | A | 299 | 681 | A | 297 | 681 | A | 266 | 654 | G | 985 | 723 | A | 723 |
| SPLICE | G | 307 | | G | 305 | | C | 272 | 721 | G | 992 | | C | 880 |
| | G | 307 | | G | 305 | | A | 272 | 722 | G | 992 | | A | 881 |
| | T | 307 | | T | 305 | | G | 273 | 723 | T | 992 | | G | 882 |
| SPLICE | | | | | | | G | 280 | | | | | | |
| | | | | | | | G | 280 | | | | | | |
| | | | | | | | T | 280 | | | | | | |

Nucleotides that, when mutated with EMS, would result in the mutation of a splice-site or the introduction of a stopcodon are indicated gray.
Dashed lines indicate the actual splice site.
The positions of the nucleotides are given in the gene sequences and in the coding sequences.

TABLE 3

Exon1, splice site/stopcodon mutation prediction lists FucT genes.

| FucTA | | FucTB | | FucTC | | FucTD | | FucTE | |
|---|---|---|---|---|---|---|---|---|---|
| bas | pos. gen | bas | pos. gen | bas | pos. gen | bas | pos. gen | bas | pos. gen |
| C | 37 | C | 37 | C | 22 | C | 22 | C | 22 |
| A | 38 | A | 38 | A | 23 | A | 23 | A | 23 |
| A | 39 | A | 39 | A | 24 | A | 24 | A | 24 |
| T | 40 | T | 40 | C | 76 | C | 76 | C | 76 |
| G | 41 | G | 41 | A | 77 | A | 77 | A | 77 |
| G | 42 | G | 42 | A | 78 | A | 78 | A | 78 |
| T | 49 | T | 49 | T | 85 | T | 85 | T | 85 |
| G | 50 | G | 50 | G | 86 | G | 86 | G | 86 |
| G | 51 | G | 51 | G | 87 | G | 87 | G | 87 |
| C | 103 | C | 103 | T | 94 | T | 94 | T | 94 |
| G | 104 | G | 104 | G | 95 | G | 95 | G | 95 |
| A | 105 | A | 105 | G | 96 | G | 96 | G | 96 |
| T | 133 | T | 133 | C | 148 | C | 148 | C | 148 |
| G | 134 | G | 134 | G | 149 | G | 149 | G | 149 |
| G | 135 | G | 135 | A | 150 | A | 150 | A | 150 |
| C | 151 | C | 151 | T | 187 | T | 187 | T | 187 |
| A | 152 | A | 152 | G | 188 | G | 188 | G | 188 |
| G | 153 | G | 153 | G | 189 | G | 189 | G | 189 |
| T | 169 | T | 169 | C | 205 | C | 205 | C | 205 |
| G | 170 | G | 170 | A | 206 | A | 206 | A | 206 |
| G | 171 | G | 171 | G | 207 | G | 207 | G | 207 |
| C | 217 | C | 247 | T | 223 | T | 223 | T | 223 |
| A | 218 | A | 248 | G | 224 | G | 224 | G | 224 |
| G | 219 | G | 249 | G | 225 | G | 225 | G | 225 |
| T | 277 | T | 262 | C | 289 | T | 319 | T | 319 |
| G | 278 | G | 263 | A | 290 | G | 320 | G | 320 |
| G | 279 | G | 264 | G | 291 | G | 321 | G | 321 |
| C | 352 | T | 277 | T | 319 | G | 396 | | |
| A | 353 | G | 278 | G | 320 | G | 397 SPLICE | | |
| G | 354 SPLICE | G | 279 | G | 321 | T | 398 | | |
| G | 355 | C | 352 | G | 396 | | | | |
| T | 356 | A | 353 | G | 397 SPLICE | | | | |
| | | G | 354 | T | 398 | | | | |
| | | G | 355 SPLICE | | | | | | |
| | | T | 356 | | | | | | |

Nucleotides that, when mutated with EMS, would result in the mutation of a splice site or the introduction of a stopcodon are indicated gray.
Dashed lines indicate the actual splicesite.

Results from Screening the Different EMS-Mutagenized Populations for Possible Knock-Out Mutations in the Different FucT Genes For the FucT genes, the following number of EMS lines were screened: 4275 M2 individuals were screened for mutations in FucTA, 8075 for FucTB, 6555 for FucTC, 6270 for FucTD and 4370 for FucTE. The following number of putative null alleles were identified: three in FucTA, two splice site mutations and one stop codon mutation, respectively labeled FucT001, FucT004, and FucT013. Two putative null alleles, respectively one splice site mutation and one stop codon mutation, were identified for FucTB, labeled FucT006 and FucT008. For FucTC, 4 putative null alleles were identified, respectively 1 splice site mutation and three stop codon postitions, labeled FucT007, FucT010, FucT011 and FucT012. For FucTD, one splice site mutation and one stop codon mutation, were identified, labeled FucT005 and FucT009. Finally for FucTE, no stop codon mutations were identified. Instead, two alleles with substitution mutations were identified, labeled FucT002 and FucT003. The FucT003 substitution was located in the conserved "MOTIF II".

Table 4 summarizes the results of the screening for FucT genes: mutation position, mutation sequence and mutant type.

TABLE 4

Overview of possible EMS mutants for the FucT genes. Seeds comprising the mutants FucT004, FucT006, FucT007, FucT009 and FucT003 have been deposited at the National Collection of Industrial, Marine and Food Bacteria (NCIMB), NCIMB Ltd, Ferguson Building, Craibstone Estate, Bucksburn, Aberdeen AB219YA, Scotland, on 12 Sep. 2011, under accession number NCIMB 41860.

| Mutant Name | Position | WT Sequence | MUT sequence | Allele | Type |
|---|---|---|---|---|---|
| EMS mutants for FucTA | | | | | |
| FucT001 | 3074 | GGT | AGT | FucTA-1 | SPL |
| FucT004 | 355 | GGT | GAT | FucTA-2 | SPL |
| FucT013 | 1176 | CAA | TAA | FucTA-3 | STOP |
| EMS mutants for FucTB | | | | | |
| FucT006 | 3054 | GGT | AGT | FucTB-1 | SPL |
| FucT008 | 135 | TGG | TGA | FucTB-2 | STOP |
| EMS mutants for FucTC | | | | | |
| FucT007 | 2807 | GGT | GAT | FucTC-1 | SPL |
| FucT010 | 188 | TGG | TAG | FucTC-2 | STOP |
| FucT011 | 86 | TGG | TAG | FucTC-3 | STOP |
| FucT012 | 87 | TGG | TGA | FucTC-4 | STOP |
| EMS mutants for FucTD | | | | | |
| FucT005 | 397 | GGT | GAT | FucTD-1 | SPL |
| FucT009 | 224 | TGG | TAG | FucTD-2 | STOP |

TABLE 4-continued

Overview of possible EMS mutants for the FucT genes. Seeds comprising the mutants FucT004, FucT006, FucT007, FucT009 and FucT003 have been deposited at the National Collection of Industrial, Marine and Food Bacteria (NCIMB), NCIMB Ltd, Ferguson Building, Craibstone Estate, Bucksburn, Aberdeen AB219YA, Scotland, on 12 Sep. 2011, under accession number NCIMB 41860.

| Mutant Name | Position | WT Sequence | MUT sequence | Allele | Type |
|---|---|---|---|---|---|
| EMS mutants for FucTE | | | | | |
| FucT002 | 811 | GAA (Glu) | AAA (Lys) | FucTE-1 | SUBST |
| FucT003 | 910 | GTG (Val) | ATG (Met) | FucTE-2 | SUBST |

3. Crossing Scheme to Produce N. benthamiana Plants Homozygous for Knock Out Mutants of all XylT and FucT Genes: The Seven-Fold Knock Out Plant We retrieved homozygous mutants for all lines, listed in Table 4, by sowing and screening 24 plants from the original M2 seed lot in which the mutation had been identified. DNA samples from each of these plants were screened using the direct sequencing technique described above. We were unable to retrieve mutant FucT013.

The homozygous mutants that were selected this way, were allowed to self-fertilize to create a stable mutant seedlot. In addition, a selected number of mutants were entered into a 5-fold backcrossing scheme with the "BENTHAMIANA" accession to eliminate most if not all of the mutation drag. Finally, a selected number of mutants were entered in a crossing scheme to produce the 7-fold knock out plants. The crossing scheme is shown in FIG. 4. The final set of mutants that were used to generate the 7-fold knock out plant was: XYL001 (XylTg14-1 as described in WO2010145846), XYL002 (XylTg19-1 as described in WO2010145846), FucT003, FucT004, FucT006, FucT007, FucT009. The selection of the final set of FucT mutants was based on a gene transcription- and a complementation assay. Both are described below.

In order to be able to quickly and more economically identify zygosity of the mutant alleles in the back-crossing and crossing schemes describes above, an End Point Taq-Man assay was designed by Applied Bioscience. The RT-PCR analyses for this were run in-house. TaqMan probes are oligonucleotides that have a fluorescent reporter dye attached to the 5' end and a quencher moiety coupled to the 3' end. These probes are designed to hybridize to an internal region of a PCR product. In the unhybridized state, the proximity of the fluorescent and the quench molecules prevents the detection of a fluorescent signal from the probe. During PCR, when the polymerase replicates a template on which a TaqMan probe is bound, the 5'-nuclease activity of the polymerase cleaves the probe. This uncouples the fluorescent and quenching dyes. Thus, fluorescence increases in each cycle, proportional to the amount of probe cleavage which, in turn, is related to the zygosity level of the target. When compared to an internal standard, the level of fluorescence can thus be translated into the zygosity levels: "wt", "heterozygous" and "homozygous".

4. Linkage Analysis of the FucT Genes

To determine whether any of the FucT genes were genetically linked, we performed a linkage analysis making use of the SNPs in all FucT genes in accessions "BENTHAMIANA" and NBNPGS2 (USDA National Germplasm System accession PI555684; see also Table 1). To this end, BENTHAMIANA and NBNPGS2 were crossed, the F1 was crossed with BENTHAMIANA, and the FucT genotypes of 576 individuals from the next BC1 generation were analyzed.

If no linkage exists between any of the FucT genes, alleles would be seemingly randomly spread over the different individual's genotypes. If linkage exits between two or more FucT genes, this would show up as approximately 50% of the individuals being homozygous for two or more specific FucT genes. As the latter was not observed in the population of 96 that was analyzed, we concluded that the five FucT genes are unlinked.

5. Determining Whether the Different FucT Genes are being Transcribed

As the crossing scheme for the full knock out plant would run over 5 generations, we looked for opportunities to shorten this timeline. One possibility was to check whether any of the five FucT genes was not expressed. To determine this, we amplified FucT transcripts from leaf mRNA using primer sets with broad specificity. We then cloned and sequenced individual cDNAs resulting from this amplification. Sequence analysis of this set of clones should thus reveal if and which FucT genes were expressed. In addition, as we used primers that hybridized to regions that were conserved between FucT genes, we could pick up additional genes that we might have missed in the BAC screening.

cDNA was prepared from mRNA extracted from N. benthamiana leaves, following the protocol of the superscript II (Invitrogen) kit.

We performed a PCR on these cDNA samples, using primers designed on the FucTA CDS, taking the SNP's between genes into account. Using primers VH031 (SEQ ID No. 15) and VH032 (SEQ ID No. 16), described as primer combination 1 (PC1), a fragment of 570 bp will be amplified. Using primer combination 2 (PC2), formed by primers VH033 (SEQ ID No. 17) and VH034 (SEQ ID No. 18), a fragment of 348 bp will be amplified. The PCR's were run with annealing temperatures of 56° C. (PC2) and 62° C. (PC1), using a standard PCR mix [10 µl Go Taq buffer 5×; 1 µl dNTM 10 mM; 1 µl forward primer 10 µM; 1 µl reverse primer 10 µM; 0.4 µl Taq polymerase 5 U/µl; 2 µl purified PCR product in 50 µl total volume] and standard protocol [2 min 94° C.; 30×[30 sec 94° C., 30 sec 56° C./62° C., 30 sec 72° C.], 10 min 72° C.].

The resulting PCR products were purified with the Qiagen PCR purification kit, cloned in the PGemT Easy vector (Promega) and transformed into commercial thermo competent TOP10 cells (Invitrogen). 100 µl was plated out on LB plates containing 100 µg/ml triacelline. 192 clones resulting from primer combination PC1 and 96 from PC2 were sequenced by AGOWA. Based on SNPs in the five FucT sequences, it was possible to distinguish which of the different FucT genes was expressed.

For PC1, 148 clones gave usable sequence information resulting in 61 clones homologous to FucTA, 58 to FucTB, 2 to FucTC, 27 to FucTD and none for FucTE, 44 samples failed by sequencing. Checking the 96 clones of PC2, we found 15 clones homologous to FucTA, 39 to FucTB, none to FucTC, 12 to FucTD and none to FucTE, 30 samples failed by sequencing. In addition, none of the two primer combinations produced any new FucT sequences.

Together, this indicated that likely all FucT genes except for FucTE are expressed in *N. benthamiana* leaves. These findings corroborate the TSSP prediction data presented in example 1. In addition, these results indicated that likely no other FucT genes are present besides the five that were identified by BAC screening.

As FucTE appeared not to be expressed in *N. benthamiana* leaves, we decided to keep the FucTE gene as last one to cross into to the crossing scheme for the 7-fold knock out plant (see "generation 4" in FIG. 4).

6. Complementation Assay Shows which FucT Genes are Likely Active and which Mutations are Likely Null Mutations In order to determine the functionality of the individual FucT genes and also to determine whether the putative null mutations, that were isolated from our EMS screen, are true null or knock-out mutants, we devised a complementation assay. In this assay, the mutant to be complemented was an *Arabidopsis thaliana* line in which the FucT and XylT genes were knocked out by T-DNA insertion ("triple knock-out mutant"). This line has been described by Kang et al. (2008) Proc Natl Acad Sci USA and was also created in our laboratory by crossing three different T-DNA knock out lines available from SALK (see also WO2010121818).

Figure 5:
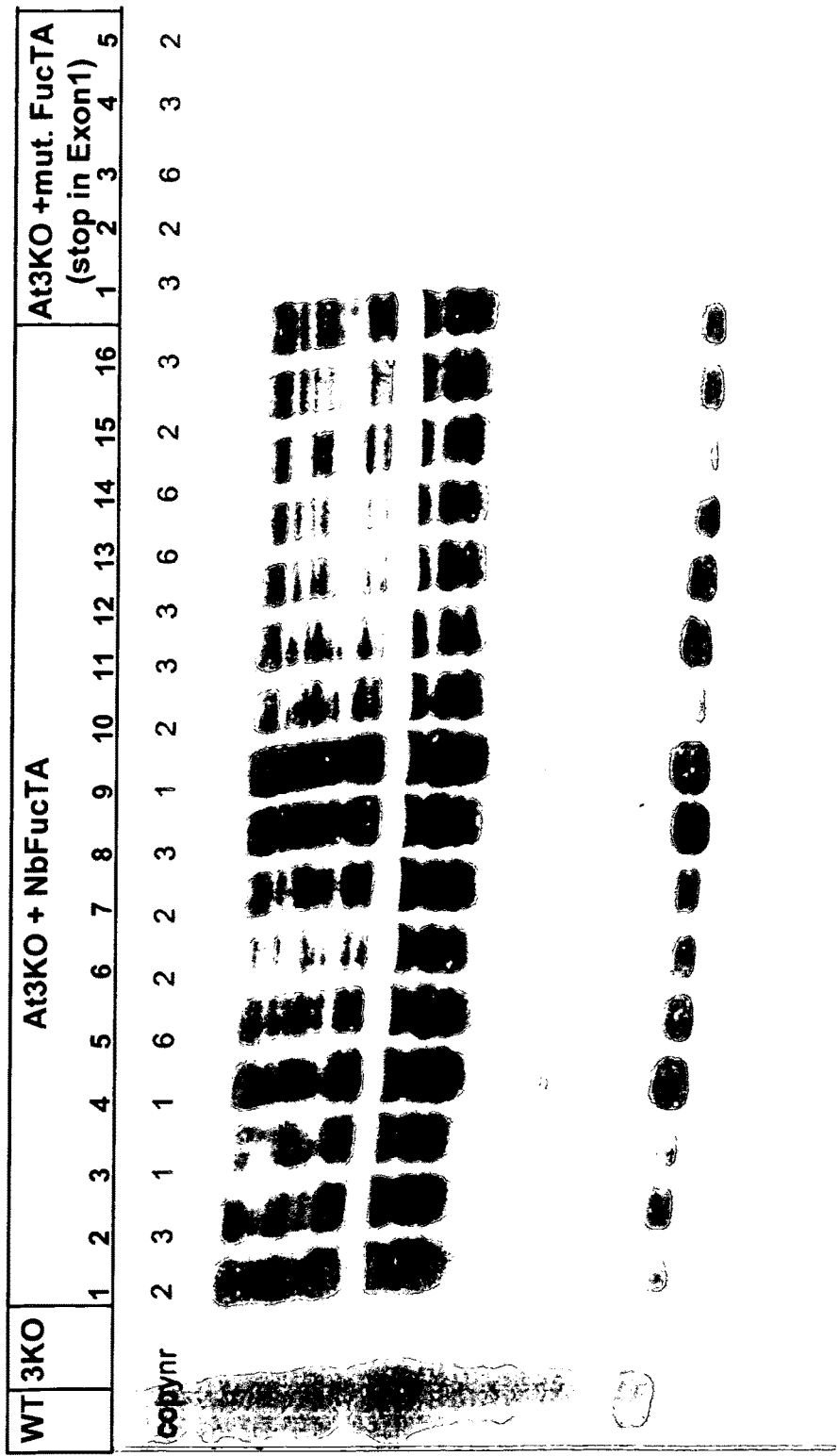
FIG. 5: Setting up and testing the complementation assay for functionality of *N. benthamiana* FucT genes and mutant genes. WT: *A. thaliana* wildtype; 3KO: *A. thaliana* triple mutant (T-DNA-insertion knock-out mutant for XylT and FucTA and FucTB); At3KO+NbFucTA: triple mutant transformed with T-DNA carrying *N. benthamiana* FucTA cDNA; At3KO+mut FucTA: triple mutant transformed with T-DNA carrying *N. benthamiana* FucTA cDNA carrying a point mutation creating a stop codon in exon 1 at position 217 of SEQ ID No. 1.

To set up the system, we first tested whether the *Arabidopsis* triple mutant could be complemented with any one of the *N. benthamiana* FucT genes. We transformed the *Arabidopsis* triple mutant, using the *Agrobacterium* dipping method, with a T-DNA containing the cDNA sequence of one of the FucT genes driven by the CaMV 35S promoter. The cDNA sequence was produced synthetically based on the predicted coding sequence and intron-exon boundaries of the genes. After selection of the transformants using basta (glufosinate), protein samples from leaf tissue were analyzed for the presence of glycans containing core α1,3 fucose using a western blot probed with an anti-core α1,3 fucose antibody. This antibody was prepared as described by Faye et al. (1993) Anal Biochem 209:104. In FIG. 5 (left panel) the results show that the *A. thaliana* triple mutant can be complemented by the *N. benthamiana* FucTA cDNA. The wt control lane shows a clear chemoluminescence signal, produced by binding of the antibody to core α1,3 fucoses. No chemoluminescence signal was detected in the lanes containing protein sample from *A. thaliana* triple mutant. This was caused by absence of core α1,3 fucoses as a result of inactivation of the endogenous FucT genes. By contrast, a clear signal could be detected in the lanes containing protein from several different individual triple mutants transformed with the FucTA cDNA. Together, this shows that the complementation assay can be used to determine whether the *N. benthamiana* FucT genes are active.

Using this assay, we have shown that all genes except for FucTB and FucTE are able to complement and, therefore, represent active genes (data not shown). The fact that FucTB was unable to complement and therefore probably represents an inactive gene was unexpected because FucTB is 100% homologous to the FucTA gene except for a premature stop codon removing 41 amino acids from the C-terminal end of the FucT protein. The fact that FucTE probably represents an inactive gene, based on the complementation assay, is in line with the finding that this gene also does not seem to be transcribed in *N. benthamiana* leaves and contains an inactivating Y288D substitution in MOTIFII.

Next, we used this complementation assay to determine whether the putative null mutations, that were isolated from the EMS-mutagenized populations, indeed rendered the respective FucT genes inactive. The right panel of FIG. 5 shows the results of a complementation assay with a FucTA in which an EMS mutation was simulated at the 8th possible stop codon (position 217; see table 3 FucTA gene). From the absence of a chemoluminescence signal in lanes 1 to 5 in the section labeled "At3KO+mut FucTA (stop in Exon1)", it is clear that this mutated version of FucTA cannot complement the triple knock-out mutant. Absence of chemoluminescence was not caused by the fact that the plants were not transformed (see "copy nr" below each of the lanes) nor by the fact the mutated gene was not expressed as determined by real time RT-PCR (data not shown). Therefore, we can conclude that this mutation can be considered a null mutation.

We subsequently applied this complementation analysis to all putative null mutations for the FucTA, -C, and -D genes that we had found in the EMS population. FucTB and -E mutations were not analyzed as their wt genes were not able to complement.

Complementation was investigated first for the splice site mutants that were identified for FucTA (introns 3 and 1; FucT001, -and -004, respectively) and FucTC (intron 2; FucT007) (Table 4). The splice site mutation for FucTD was not analyzed because of the size of the intron (7833 bp). To analyze the FucTA and -C mutations, we transformed the triple knock-out mutants with FucTA or FucTC CDS containing their own intron 3, 1, or 2 and compared the complementation obtained with these genes with the genes containing the splice site mutation. The results showed that, for FucTA, mutant FucT001 does not represent a null mutation, whereas FucT004 very likely represents a null mutation (data not shown). For FucTC, the intron splice site mutation could not be assessed because the triple knock-out plants transformed with the FucTC CDS containing intron 3 did not complement the mutant phenotype. The gene prediction program FGENESH did predict a strongly disruptive effect for the FucTC splice site mutation however.

Based on a next complementation assay, we confirmed that mutant FucT004 (FucTA), FucT010, -011, and -012 (FucTC), and FucT009 (FucTD) were null mutants (data not shown). Because by the time we had all the data from the complementation assay at hand we were already advanced with crossing FucT004, -007, and -009, we continued with those and used the other mutants as back-up mutant FucT. Our crossing strategy was aimed at first achieving a 5-fold knock-out mutant (XYL001, XYL002, FucT004, FucT007, and FucT009) as the most likely strategy to create a full knock out plant. Our second stategy was aimed at creating a 7-fold knock-out by further introducing FucT006 and FucT003 (see generations 4 and 5 in FIG. 4, respectively).

7. Glycan Analysis of the Seven-Fold Knock Out Plant: *N. benthamiana* Plants Homozygous for Null Mutations in all FucT and XylT Genes While producing seven-fold knock out plant, we also generated three- four, and five-fold knock-out plants as by-products of the crossing scheme. We used these plants to assess whether knocking out consecutive FucT genes had an additive effect and thus whether the FucT-B and -E genes indeed are inactive as was suggested from the complementation assay.

Figure 6:
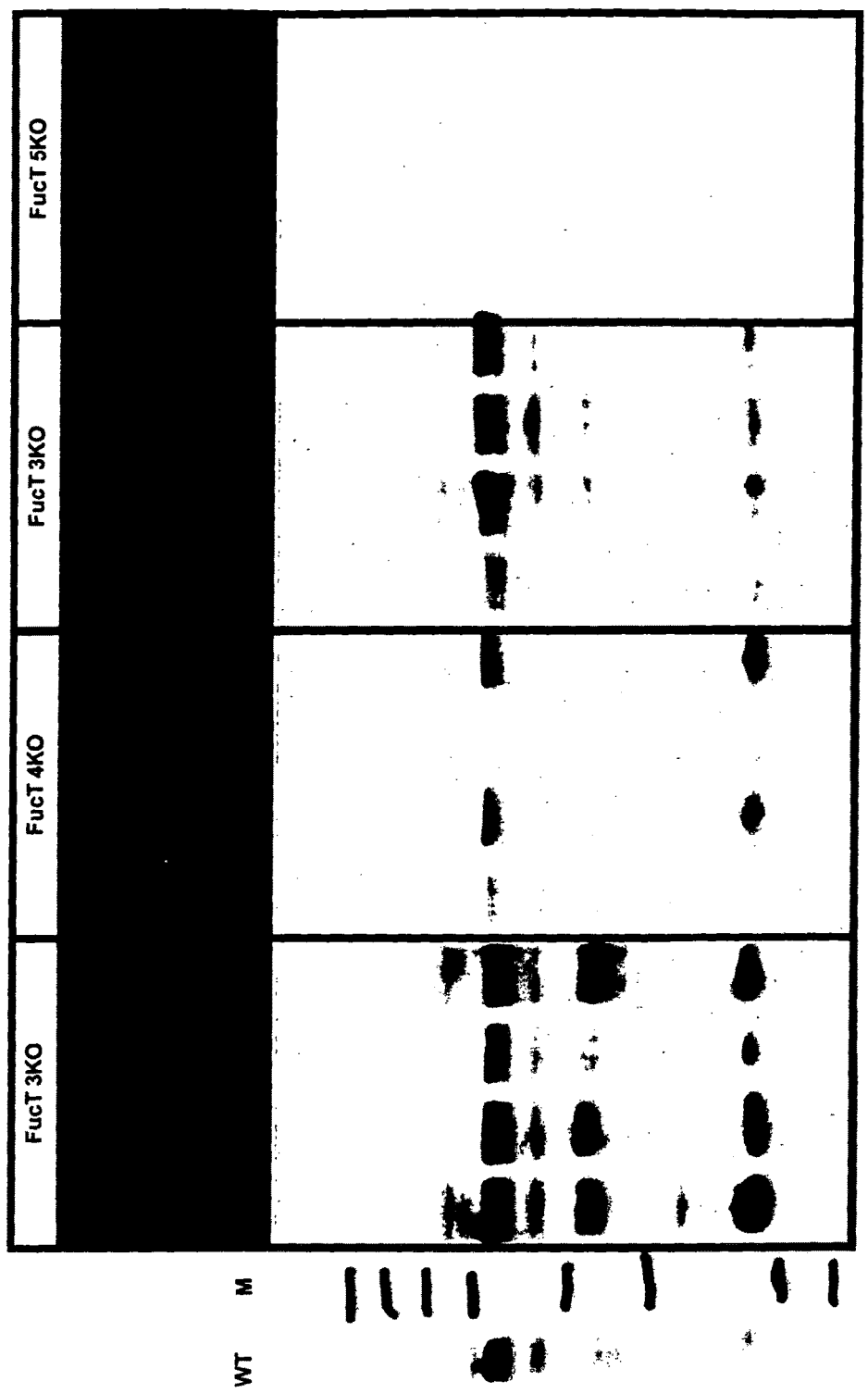
FIG. 6: Comparison of fucosylation levels of protein samples from *N. benthamiana* plants in which different FucT genes have been knocked out. Western blot analysis of leaf protein samples from plants in which different FucT genes have been knocked out. Probed with anti-α1,3 fucose antibody (1/500 dilution); 3 min. exposure for chemoluminescence. WT: Wild Type plant; M: Protein Marker. Knocked-out versions of the gene are indicated in the table as lower case; wild type version as upper case.

FIG. 6 clearly shows that knocking out more FucT genes progressively removes core α1,3 Fucosyltransferase activity from the mutant plants as indicated by the decreasing chemoluminescence signal from the bound anti-α1,3 fucose antibody. This result indicates that probably the FucTB and -E genes still have some fucosyltransferase activity although this was not detected (i.e. compare lanes "aBcdE" versus "abcdE" and compare lanes "abcdE" versus "abcde").

Seeds of the plants in which the 5 FucT genes FucTA, FucTB, FucTC, FucTD and FucTE are knocked out, containing knock-out alleles FucT004, FucT006, FucT007, FucT009, and FucT003, have been deposited at the National Collection of Industrial, Marine and Food Bacteria (NCIMB), NCIMB Ltd, Ferguson Building, Craibstone Estate, Bucksburn, Aberdeen AB219YA, Scotland, on 12 Sep. 2011, under accession number NCIMB 41860 by Bayer BioScience NV, Technologiepark 38, BE-9052 Gent, Belgium. The depositor Bayer BioScience NV, assignor of this invention to the applicant, has merged with and into Bayer CropScience NV having its registered office at J. E. Mommaertslaan 14, 1831 Diegem, Belgium.

Figure 7:
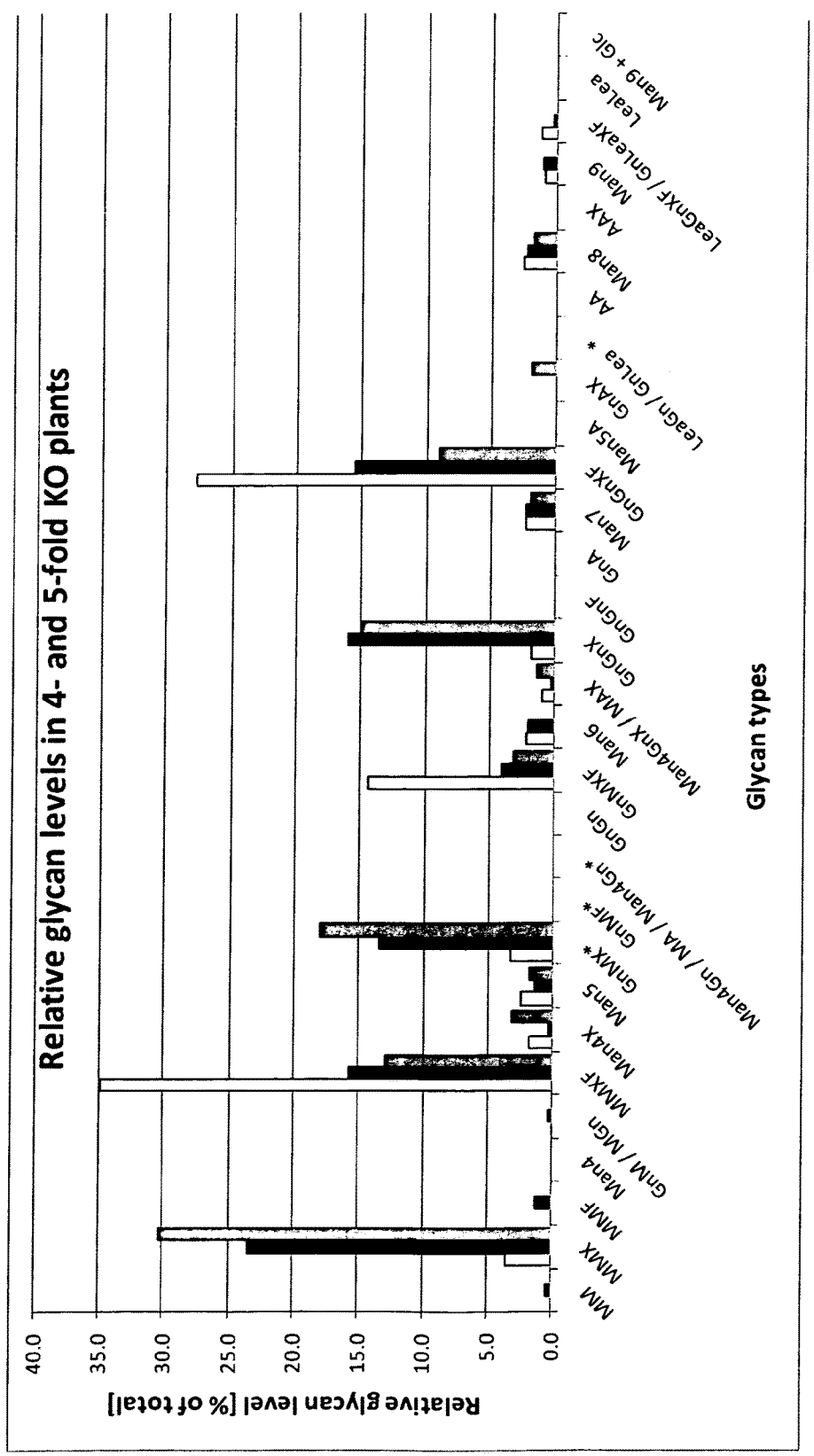
FIG. 7: Comparison of relative glycan levels on leaf proteins from *N. benthamiana* plants carrying null mutations for four or five FucT genes. Total protein was isolated from leaves of plants in which different FucT genes were mutated. Glycans were isolated and analyzed by MALDI-TOF. Relative levels are expressed as percentage of the total peak area as determined from the MALDI-TOF spectra. White bars: wild-type; Black bars: 4KO: FucTA (FucT004), -B (FucT006), -C (FucT007), and -D (FucT009) knocked out (average of three lines); Gray bars: 5KO: all FucT genes knocked out (FucT004, -006, -007, -009, and -003) (average of three lines).

In order to determine which specific glycan levels were reduced and also to determine what types of glycans were present in the four-fold ("abcdE") and five-fold plants ("abcde"), we performed a MALDI-TOF analysis on glycans isolated from total soluble endogenous proteins from leaves of above-mentioned plants. Results are summarized in Table 5 and shown in FIG. 7.

When comparing the glycans in WT and 4- and 5-fold KO plants it is clear that the levels of the fucose-containing glycans are sharply reduced albeit not completely eliminated. By contrast the levels of glycans carrying xylose only (i.e not carrying fucose) are sharply increased. Similar results have been reported by Strasser et al. for FucT knock outs in A. thaliana (Strasser et al. 2004, FEBS Lett 561:132).

Figure 8:
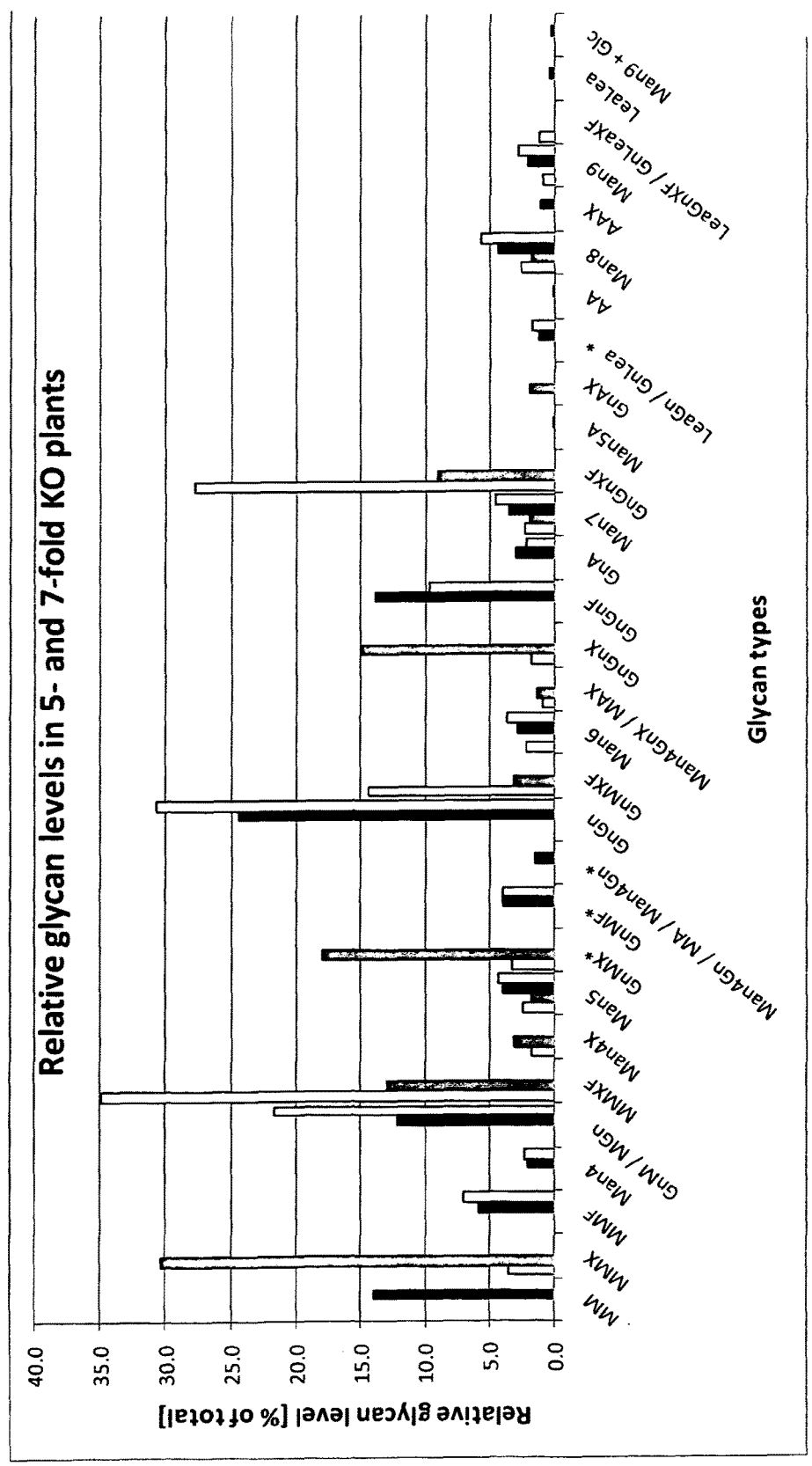
FIG. 8: Comparison of relative glycan levels on leaf proteins from *N. benthamiana* plants in which all XylT and/or FucT genes have been knocked out (FucT004, -006, -007, -009, and -003, and XylTg14-1 and XylTg19-1 as described in WO2010145846). Total protein was isolated from leaves of plants in which all XylT and/or FucT genes were mutated. Glycans were isolated and analyzed by MALDI-TOF. Relative levels are expressed as percentage of the total peak area as determined from the MALDI-TOF spectra. White bars: wild-type. Dark gray bars: 5KO: all FucT genes knocked out (average of three lines); Black bars: 7KO: all FucT and XylT genes knocked out (average of three lines); Light gray bars: RNAi: plants expressing XylT and FucT RNAi genes (Strasser et al. 2008, Plant Biotech J 6:392).

Finally, we have analyzed the glycan quantity and quality in the full knock-out plants (7KO) in which all FucT and XylT genes were mutated and knocked out. Results are summarized in Table 5 and FIG. 8.

Comparing the WT plants with the 5KO and 7KO plants, a strong reduction in all glycans that contain either fucose, xylose or both is observed. When comparing the 5KO and 7KO plants, it is clear that all xylose containing glycans have disappeared from the 7KO spectrum as was to be expected from our previous results on the double XylT knock-out plants (WO2010145846). Also, it seems that the bars representing glycans that contained both xylose and fucose in the 5KO plants had shifted to glycans carrying only fucoses (for instance, compare MMXF and MMF; GnMXF and GnMF; GnGnXF and GnGnF). Finally, when comparing the glycans obtained from 7KO plants with the glycans obtained from plants expressing the XylT- and FucT RNAi genes (Strasser et al. 2008, Plant Biotech J 6:392), the spectra are almost identical. Notable differences are a strong presence of MM glycans in the 7KO plants which are absent in the RNAi plants similar, albeit to a lesser extent, for the Man4Gn glycan. Also, the 7KO plants have a higher level of GnGnF glycans as compared to RNAi and, vice versa, the RNAi plants have a higher level of GnM and GnGn glycans.

TABLE 5

Relative glycan levels on endogenous soluble leaf proteins from N. benthamiana plants in which Xylosyl- and/or Fucosyltransferase activity has been reduced by gene mutation or RNAi. Total protein was isolated from leaves of plants in which different XylT and/or FucT genes were mutated or in which XylT and FucT RNAi genes were expressed. Glycans were isolated and analyzed by MALDI-TOF. Relative levels are expressed as percentage of the total peak area as determined from the MALDI-TOF spectra. 4KO-: FucTA (FucT004), -B (FucT006), -C (FucT007), and -D (FucT009) knocked out; 5KO-: all FucT genes knocked out (FucT004, -006, -007, -009, and -003); 7KO-: all FucT and XylT genes knocked out (FucT004, -006, -007, -009, and -003, and XylTg14-1 and XylTg19-1 as described in WO2010145846); WT: Wild Type; RNAi: plants expressing XylT and FucT RNAi genes (Strasser et al. 2008, Plant Biotech J 6: 392).

|  | 4KO | | | 5KO | | | 7KO | | | WT | RNAi |
|---|---|---|---|---|---|---|---|---|---|---|---|
|  | 4KO-0447 | 4KO-0660 | 4KO-0772 | 5KO-0023 | 5KO-0044 | 5KO-0046 | 7KO-0095 | 7KO-0910 | 7KO-0925 | WT | RNAi |
| MM | 0.0 | 0.0 | 1.4 | 0.0 | 0.0 | 0.0 | 16.3 | 13.4 | 12.2 | 0.0 | 0.0 |
| MMX | 27.9 | 21.2 | 21.4 | 0.0 | 41.5 | 49.5 | 0.0 | 0.0 | 0.0 | 3.5 | 0.0 |
| MMF | 1.4 | 0.9 | 1.3 | 0.0 | 0.0 | 0.0 | 5.8 | 5.1 | 6.5 | 0.0 | 7.0 |
| Man4 | 0.0 | 0.0 | 0.0 | 0.0 | 0.0 | 0.0 | 2.3 | 2.0 | 1.7 | 0.0 | 2.2 |
| GnM/MGn | 0.0 | 0.0 | 0.8 | 0.0 | 0.0 | 0.0 | 13.3 | 11.6 | 11.4 | 0.0 | 21.6 |
| MMXF | 13.6 | 18.5 | 15.0 | 14.7 | 10.7 | 13.4 | 0.0 | 0.0 | 0.0 | 34.8 | 0.0 |
| Man4X | 0.0 | 1.0 | 0.0 | 3.9 | 2.0 | 3.2 | 0.0 | 0.0 | 0.0 | 1.8 | 0.0 |
| Man5 | 0.0 | 2.0 | 2.0 | 1.9 | 1.8 | 1.6 | 4.0 | 4.3 | 3.2 | 2.4 | 4.3 |
| GnMX* | 15.4 | 10.6 | 14.1 | 25.0 | 15.9 | 13.0 | 0.0 | 0.0 | 0.0 | 3.2 | 0.0 |
| GnMF* | 0.0 | 0.0 | 0.0 | 0.0 | 0.0 | 0.0 | 3.5 | 3.4 | 4.7 | 0.0 | 3.9 |
| Man4Gn/MA/Man4Gn* | 0.0 | 0.0 | 0.0 | 0.0 | 0.0 | 0.0 | 1.3 | 1.5 | 1.5 | 0.0 | 0.0 |
| GnGn | 0.0 | 0.0 | 0.0 | 0.0 | 0.0 | 0.0 | 25.0 | 25.2 | 23.0 | 0.0 | 30.8 |
| GnMXF | 3.6 | 4.0 | 4.3 | 4.8 | 2.6 | 2.0 | 0.0 | 0.0 | 0.0 | 14.3 | 0.0 |
| Man6 | 1.5 | 2.6 | 1.9 | 0.0 | 0.0 | 0.0 | 2.9 | 2.8 | 2.9 | 2.1 | 3.6 |
| Man4GnX/MAX | 0.0 | 0.0 | 0.9 | 3.0 | 1.2 | 0.0 | 0.0 | 0.0 | 0.0 | 0.9 | 0.0 |
| GnGnX | 19.1 | 12.5 | 16.5 | 21.8 | 12.7 | 10.0 | 0.0 | 0.0 | 0.0 | 1.7 | 0.0 |
| GnGnF | 0.0 | 0.0 | 0.0 | 0.0 | 0.0 | 0.0 | 12.1 | 12.7 | 16.7 | 0.0 | 9.7 |
| GnA | 0.0 | 0.0 | 0.0 | 0.0 | 0.0 | 0.0 | 2.4 | 3.2 | 3.3 | 0.0 | 2.1 |
| Man7 | 2.0 | 3.2 | 1.8 | 3.1 | 1.5 | 1.3 | 3.3 | 3.5 | 3.6 | 2.3 | 4.5 |
| GnGnXF | 12.7 | 18.2 | 15.9 | 14.8 | 6.3 | 6.0 | 0.0 | 0.0 | 0.0 | 27.8 | 0.0 |
| Man5A | 0.0 | 0.0 | 0.0 | 0.0 | 0.0 | 0.0 | 0.5 | 0.0 | 0.0 | 0.0 | 0.0 |
| GnAX | 0.0 | 0.0 | 0.0 | 3.6 | 2.0 | 0.0 | 0.0 | 0.0 | 0.0 | 0.0 | 0.0 |
| LeaGn/GnLea * | 0.0 | 0.0 | 0.0 | 0.0 | 0.0 | 0.0 | 1.1 | 1.3 | 1.3 | 0.0 | 1.8 |
| AA | 0.0 | 0.0 | 0.0 | 0.0 | 0.0 | 0.0 | 0.0 | 0.6 | 0.0 | 0.0 | 0.0 |

TABLE 5-continued

Relative glycan levels on endogenous soluble leaf proteins from *N. benthamiana* plants in which Xylosyl- and/or Fucosyltransferase activity has been reduced by gene mutation or RNAi. Total protein was isolated from leaves of plants in which different XylT and/or FucT genes were mutated or in which XylT and FucT RNAi genes were expressed. Glycans were isolated and analyzed by MALDI-TOF. Relative levels are expressed as percentage of the total peak area as determined from the MALDI-TOF spectra. 4KO-: FucTA (FucT004), -B (FucT006), -C (FucT007), and -D (FucT009) knocked out; 5KO-: all FucT genes knocked out (FucT004, -006, -007, -009, and -003); 7KO-: all FucT and XylT genes knocked out (FucT004, -006, -007, -009, and -003, and XylTg14-1 and XylTg19-1 as described in WO2010145846); WT: Wild Type; RNAi: plants expressing XylT and FucT RNAi genes (Strasser et al. 2008, Plant Biotech J 6: 392).

| | 4KO | | | 5KO | | | 7KO | | | WT | RNAi |
|---|---|---|---|---|---|---|---|---|---|---|---|
| | 4KO-0447 | 4KO-0660 | 4KO-0772 | 5KO-0023 | 5KO-0044 | 5KO-0046 | 7KO-0095 | 7KO-0910 | 7KO-0925 | WT | RNAi |
| Man8 | 1.9 | 3.2 | 1.6 | 3.3 | 1.8 | 0.0 | 3.6 | 4.8 | 4.5 | 2.5 | 5.7 |
| AAX | 0.0 | 0.0 | 0.0 | 0.0 | 0.0 | 0.0 | 0.8 | 1.0 | 1.3 | 0.0 | 0.0 |
| Man9 | 1.0 | 1.2 | 1.1 | 0.0 | 0.0 | 0.0 | 1.6 | 2.2 | 2.2 | 1.0 | 2.8 |
| LeaGnXF/GnLeaXF | 0.0 | 0.9 | 0.0 | 0.0 | 0.0 | 0.0 | 0.0 | 0.0 | 0.0 | 1.2 | 0.0 |
| LeaLea | 0.0 | 0.0 | 0.0 | 0.0 | 0.0 | 0.0 | 0.5 | 0.6 | 0.0 | 0.0 | 0.0 |
| Man9 + Glc | 0.0 | 0.0 | 0.0 | 0.0 | 0.0 | 0.0 | 0.4 | 0.5 | 0.0 | 0.0 | 0.0 |

8. Glycan Analysis of an IgG1 Expressed in the *N. benthamiana* Full Knock-Out Plant Using MapnICON®

Since the glycan quality and quantity on the endogenous proteins of the 7KO plants were comparable those of the plants expressing the XylT- and FucT RNAi genes and since it has been described that IgG1 proteins expressed in the latter plants do not contain glycans carrying xylose or fucoses (i.e. despite the fact that their endogenous proteins do carry fucoses; Nagels et al. 2011, Plant Physiol 155: 1103), we decided to test whether glycans on an IgG1 molecule expressed in the full knock plants would similarly be free of fucose and xylose.

IgG1 was isolated from leaf extract nine days after infiltration using protein G. The heavy chain of the purified antibody was isolated by cutting the corresponding band from a reducing SDS-PAGE. The heavy chain protein in this band was used for glycan analysis by LC-MS as described by Kolarich et al. 2006, Proteomics 6:3369.

Figure 9:
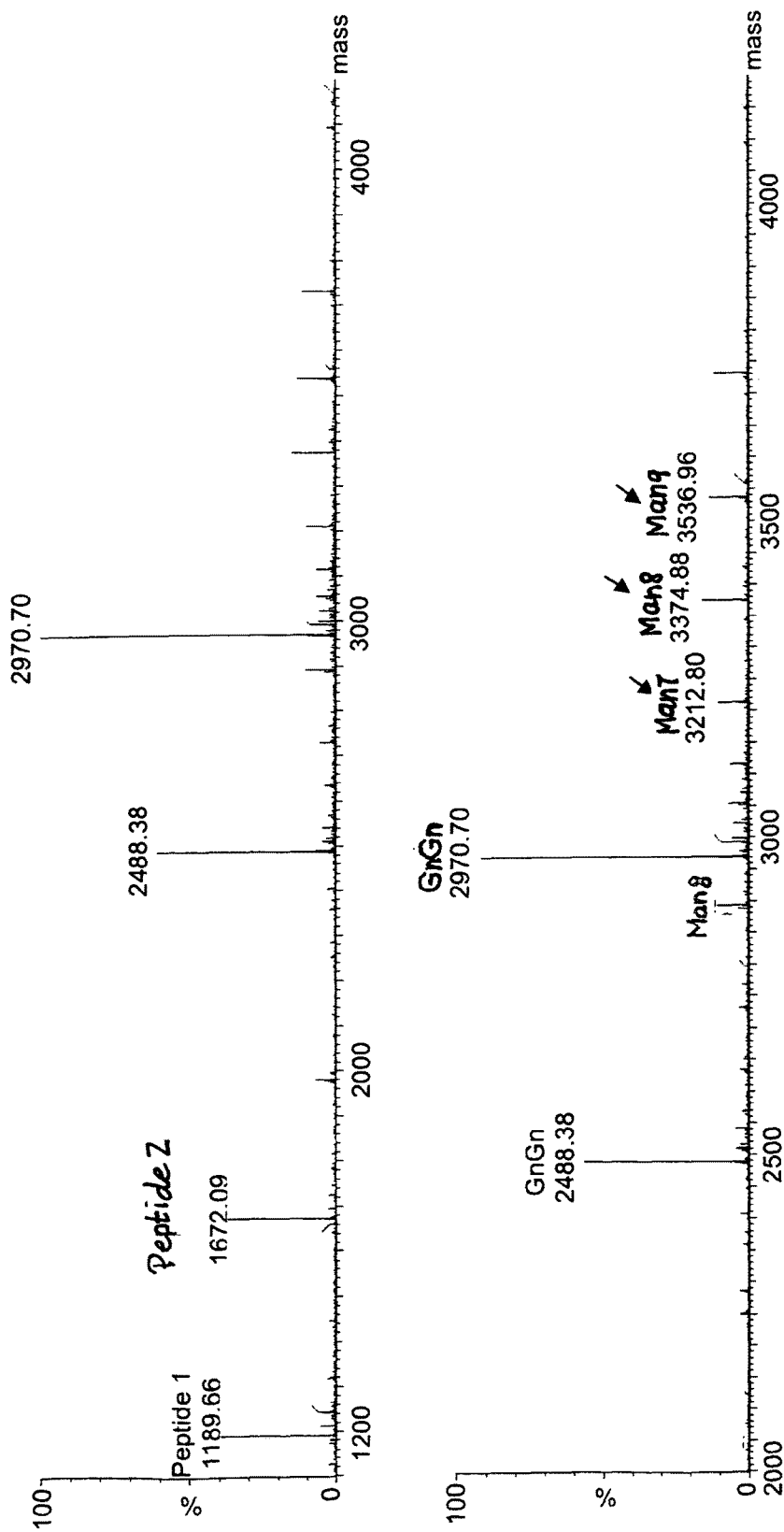
FIG. 9: LC-MS analysis of glycans on an IgG1 expressed in a full knock-out *N. benthamiana* plant using magnICON®.

FIG. 9 shows the resulting spectrum from this analysis. The upper panel shows a wider mass spectrum to illustrate the presence of non-glycosylated peptides. Peptide 1 (EEQYNSTY) (SEQ ID NO:22) and peptide 2 (TKPREEQYNSTYR) (SEQ ID NO:23) are two variants from the same trypsin digestion. They differ in length caused by steric hindrance of the trypsin by the presence of N-glycans. As a result, all peptide-glycans produce two peaks in this LC-MS spectrum: indicated on the lower panel in black for glycopeptide 1 and orange for glycopeptide 2. In the lower panel of FIG. 9, only one major glycan peak can be found for GnGn. In addition, some minor peaks for high mannose glycans are also visible (Man7, 8, and –9). However, in the full summary of all glycopeptides that were identified by LC-MS, listed in Table 6, a small fraction of GnGnF glycans representing 2.6% of the total fraction of glycosylated and non-glycosylated glyco-peptides was identified.

TABLE 6

Relative glycan levels on heavy chain of IgG1 expressed in a *N. benthamiana* full knock out plant. In the full knock-out plant, all FucT and XylT genes are knocked out (FucT004, -006, -007, -009, and -003, and XylTg14-1 and XylTg19-1 as described in WO2010145846). Relative levels are expressed as percentage of the total peak area as determined from the LC-MS spectrum in FIG. 9.

| | Relative glycan level |
|---|---|
| non-glyc peptide | 19.8 |
| MGn | 2.3 |
| GnGn | 51.7 |
| GnGnF | 2.6 |
| GnA | 0.9 |
| AA | 0.2 |
| Man5 | 0.7 |
| Man7 | 6.0 |
| Man8 | 8.6 |
| Man9 | 7.2 |

Combining the Seven-Fold Knock Out Plant with a FucT RNAi Gene Further Reduces the Fucose Levels on N-Glycans In an attempt to further decrease the amount of residual Fucose residues on the N-glycans in the seven-fold knock out plants, we introduced a FucT RNAi gene in these plants by crossing these plants with plants containing the FucT RNAi gene from pGAX3 (WO 2009/056155). Homozygosity of the seven knock-out genes as well as the FucT RNAi gene was confirmed by End Point Taqman assays. Endogenous proteins from these plants (i.e. 7KO/FucT RNAi) were analyzed by Western blot and by MALDI-TOF analysis.

Results from the Western blot analysis in FIG. 11 clearly show that adding the FucT RNAi gene to the seven-fold knock out plants further removes core α1,3 Fucose residues from the N-glycans as indicated by the complete absence of chemoluminescence signal from the lanes containing proteins from the 7KO/FucT RNAi plants as compared to lanes containing proteins from plants in which 6 or 7 genes have been knocked out. Even after a prolonged exposure of 1 hour, no signal could be detected in 7KO/FucT RNAi lanes.

In order to determine specific glycan levels, MALDI-TOF analysis on glycans isolated from total soluble endogenous proteins from leaves of 7KO/FucT RNAi plants was performed. When comparing the glycans of the 7KO/FucT RNAi plants with WT, 4-, 5- and 7-fold KO plants, it is clear that the levels of the fucose-containing glycans are further reduced to only trace amounts of MMF, GnGnF and GnAF (LeaGn) glycans. As was the case for the 7KO plants, xylosylated N-glycans have completely disappeared in the 7KO/FucT RNAi plants (as shown in table 7)

TABLE 7

Relative glycan levels on endogenous soluble leaf proteins from *N. benthamiana* 7KO/FucT RNAi plants. Total protein was isolated from leaves of plants in which all XylT and FucT genes were mutated and in which a FucT RNAi gene was expressed. Glycans were isolated and analyzed by MALDI-TOF. Relative levels are expressed as percentage of the total peak area as determined from the MALDI-TOF spectra. Fucosylated N-glycans in shadow.

|  | 7KO/FucT RNAi | | | |
|---|---|---|---|---|
|  | 7KO-1679 | 7KO-2125 | 7KO-2264 | 7KO-2512 |
| MM | 24.93 | 41.72 | 31.98 | 26.95 |
| MMX | 0.00 | 0.00 | 0.00 | 0.00 |
| MMF | 0.00 | 0.00 | 0.77 | 0.00 |
| Man4 | 0.00 | 0.00 | 0.55 | 0.00 |
| GnM/MGn | 13.58 | 14.64 | 14.59 | 16.16 |
| MMXF | 0.00 | 0.00 | 0.00 | 0.00 |
| Man4X | 0.00 | 0.00 | 0.00 | 0.00 |
| Man4F | 0.00 | 0.00 | 0.00 | 0.00 |
| Man5 | 1.27 | 2.81 | 2.68 | 1.73 |
| GnMX | 0.00 | 0.00 | 0.00 | 0.00 |
| GnMF | 0.00 | 0.00 | 0.00 | 0.00 |
| Man4Gn/MA/Man4Gn | 0.00 | 0.00 | 0.00 | 0.00 |
| GnGn | 44.03 | 33.60 | 36.05 | 40.06 |
| Man4XF | 0.00 | 0.00 | 0.00 | 0.00 |
| Man5X | 0.00 | 0.00 | 0.00 | 0.00 |
| Man5F | 0.00 | 0.00 | 0.00 | 0.00 |
| GnMXF | 0.00 | 0.00 | 0.00 | 0.00 |
| Man6 | 1.34 | 1.60 | 2.15 | 1.63 |
| Man4GnX/MAX | 0.00 | 0.00 | 0.00 | 0.00 |
| Man4GnF/MAF | 0.00 | 0.00 | 0.00 | 0.00 |
| Man5Gn/Man4A | 0.00 | 0.00 | 0.00 | 0.00 |
| GnGnX | 0.00 | 0.00 | 0.00 | 0.00 |
| GnGnF | 0.83 | 0.60 | 0.91 | 0.72 |
| GnA | 0.00 | 0.00 | 0.00 | 0.00 |
| Man5XF | 0.00 | 0.00 | 0.00 | 0.00 |
| GnGnGn | 0.00 | 0.00 | 0.00 | 0.00 |
| Man4GnXF/MAXF | 0.00 | 0.00 | 0.00 | 0.00 |
| Man7 | 2.33 | 1.79 | 2.99 | 2.17 |
| Man5GnX/Man4AX | 0.00 | 0.00 | 0.00 | 0.00 |
| Man5GnF/Man4AF | 0.00 | 0.00 | 0.00 | 0.00 |
| GnGnXF | 0.00 | 0.00 | 0.00 | 0.00 |
| Man5A | 0.00 | 0.00 | 0.00 | 0.00 |
| GnAX | 0.00 | 0.00 | 0.00 | 0.00 |
| GnAF/(LeaGn) | 0.83 | 0.50 | 0.94 | 0.60 |
| AA | 0.00 | 0.00 | 0.00 | 0.00 |
| GnGnGnX | 0.00 | 0.00 | 0.00 | 0.00 |
| GnGnGnF | 0.00 | 0.00 | 0.00 | 0.00 |
| GnGnA | 0.00 | 0.00 | 0.00 | 0.00 |
| Man5GnXF/Man4AXF | 0.00 | 0.00 | 0.00 | 0.00 |
| Man8 | 3.62 | 2.65 | 2.90 | 2.79 |
| GnGnGnGn | 0.00 | 0.00 | 0.00 | 0.00 |
| Man5AX | 0.00 | 0.00 | 0.00 | 0.00 |
| Man5AF | 0.00 | 0.00 | 0.00 | 0.00 |
| GnAXF | 0.00 | 0.00 | 0.00 | 0.00 |
| (AF)GnF | 0.00 | 0.00 | 0.00 | 0.00 |
| AAX | 0.00 | 0.00 | 0.00 | 0.00 |
| AAF | 0.00 | 0.00 | 0.00 | 0.00 |
| GnGnGnXF | 0.00 | 0.00 | 0.00 | 0.00 |
| AA + Hex | 0.00 | 0.00 | 0.00 | 0.00 |
| GnGnAX | 0.00 | 0.00 | 0.00 | 0.00 |
| GnGnAF | 0.00 | 0.00 | 0.00 | 0.00 |
| GnAA | 0.00 | 0.00 | 0.00 | 0.00 |
| GnGnGnGnX | 0.00 | 0.00 | 0.00 | 0.00 |
| GnGnGnGnF | 0.00 | 0.00 | 0.00 | 0.00 |
| Man5AXF | 0.00 | 0.00 | 0.00 | 0.00 |
| Man9 | 6.68 | 0.70 | 3.49 | 6.37 |

TABLE 7-continued

Relative glycan levels on endogenous soluble leaf proteins from *N. benthamiana* 7KO/FucT RNAi plants. Total protein was isolated from leaves of plants in which all XylT and FucT genes were mutated and in which a FucT RNAi gene was expressed. Glycans were isolated and analyzed by MALDI-TOF. Relative levels are expressed as percentage of the total peak area as determined from the MALDI-TOF spectra. Fucosylated N-glycans in shadow.

|  | 7KO/FucT RNAi | | | |
|---|---|---|---|---|
|  | 7KO-1679 | 7KO-2125 | 7KO-2264 | 7KO-2512 |
| GnGnGnA | 0.00 | 0.00 | 0.00 | 0.00 |
| LeaGnXF/GnLeaXF | 0.00 | 0.00 | 0.00 | 0.00 |
| AAXF | 0.00 | 0.00 | 0.00 | 0.00 |
| (AAF)F/LeaLea | 0.00 | 0.00 | 0.00 | 0.00 |
| AAX + Hex | 0.00 | 0.00 | 0.00 | 0.00 |
| AAF + Hex | 0.00 | 0.00 | 0.00 | 0.00 |
| GnGnAXF | 0.00 | 0.00 | 0.00 | 0.00 |
| AA + 2 Hex | 0.00 | 0.00 | 0.00 | 0.00 |
| GnAAX | 0.00 | 0.00 | 0.00 | 0.00 |
| GnAAF | 0.00 | 0.00 | 0.00 | 0.00 |
| GnGnGnXF | 0.00 | 0.00 | 0.00 | 0.00 |
| GnGnGnAX | 0.00 | 0.00 | 0.00 | 0.00 |
| GnGnGnAF | 0.00 | 0.00 | 0.00 | 0.00 |
| Man9 + Glc | 0.55 | 0.00 | 0.00 | 0.00 |
| GnGnAA | 0.00 | 0.00 | 0.00 | 0.80 |
| A(AF)XF | 0.00 | 0.00 | 0.00 | 0.00 |
| (AF)(AF)F | 0.00 | 0.00 | 0.00 | 0.00 |
| AAXF + Hex | 0.00 | 0.00 | 0.00 | 0.00 |
| GnAAXF | 0.00 | 0.00 | 0.00 | 0.00 |
| GnGnGnAXF | 0.00 | 0.00 | 0.00 | 0.00 |
| GnGnAAX | 0.00 | 0.00 | 0.00 | 0.00 |
| GnGnAAF | 0.00 | 0.00 | 0.00 | 0.00 |
| Man9 + 2Glc | 0.00 | 0.00 | 0.00 | 0.00 |
| GnAAA | 0.00 | 0.00 | 0.00 | 0.00 |
| LeaLeaXF | 0.00 | 0.00 | 0.00 | 0.00 |
| GnGnAAXF | 0.00 | 0.00 | 0.00 | 0.00 |
| GnAAAX | 0.00 | 0.00 | 0.00 | 0.00 |
| GnAAAF | 0.00 | 0.00 | 0.00 | 0.00 |
| AAAA | 0.00 | 0.00 | 0.00 | 0.00 |
| GnAAAXF | 0.00 | 0.00 | 0.00 | 0.00 |
| AAAAX | 0.00 | 0.00 | 0.00 | 0.00 |
| AAAAF | 0.00 | 0.00 | 0.00 | 0.00 |
| AAAXF | 0.00 | 0.00 | 0.00 | 0.00 |

FIG. 12 shows a quantitative overview of fucosylated resp. xylosylated N-glycans present on the endogenous proteins of WT, 4-, 5-, 7-fold KO, RNAi and 7KO/FucT RNAi plants.

Introducing a FucT RNAi Gene into the Seven-Fold Knock Out Plants to Further Reduce Fucose Levels on N-Glycans.

In order to further reduce the fucose levels on N-glycans in seven-fold knock-out plants, RNAi genes are constructed that target silencing of all FucT genes by including multiple stretches of 25 or more nucleotides that are 100% homologous to two or more FucT genes and, combined, target all FucT genes. For example, a fragment of the FucTB coding sequence (Seq ID No 5) from nucleotide 1183 to 1265 (Seq ID No 20) contains a stretch of 44 nucleotides, from 1183 to 1226, that is 100% homologous to FucT-B, -C, -D, and -E and a fragment of 47 nucleotides, from 1219 to 1265, that is 100% homologous to FucT-A, and -B. This fragment (Seq ID No 20) is assembled into an RNAi gene as shown in Seq ID No 21. Expression of the RNAi gene is driven by the 35S promoter by cloning it into a T-DNA vector similar to pGAX3 (WO 2009/056155). The seven-fold knock-out *N. benthamiana* plants are transformed with this construct and analyzed for N-glycan composition on endogenous proteins and on heterologously magnICON®-expressed proteins like, for instance, an IgG1 molecule.

In addition, the FucT RNAi gene is cloned in a promoterless T-DNA vector similar to pICH3781 and pICH3831 (WO 02/101060) where the existing BAR gene is replaced by the FucT RNAi gene fragment. The seven-fold knock-out *N. benthamiana* plants are transformed with these constructs. Use of promoterless vectors will provide a broader choice of primary transformants in comparison to vectors with strong constitutive promoter. In such case the RNAi becomes part of a transcriptional fusion with a residential gene (the promoterless vector contains splice acceptor sites in front of the RNAi gene). This can be an advantage, as the RNAi usually targets multigene family and this might compromise plant phenotype—growth, development, abiotic or biotic stress resistance, etc. The resulting stably transformed plants are screened for absence of fucoses on the N-glycans of their endogenous proteins and of heterologously magniCON®-expressed proteins like, for instance, an IgG1 molecule. Those selected can be additionally screened for their performance in glasshouses, e.g. vegetative growth efficiency in comparison with wild type plants.

The content of U.S. patent application 61/542,965 filed on Oct. 4, 2011 and European patent application No. 11 075 218.5 filed on Oct. 6, 2011 the priorities of which are claimed by the present patent application are herewith incorporated by reference in their entirety including descriptions, all claims, all figures and SEQ ID NOs 1 to 19 of the sequence listing.

The invention claimed is:

1. A *Nicotiana benthamiana* plant, cell, part, seed, or progeny thereof, comprising at least three knock-out alfa(1,3)-fucosyltransferase genes, wherein one or more of the knock-out alfa(1,3)-fucosyltransferase genes is a mutated version of a native alfa(1,3)-fucosyltransferase gene selected from the group consisting of:
   a. FucTA gene containing a G to A substitution at position 355 of SEQ ID NO: 1;
   b. FucTB gene containing a G to A substitution at position 3054 of SEQ ID NO: 4;
   c. FucTC gene containing a G to A substitution at position 2807 of SEQ ID NO: 7;
   d. FucTD gene containing a G to A substitution at position 224 of SEQ ID NO: 10; and
   e. FucTE gene containing a G to A substitution at position 910 of SEQ ID NO: 13.

2. The plant, cell, part, seed, or progeny according to claim 1, comprising at least five knock-out alfa(1,3)-fucosyltransferase genes.

3. The plant, cell, part, seed, or progeny according to claim 1 which is homozygous for the knock-out alfa(1,3)-fucosyltransferase genes.

4. The plant, cell, part, seed, or progeny according to claim 1, further comprising at least one knock-out beta(1,2)-xylosyltransferase gene, wherein said knock-out beta(1,2)-xylosyltransferase gene comprises a mutated DNA region consisting of one or more inserted, deleted or substituted nucleotides compared to a corresponding wild-type DNA region in the beta(1,2)-xylosyltransferase gene and wherein said knock-out beta(1,2)-xylosyltransferase gene does not encode a functional beta(1,2)-xylosyltransferase protein.

5. The plant, cell, part, seed, or progeny according to claim 1, further comprising at least one chimeric gene comprising the following operably linked DNA fragments:
   a. a plant-expressible promoter;
   b. a DNA region, which when transcribed yields an RNA molecule inhibitory to at least one alfa(1,3)-fucosyltransferase encoding gene; and
   c. a DNA region comprising a transcription termination and polyadenylation signal functional in plants.

6. The plant, cell, part, seed, or progeny according to claim 5, wherein said DNA region comprises the sequence of SEQ ID NO: 19.

7. The plant, cell, part, seed, or progeny according to claim 1, further comprising a glycoprotein foreign to said plant or plant cell.

8. The plant, cell, part, seed, or progeny according to claim 7, wherein said glycoprotein is expressed from a chimeric gene comprising the following operably linked nucleic acid molecules:
   a. a plant-expressible promoter;
   b. a DNA region encoding said heterologous glycoprotein; and
   c. a DNA region involved in transcription termination and polyadenylation.

* * * * *

SEQUENCE LISTING

```
<160> NUMBER OF SEQ ID NOS: 23

<210> SEQ ID NO 1
<211> LENGTH: 6339
<212> TYPE: DNA
<213> ORGANISM: Nicotiana benthamiana
<220> FEATURE:
<221> NAME/KEY: Exon1
<222> LOCATION: (1)..(354)
<220> FEATURE:
<221> NAME/KEY: Variation
<222> LOCATION: (355)..(355)
<223> OTHER INFORMATION: G to A substitution in FucT004
<220> FEATURE:
<221> NAME/KEY: Intron1
<222> LOCATION: (355)..(1097)
<220> FEATURE:
<221> NAME/KEY: Exon2
<222> LOCATION: (1098)..(1258)
<220> FEATURE:
<221> NAME/KEY: Intron2
<222> LOCATION: (1259)..(2832)
<220> FEATURE:
<221> NAME/KEY: Exon3
<222> LOCATION: (2833)..(3074)
<220> FEATURE:
<221> NAME/KEY: Intron3
<222> LOCATION: (3075)..(3647)
<220> FEATURE:
<221> NAME/KEY: Exon4
<222> LOCATION: (3648)..(3752)
<220> FEATURE:
<221> NAME/KEY: Intron4
<222> LOCATION: (3753)..(4265)
<220> FEATURE:
<221> NAME/KEY: Exon5
<222> LOCATION: (4266)..(4422)
<220> FEATURE:
<221> NAME/KEY: Intron5
<222> LOCATION: (4423)..(4846)
<220> FEATURE:
<221> NAME/KEY: Exon6
<222> LOCATION: (4847)..(5074)
<220> FEATURE:
<221> NAME/KEY: Intron6
<222> LOCATION: (5075)..(6083)
<220> FEATURE:
<221> NAME/KEY: Exon7
<222> LOCATION: (6084)..(6339)

<400> SEQUENCE: 1
atgagatcgg cgtcaaattc aaacgcaccc aataagcaat ggcgcaattg gttgcctctg      60
ttcgttgccc tagtgattat agctgagttt tcttttctgg ttcgactcga cgtagctgaa     120
aaagccaact cttgggccga atcgttttat cagttcacca cggcctcttg gtccacctct     180
aaactggctg ttgaccacgg cgacgttgag gaggtccagt tgggtgtttt gagtggtgag     240
ttcgatcatg gcttcgtacc tgggagttgc gaggagtggt tggaaaggga agattctgtg     300
```

```
gcttattcga gggatttttga taatgaacca attttttgttc atgggcctgg acaggttata    360
tccacttcta tttattagtg aatatatata attggattta ctagtttgcc attgagtcat    420
actcgtattt cttttttttgg atcgttgtta gtgatatgcc taaatttctt tataatgtat    480
ttgtttaatt ttgtcgattt tatcgcaatt cctagtgtta gataatcctt aaatacgtgg    540
tattgaatta ttatggactc agacagagca tttatgatat tgagaattca tgcagccgac    600
tccaactagt ttgggataga ggcgtagtag tagtagttgt ttttgttgtc ggaaaaaatg    660
tattggcatc tcagtacact ttaggtgcat ggttgatttc agtctttttgg tattattgta    720
gctggctcat agcaagagag gtttgcttag ttgatggatt tttgttttttt agcttcattt    780
gctgtgagat attaataagg attagagttt ctaatccttt tatttaaaag tggggaaaga    840
gtagggaaac tttgtgaatt ttcatattga tttgcctttt gaagcatata ttcattcagc    900
gttcctttat ttatttcatc acaaaaaata atactctaat ggaatgatca gaaatcaatt    960
tatcataatg caaatgccac ttcttattgt tcttggtctc ccatgctatg cgcttgttac   1020
atattcccta ctcatctctg actttatgaa tgtcccatca tatacggaat tctgatgtct   1080
attcaatcac tatacaggaa ttgaaatctt gttccatagg atgtaagttt ggaacagatt   1140
ccaataagaa gcctgatgca gcatttcggc taccacaaca agctggcaca gctagtgtgc   1200
tacggtcgat ggagtcagct caatactatg cagagaacaa cattactttg gcacgacggt   1260
gggtaagcac actgtgaaag aagtcttatt tcattccctg cctttattgg caattttctt   1320
ttcaatattt gatgtcattc tatttcattt ttatcacatt cttatttaag ttatgtattg   1380
ctattagttt tagataagaa cttttgcatt atatgcgtat tggcagctat aggtccttgt   1440
caaaattttg ccatagacaa gatatatgac ataaattctt tccctttagg cacaaaatat   1500
atttcctgta gaaaatagtt aagattcacc tcaatcggat acaacctctc tctaccttca   1560
agatggggtt aaggtcttgt acatactacc ctctccagac cgcacttgtg agattacatg   1620
ggatttgttg ttgttgttat tcaccttgat tgaatcatcg ctcaccctga tttttgtcgt   1680
tttaatctgg ctgggtttcc tttcttttttt tcttcatccc tgtagggcaa aaaataggaa   1740
ctctgctttt caattgggga gttttgggga tggagtagac cacaaaccat acttattgaa   1800
gctaatttag agctaaagat gctaaagtac cttttttgatt agtcataaat cataatgtga   1860
atgtactagc tttggttatt tgaccgcaca aatcaaacta ggacttagtt tcgacgtggt   1920
ataagtgttc ctatttttact tatataggaa ctcttctcct tttgtttact ttgtaaaggg   1980
tgtaagatga ttaatatatt gtctactctt ggggggtctct gggtatgcta aatgagctaa   2040
gaggtgatta gaactctagc aaggattgta atgacgtatt aaggacatga tcaggaaccc   2100
atgtgcagtg tttgcgcagg attatgcacc aactaatggt caatgagcac gtctaatcta   2160
gtttaatgtt tgagttgtta tttgattgac ttttcaatat caataaacca tcggtcaaat   2220
ttcatgatat tttactgagc catctgtaat atgatgtcca accatgccta ttcaacaaaa   2280
tgaaaattta aaaacttgca gaattagttg agcgccacca gatacttaaa gctatgccaa   2340
ctgcgtctaa ccgaagttga aagacaaagt tgagtaagag cacagttttt gatgtgtgga   2400
ttaggtgcat gtcacaagtt cgaaccctgt agcagacagt cctggtattt aagtggaaaa   2460
gggtagaggg ctgggcatat tatccatcga gtttcgaacc gtgcgtcact agcccttagg   2520
gatttcagtt atcataaact taaaaaaaag ttgaaataca aagttaattt tttaccacaa   2580
aatctttgaa ttttattgta gttgagtttt tagcatcagt taaaaaattt gcttagcata   2640
```

```
tagacagaga tatttaaagc tatgccagtt gccttgatag agtctaaaat taccttgatt    2700
agttggttag tgctcttcgt tatattgagt cacaagatta atttatgaag acaaagttct    2760
taaggaccat tgcgtggttg agttttattt gcataagctt gctaacctat ttttttttctg   2820 ctcacatacc agaagqqgat atgatgttgt aatgacaaca agcctctctt cagatgttcc    2880
tgttggatac ttctcttggg ctgagtatga tatcatggct ccagtagaac ctaaaacaga    2940
gaatgccttg gcagcggctt tcatttctaa ttgtggtgct cgcaacttcc gtttgcaagc    3000
tttagaagcc cttgaaaggg caaatatcag aattgactct tatggaagtt gtcatcataa    3060
cagggatgga agaggttagt atatttcaaa tatccaaact tactgaagaa ttagaggata    3120
gaatatggat ggtgcatctt ctaagtagcg ccactaggga gctaattcta gtccatagag    3180
tagtattatg ttttttgattg actcttgggt gtcacaccctt cctccaggag ataggatttc    3240
actaccagtg caaaccttat gttttttctc ctggctaatg tgagcatgca tgtcgtggtt    3300
tttttagtga ttcgaattta tgctagtctt gcttctcgat ggattatttt gctctttttc    3360
ttgtttaaaa attgagttac aattttgcca cctgataaga ataaatttgg aatacaacgt    3420
ttaaatagtt caaattcatt ctgaggaagt tagactgtga tttgttgatg aagagagaag    3480
tatagccaga aaaggtgtgg tggacaaatc atctttctga atgcagtgta ttttacacat    3540
gcatttggtg taggtttagg ctaatatcca attgaatcac gttacttgtc aataaaaagt    3600
atccaattaa atctaacttc tggtttctgt tctcaatttg atggcagttg acaaagtggc    3660
agcactgaag cgttaccagt ttagcttggc ttttgagaat tctaatgagg aggactatgt    3720
aactgaaaaa ttcttttcagt ctctggtagc tggtaatcac atttgttttt tcttattggg    3780
tttatagact tggatttttca gaattgagag catctattat agctcaatcc atcccttaac    3840
atgatagata catttgttcc tagttgtatt tgatgtggtt ttgggaagat cttctgggtt    3900
tactagcaga ccttggaatt gtagtatcta aagcgtacaa ttatttatag aagttgcagg    3960
aaggacaaac ttctgaattc tgataaaattc ttgacacatc caacaatggt ttgaatctag    4020
acttgcattt ctgtagaatg cacaatgtgc tctacagtct acactgagat gactcaaata    4080
tttttggaat ttgttgaaat gattttgggg gtatcatctt tgttgagcat ttctttatg    4140 ctctaagaat aaattctctt ttttcgaggt ttatcccatg tttaagattt tgataatttt    4200
attagttcta gattgagatt taaggtttca gcttgctgat aaaagtaagt ctataaaact    4260
tgtagggtca atccctgtgg tggttggtgc tccaaacatc caagactttg cgccttctcc    4320
taattcagtt ttacacatta aagagataaa agatgctgaa tcaattgcca ataccatgaa    4380
gtaccttgct caaaacccta ttgcatataa tgagtcatta aggtatgtat caataaaaat    4440
tgttgttatc gtcgtttttt gttttgtttt tttcaggtta ctccagttgt ttacttgata    4500
atgggatggt actcttctta attgttcgat atcctgtcgt tgcaattata cactgtccaa    4560
atctctcttt tttaagtcat ctggtacctt ttgagcatag aattacgaag aaaatggtac    4620
agacccattt cactaaaatg ttttcacaac tgtatttcca gttttgacc aatttatata    4680 tcgatattgc cttttgatgt taggtggata actgaattga acgaaaacac aatggatctc    4740
tctctgtttt tctgtagtta caagacattt cttccctgtc aagatttact taatgttttc    4800
ttgaatttac tggacgtgta acaaatgatt tgctttatt gttcaggtgg aagtttgagg    4860
gcccatctga tgccttcaaa gcccttgttg atatggcagc agttcattca tcttgtcgtt    4920
tgtgcatctt cttggcaagt aggatccggg aaagagaaga gcagagtcca aaatttatga    4980
agcgtccctg caaatgtacc agagggactg aaactgtata tcatgtatat gtaggtgaaa    5040
```

-continued

```
gaggcaggtt tgagatggat tccatttttct taaggtattt ttaatctcca gttactgaat    5100
tctgaccatg aatgtctaag aaaatttcct ctgacctgtt aaaaagaata tcaaagtata    5160
ctttctgaat acgttcgagg cagatatgca tctactttt cctatagttc aactgctttt    5220
gtattattat tgttattgtt attgttatct tcttttgctg ttgttttgca ctcaatcact    5280
cagtggatga caattttga gatatgttct ccagaactct accagacaaa gaataatatt    5340
ttagattttt taatgaggaa atagtatttt agatgtctag atcgtgaaat cttctatgct    5400 ttttcttaa ttcatttgaa gatggggtag actctctctc tgtccacatg tccgctgtct    5460
tcttgtccaa gacacttgaa aaagctatcg tctacttata cctttatatg ttccctctta    5520
ccaagctgcg tattatttc atgttgaaga gctaaaagtg gaacccgaga gttagcagct    5580
tctgctgggc cttccagtag cctccatctg tacaactgtg tgatcaaata aatcttcctt    5640
tttctcctag agattccggc aagtaaagct gaaagcggag ctcttactta caatgaatac    5700
atgtgaaata ctcatgata tcttggccta gagtcgatag tctaagggggt tgaaaagtgt    5760 ttgaacatga aaagaggaaa agagatttgt ggttggataa caccatagag acactatcaa    5820
tgtgtgtata atcatttctg attgattcat aggctgaagc aggacgatcc tgaaagttgt    5880
tgtagtgggt agtttcttcc aatttcttcc attatgtgga cttcctgcac ccccattata    5940 tctttttgaat tctgtcctgg aattctcctc ctgttaaatt gcgaagcatc cccccccccc    6000
ccttttttaa tgttttctcg tcagagctttt ccttatttct ccgatataaa ctttgaatca    6060
ccctaatttc tatatctgtg caggtcgagt gatttgtctt tgaaggcgtt tgaatctgct    6120
atcctctcga ggttcaagtc tgttaaacat gttcctgttt ggaaggagga aagacctcaa    6180
gtactacgag gtggtgatga actcaaactt tacaaagtat atcctgttgg cttgacacag    6240
agacaagcat tgttttcctt cagattcaac ggggatactg agtttaacaa ttacattcaa    6300
agccacccat gtgcaaaatt tgaagccatc ttcgtatag                            6339
```

```
<210> SEQ ID NO 2
<211> LENGTH: 1503
<212> TYPE: DNA
<213> ORGANISM: Nicotiana benthamiana
<220> FEATURE:
<221> NAME/KEY: CDS
<222> LOCATION: (1)..(1503)

<400> SEQUENCE: 2
```

| | | | | | | | | | | | | | | | | |
|---|---|---|---|---|---|---|---|---|---|---|---|---|---|---|---|---|
| atg | aga | tcg | gcg | tca | aat | tca | aac | gca | ccc | aat | aag | caa | tgg | cgc | aat | 48 |
| Met | Arg | Ser | Ala | Ser | Asn | Ser | Asn | Ala | Pro | Asn | Lys | Gln | Trp | Arg | Asn | |
| 1 | | | | 5 | | | | | 10 | | | | | 15 | | |
| tgg | ttg | cct | ctg | ttc | gtt | gcc | cta | gtg | att | ata | gct | gag | ttt | tct | ttt | 96 |
| Trp | Leu | Pro | Leu | Phe | Val | Ala | Leu | Val | Ile | Ile | Ala | Glu | Phe | Ser | Phe | |
| | | 20 | | | | | 25 | | | | | 30 | | | | |
| ctg | gtt | cga | ctc | gac | gta | gct | gaa | aaa | gcc | aac | tct | tgg | gcc | gaa | tcg | 144 |
| Leu | Val | Arg | Leu | Asp | Val | Ala | Glu | Lys | Ala | Asn | Ser | Trp | Ala | Glu | Ser | |
| | | | 35 | | | | | 40 | | | | | 45 | | | |
| ttt | tat | cag | ttc | acc | acg | gcc | tct | tgg | tcc | acc | tct | aaa | ctg | gct | gtt | 192 |
| Phe | Tyr | Gln | Phe | Thr | Thr | Ala | Ser | Trp | Ser | Thr | Ser | Lys | Leu | Ala | Val | |
| | 50 | | | | | 55 | | | | | 60 | | | | | |
| gac | cac | ggc | gac | gtt | gag | gag | gtc | cag | ttg | ggt | gtt | ttg | agt | ggt | gag | 240 |
| Asp | His | Gly | Asp | Val | Glu | Glu | Val | Gln | Leu | Gly | Val | Leu | Ser | Gly | Glu | |
| 65 | | | | | 70 | | | | | 75 | | | | | 80 | |
| ttc | gat | cat | ggc | ttc | gta | cct | ggg | agt | tgc | gag | gag | tgg | ttg | gaa | agg | 288 |
| Phe | Asp | His | Gly | Phe | Val | Pro | Gly | Ser | Cys | Glu | Glu | Trp | Leu | Glu | Arg | |
| | | | | 85 | | | | | 90 | | | | | 95 | | |

-continued

```
gaa gat tct gtg gct tat tcg agg gat ttt gat aat gaa cca att ttt       336
Glu Asp Ser Val Ala Tyr Ser Arg Asp Phe Asp Asn Glu Pro Ile Phe
        100                 105                 110 gtt cat ggg cct gga cag gaa ttg aaa tct tgt tcc ata gga tgt aag       384
Val His Gly Pro Gly Gln Glu Leu Lys Ser Cys Ser Ile Gly Cys Lys
    115                 120                 125 ttt gga aca gat tcc aat aag aag cct gat gca gca ttt cgg cta cca       432
Phe Gly Thr Asp Ser Asn Lys Lys Pro Asp Ala Ala Phe Arg Leu Pro
130                 135                 140 caa caa gct ggc aca gct agt gtg cta cgg tcg atg gag tca gct caa       480
Gln Gln Ala Gly Thr Ala Ser Val Leu Arg Ser Met Glu Ser Ala Gln
145                 150                 155                 160 tac tat gca gag aac aac att act ttg gca cga cga agg gga tat gat       528
Tyr Tyr Ala Glu Asn Asn Ile Thr Leu Ala Arg Arg Arg Gly Tyr Asp
                165                 170                 175 gtt gta atg aca aca agc ctc tct tca gat gtt cct gtt gga tac ttc       576
Val Val Met Thr Thr Ser Leu Ser Ser Asp Val Pro Val Gly Tyr Phe
            180                 185                 190 tct tgg gct gag tat gat atc atg gct cca gta gaa cct aaa aca gag       624
Ser Trp Ala Glu Tyr Asp Ile Met Ala Pro Val Glu Pro Lys Thr Glu
        195                 200                 205 aat gcc ttg gca gcg gct ttc att tct aat tgt ggt gct cgc aac ttc       672
Asn Ala Leu Ala Ala Ala Phe Ile Ser Asn Cys Gly Ala Arg Asn Phe
    210                 215                 220 cgt ttg caa gct tta gaa gcc ctt gaa agg gca aat atc aga att gac       720
Arg Leu Gln Ala Leu Glu Ala Leu Glu Arg Ala Asn Ile Arg Ile Asp
225                 230                 235                 240 tct tat gga agt tgt cat cat aac agg gat gga aga gtt gac aaa gtg       768
Ser Tyr Gly Ser Cys His His Asn Arg Asp Gly Arg Val Asp Lys Val
                245                 250                 255 gca gca ctg aag cgt tac cag ttt agc ttg gct ttt gag aat tct aat       816
Ala Ala Leu Lys Arg Tyr Gln Phe Ser Leu Ala Phe Glu Asn Ser Asn
            260                 265                 270 gag gag gac tat gta act gaa aaa ttc ttt cag tct ctg gta gct ggg       864
Glu Glu Asp Tyr Val Thr Glu Lys Phe Phe Gln Ser Leu Val Ala Gly
        275                 280                 285 tca atc cct gtg gtg gtt ggt gct cca aac atc caa gac ttt gcg cct       912
Ser Ile Pro Val Val Val Gly Ala Pro Asn Ile Gln Asp Phe Ala Pro
    290                 295                 300 tct cct aat tca gtt tta cac att aaa gag ata aaa gat gct gaa tca       960
Ser Pro Asn Ser Val Leu His Ile Lys Glu Ile Lys Asp Ala Glu Ser
305                 310                 315                 320 att gcc aat acc atg aag tac ctt gct caa aac cct att gca tat aat      1008
Ile Ala Asn Thr Met Lys Tyr Leu Ala Gln Asn Pro Ile Ala Tyr Asn
                325                 330                 335 gag tca tta agg tgg aag ttt gag ggc cca tct gat gcc ttc aaa gcc      1056
Glu Ser Leu Arg Trp Lys Phe Glu Gly Pro Ser Asp Ala Phe Lys Ala
            340                 345                 350 ctt gtt gat atg gca gca gtt cat tca tct tgt cgt ttg tgc atc ttc      1104
Leu Val Asp Met Ala Ala Val His Ser Ser Cys Arg Leu Cys Ile Phe
        355                 360                 365 ttg gca agt agg atc cgg gaa aga gaa gag cag agt cca aaa ttt atg      1152
Leu Ala Ser Arg Ile Arg Glu Arg Glu Glu Gln Ser Pro Lys Phe Met
    370                 375                 380 aag cgt ccc tgc aaa tgt acc aga ggg act gaa act gta tat cat gta      1200
Lys Arg Pro Cys Lys Cys Thr Arg Gly Thr Glu Thr Val Tyr His Val
385                 390                 395                 400 tat gta ggt gaa aga ggc agg ttt gag atg gat tcc att ttc tta agg      1248
Tyr Val Gly Glu Arg Gly Arg Phe Glu Met Asp Ser Ile Phe Leu Arg
```

```
                            405                      410                      415
tcg agt gat ttg tct ttg aag gcg ttt gaa tct gct atc ctc tcg agg         1296
Ser Ser Asp Leu Ser Leu Lys Ala Phe Glu Ser Ala Ile Leu Ser Arg
            420                      425                      430 ttc aag tct gtt aaa cat gtt cct gtt tgg aag gag gaa aga cct caa         1344
Phe Lys Ser Val Lys His Val Pro Val Trp Lys Glu Glu Arg Pro Gln
            435                      440                      445 gta cta cga ggt ggt gat gaa ctc aaa ctt tac aaa gta tat cct gtt         1392
Val Leu Arg Gly Gly Asp Glu Leu Lys Leu Tyr Lys Val Tyr Pro Val
450                      455                      460 ggc ttg aca cag aga caa gca ttg ttt tcc ttc aga ttc aac ggg gat         1440
Gly Leu Thr Gln Arg Gln Ala Leu Phe Ser Phe Arg Phe Asn Gly Asp
465                      470                      475                  480 act gag ttt aac aat tac att caa agc cac cca tgt gca aaa ttt gaa         1488
Thr Glu Phe Asn Asn Tyr Ile Gln Ser His Pro Cys Ala Lys Phe Glu
                485                      490                      495 gcc atc ttc gta tag                                                     1503
Ala Ile Phe Val
            500

<210> SEQ ID NO 3
<211> LENGTH: 500
<212> TYPE: PRT
<213> ORGANISM: Nicotiana benthamiana

<400> SEQUENCE: 3

Met Arg Ser Ala Ser Asn Ser Asn Ala Pro Asn Lys Gln Trp Arg Asn
1               5                   10                  15

Trp Leu Pro Leu Phe Val Ala Leu Val Ile Ile Ala Glu Phe Ser Phe
                20                  25                  30

Leu Val Arg Leu Asp Val Ala Glu Lys Ala Asn Ser Trp Ala Glu Ser
            35                  40                  45

Phe Tyr Gln Phe Thr Thr Ala Ser Trp Ser Thr Ser Lys Leu Ala Val
        50                  55                  60

Asp His Gly Asp Val Glu Glu Val Gln Leu Gly Val Leu Ser Gly Glu
65                  70                  75                  80

Phe Asp His Gly Phe Val Pro Gly Ser Cys Glu Glu Trp Leu Glu Arg
                85                  90                  95

Glu Asp Ser Val Ala Tyr Ser Arg Asp Phe Asp Asn Glu Pro Ile Phe
            100                 105                 110

Val His Gly Pro Gly Gln Glu Leu Lys Ser Cys Ser Ile Gly Cys Lys
        115                 120                 125

Phe Gly Thr Asp Ser Asn Lys Lys Pro Asp Ala Ala Phe Arg Leu Pro
130                 135                 140

Gln Gln Ala Gly Thr Ala Ser Val Leu Arg Ser Met Glu Ser Ala Gln
145                 150                 155                 160

Tyr Tyr Ala Glu Asn Asn Ile Thr Leu Ala Arg Arg Arg Gly Tyr Asp
                165                 170                 175

Val Val Met Thr Thr Ser Leu Ser Ser Asp Val Pro Val Gly Tyr Phe
            180                 185                 190

Ser Trp Ala Glu Tyr Asp Ile Met Ala Pro Val Glu Pro Lys Thr Glu
        195                 200                 205

Asn Ala Leu Ala Ala Ala Phe Ile Ser Asn Cys Gly Ala Arg Asn Phe
210                 215                 220

Arg Leu Gln Ala Leu Glu Ala Leu Glu Arg Ala Asn Ile Arg Ile Asp
225                 230                 235                 240
```

```
Ser Tyr Gly Ser Cys His His Asn Arg Asp Gly Arg Val Asp Lys Val
                245                 250                 255

Ala Ala Leu Lys Arg Tyr Gln Phe Ser Leu Ala Phe Glu Asn Ser Asn
            260                 265                 270

Glu Glu Asp Tyr Val Thr Glu Lys Phe Phe Gln Ser Leu Val Ala Gly
        275                 280                 285

Ser Ile Pro Val Val Val Gly Ala Pro Asn Ile Gln Asp Phe Ala Pro
    290                 295                 300

Ser Pro Asn Ser Val Leu His Ile Lys Glu Ile Lys Asp Ala Glu Ser
305                 310                 315                 320

Ile Ala Asn Thr Met Lys Tyr Leu Ala Gln Asn Pro Ile Ala Tyr Asn
                325                 330                 335

Glu Ser Leu Arg Trp Lys Phe Glu Gly Pro Ser Asp Ala Phe Lys Ala
            340                 345                 350

Leu Val Asp Met Ala Ala Val His Ser Ser Cys Arg Leu Cys Ile Phe
        355                 360                 365

Leu Ala Ser Arg Ile Arg Glu Arg Glu Gln Ser Pro Lys Phe Met
    370                 375                 380

Lys Arg Pro Cys Lys Cys Thr Arg Gly Thr Glu Thr Val Tyr His Val
385                 390                 395                 400

Tyr Val Gly Glu Arg Gly Arg Phe Glu Met Asp Ser Ile Phe Leu Arg
                405                 410                 415

Ser Ser Asp Leu Ser Leu Lys Ala Phe Glu Ser Ala Ile Leu Ser Arg
            420                 425                 430

Phe Lys Ser Val Lys His Val Pro Val Trp Lys Glu Glu Arg Pro Gln
        435                 440                 445

Val Leu Arg Gly Gly Asp Glu Leu Lys Leu Tyr Lys Val Tyr Pro Val
    450                 455                 460

Gly Leu Thr Gln Arg Gln Ala Leu Phe Ser Phe Arg Phe Asn Gly Asp
465                 470                 475                 480

Thr Glu Phe Asn Asn Tyr Ile Gln Ser His Pro Cys Ala Lys Phe Glu
                485                 490                 495

Ala Ile Phe Val
        500

<210> SEQ ID NO 4
<211> LENGTH: 6367
<212> TYPE: DNA
<213> ORGANISM: Nicotiana benthamiana
<220> FEATURE:
<221> NAME/KEY: Exon1
<222> LOCATION: (1)..(354)
<220> FEATURE:
<221> NAME/KEY: Intron1
<222> LOCATION: (355)..(1047)
<220> FEATURE:
<221> NAME/KEY: Exon2
<222> LOCATION: (1048)..(1208)
<220> FEATURE:
<221> NAME/KEY: Intron2
<222> LOCATION: (1209)..(2812)
<220> FEATURE:
<221> NAME/KEY: Exon3
<222> LOCATION: (2813)..(3054)
<220> FEATURE:
<221> NAME/KEY: Variation
<222> LOCATION: (3054)..(3054)
<223> OTHER INFORMATION: G to A substitution in FucT006
<220> FEATURE:
<221> NAME/KEY: Intron3
<222> LOCATION: (3055)..(3632)
<220> FEATURE:
```

```
<221> NAME/KEY: Exon4
<222> LOCATION: (3633)..(3737)
<220> FEATURE:
<221> NAME/KEY: Intron4
<222> LOCATION: (3738)..(4250)
<220> FEATURE:
<221> NAME/KEY: Exon5
<222> LOCATION: (4251)..(4407)
<220> FEATURE:
<221> NAME/KEY: Intron5
<222> LOCATION: (4408)..(4827)
<220> FEATURE:
<221> NAME/KEY: Exon6
<222> LOCATION: (4828)..(5055)
<220> FEATURE:
<221> NAME/KEY: Intron6
<222> LOCATION: (5056)..(6111)
<220> FEATURE:
<221> NAME/KEY: Exon7
<222> LOCATION: (6112)..(6367)

<400> SEQUENCE: 4
```

| | | | | | |
|---|---|---|---|---|---|
| atgagatcgt | cgtcaaattc | aaacgcaccc | gataaacaat | ggcgcaattg | gttgcctctg | 60 |
| ttcgttgccc | tagttgttat | agcagaaatt | tcttttctgg | ttcgactcga | cgtggctgaa | 120 |
| aaagccaact | cttgggctga | gtcgttttat | cagttcacca | cggcgtcttg | gtcaacctcc | 180 |
| aaactggctg | ttgacggcgg | cgatgttgat | gaggtcctgt | tgggtgtttt | gagtggtgag | 240 |
| tttgatcagg | gcttcctacc | ttggagttgc | gaggagtggt | tggaaaggga | agattatgtg | 300 |
| gcttatgcga | gggattttga | taatgaacca | attttgttc  | atgggcctgg | acaggttata | 360 |
| tccacttcta | tttattagtg | tgctatttct | ttttggatc  | gttgttagtg | atatgcctaa | 420 |
| atttctttag | ataatgtatt | tgtttatttt | tgtggatttt | atcgcaatcc | tagtgttaga | 480 |
| taatccttaa | atacggggta | ttgaattatt | atggactcaa | acagagcatt | tatgatattg | 540 |
| aggattcata | cagcctactc | caactagttt | gggatagagg | attagtagta | gtagttgttg | 600 |
| ttgtctcaaa | aaatgtattg | gcatctcagt | acactttagg | tgcatgattg | atttcagtct | 660 |
| tttggctatt | attgtagctg | gctcatagca | agagaggttt | gcttagttga | tagattttag | 720 |
| tttttcagct | tcatttgctg | tgagatttta | taaggattc  | taatccttt  | atttaaaagt | 780 |
| ggggaaatag | cagagaagct | ttggtgaatt | ttcatattga | tttgcctttt | gaagcatata | 840 |
| tcattcagc  | attcctttat | ttatttcatc | acaaaaaata | aaactctaat | ggaataatca | 900 |
| gaaatcaatt | tatcataacg | caaataccac | ttcttattgt | tggtggtctc | ccatgctatg | 960 |
| cgcttgttac | atattcccta | ctcacctctg | actttatgaa | tgtcccatcc | tgtacggaat | 1020 |
| tctgatgtct | attcaatcac | tatacaggaa | ttgaaatctt | gttccatagg | atgtaagttt | 1080 |
| ggaacagatt | ccaataagaa | gcctgatgca | gcatttcggc | taccacaaca | agctggcaca | 1140 |
| gctagtgtgc | tacggtccat | ggagtcagct | caatactatg | cagagaacaa | cattactttg | 1200 |
| gcacgacggt | gggtaagcac | tctatgaaag | aagtcttatt | tcattccctg | cctttattgg | 1260 |
| caaatttctt | ttcaatattt | gatgtcattc | tctttcattt | ttatcacatt | cttatttaag | 1320 |
| ttatgtattg | ctcttagttt | tagataagaa | cttttgcatt | ataagcgtat | tggaagctat | 1380 |
| aggtccttgt | caaattttg  | tcatagacaa | gatattttaa | aactgatgac | atgaattctt | 1440 |
| tcccttagt  | cacaaaatat | atttcctgta | gaaaatagtt | aagattcact | tctatcggaa | 1500 |
| ataacctctc | taccttcaag | atgggggcaa | ggtctgcgta | catactaccc | tctctaaacc | 1560 |
| ccacttgtgg | gattacattg | ggttttgat  | gttgttttg  | ttgttattca | ccttgactga | 1620 |
| atcatccctg | accctgcttt | ttgtcgttt  | aatcttgttg | ggtttccttt | ctcttttct  | 1680 |

```
tcattcctgt aggacacaaa atgggaaatc tgcttttcaa ttgggagttt gggtatggag    1740
tggaccacga accatactta ttgaagctaa tttagagata aagatgctaa agtaccttt    1800
tgattagtca taaatcatat tgtgaattac tagctttggt tatttgaccg aagaaatcaa    1860
actggactta gtttcgacgt ggtataagtc tcttcctatt ttacttatat agaagctctt    1920
ctccttttgt ttactttgta aagggtataa gatgattaat atattgtcta ctcttggggg    1980
tctctgggta tgctatatga gctaagaggt gattagaact ccagcaagga ttgtaatgac    2040
atattaagga catgatcaga acccatgttc agtgtttgca caggattatg caccaactaa    2100
tggtcaatga gcacatctaa tctagtttaa tgtttgagtt gttattggat tgacttttca    2160
ttatcaataa accatcggtc aaatttcatg atattttacg gagccatctg taatatgatg    2220
tccaaccatg cctattcaac aaaatgaaaa ttgaaaactt gcagaattag ttgagcgcca    2280
cgccgccacc agatacttaa agctatgcca actgcgtcta acagaagttg aaagacaaag    2340
ttgagtaaga gcacaatttt tgatgtgtgg attaggtgca tgtcacaagt tcgaaccta    2400
tcgcagacaa agtcctagta tttaagtgga aagggtaga gggctgggcg tattaccgat    2460
cgaatttcga accgtgcgtc actagtcctt agggatttca gttatcataa acttaaaaaa    2520
gttgaaatac aaagttaatt ttttaccac aaaatctttg aattttattg tagttgagat    2580
tttagcatca tcttgcttac aaaatttgct tagcatatag acagagatat ttaaagctat    2640
gccagttgcc ttgatggagt ctacaattac cttggttagt tggttagtgc tcttcgtgag    2700
attgagtcac aagattaatt tatgaagcca agttcttaa ggaccattgc gtggttgagt    2760
tttatttgca taagcttgct aacctatttt ctttttccg ctcacatacc agaaggggat    2820
atgatgttgt aatgacaaca agcctctctt cagatgttcc tgttggatac ttctcttggg    2880
ctgagtatga tatcatggct ccagtagaac ctaaaacaga gaatgccttg gcagccgctt    2940
tcatttctaa ttgcggtgct cgcaacttcc gtttgcaagc tttagaagcc cttgaaaggg    3000
caaatatcag aattgactct tatggcagtt gtcatcataa cagggatgga agaggttagt    3060
atatttcaaa tatccaaact tactgaagaa ttagaggata gaatatggat ggtgcatctt    3120
ctaagaagcg ccactaggga gctaattctt gtccatagag tagtattatg ttttgatg    3180
actcttcctt gggtatcaca ccttcctcca ggagacagga tttcactacc agtgcaaacc    3240
ttatgttttt ctcctggcta atgtgagcat gcatttcgtg gttttatag tgattcgaat    3300
ttatgctagt ccaatgattg cttctcaatg gattattttg ctctttttat tgtttaaaaa    3360
ttgagttaca attttccacc tgataagaat aaatttggaa tacaacattt aaatagttca    3420
aattcattat gaggaagtta gactgtgatt tgttgaagag agaagtatag ccagaaaagg    3480
tgtggtggac aaatcatctt tctgaatgcg gtgtatttta tacatgcatt tggtgtaggt    3540
ttaggctaat atctaattga atcacgttac ttgtcaacaa aaagtatcca attaaatcta    3600
acttctggtt tctgttctca atttgatggc agtagacaaa gtggcagcac tgaagcgtta    3660
caagtttagc ttggcttttg agaattctaa tgaggaggac tatgtaaccg aaaaattctt    3720
tcagtctctg gtagctggta atcacatttg ttttttctta ttggatttat agacttggat    3780
tttcagaatt gagagcatct attatagctc agtcgatccc tcaacatgat agatacattt    3840
gttcctagtt gtatttgatg tggttttggg aagattttct gggtttacta gcagaccttg    3900
gaattgtagt atctaaagcg tacaattatt tatagaagtt gcaggaagga caaacttctg    3960
aattctgata aactcttgac acattctacg atggtttgga tctagacttg catttctgta    4020
gaatgcacaa tgtgctctat agtctacact gagatggctc aaatatttt ggaattttgt    4080
```

```
tgaaatgatt tgggggtat catttagtt gagcatttc tttatgctct aagactaaat    4140
tctctttttt cgaggtttat cctatgttta agattttgat aattttatag ttctggattg    4200
agatttaagg tttcaacttg ctgataaaag taagtctata aaacttgtag ggtcaatccc    4260
tgtggtggtt ggtgctccaa acatccaaga ctttgcgcct tctcctaatt cagttttaca    4320
cattaaagag ataaaagatg ctgaattaat tgccaatacc atgacgtacc ttgctcaaaa    4380
ccctattgca tctaatgagt cattaaggta tgtatcaata aaaattgttg ttatcgtcat    4440
tttttgttct gttttttctg ttactccag ttgtttttga taatgggatg gtactcttct    4500
taattgttcg aattcctgtc gttgcaatta tacactgtcc acatctctct tttttaagtc    4560
atccggttcc ttttgatcat agaattacga agaaaaatag tacagaccca tttcactaaa    4620
atgttttcac tactgtattt ccagtttttg accaatttgt atatggatat tgccttttga    4680
tgttaggtgg ataactgaat tgaactaaaa cacaatggat ctctttctgt ttttctgtag    4740
ttacaagaca ttttttccctt tcaagattta cttaatgttt cttaaattta ctggacatct    4800
aacaaatgat ttgctttcat tgttcaggtg aagtttgag ggcccatttg atgccttcaa    4860
agccctggtt gatatggcag cagttcattc atcttgccgt ttgtgcatct tcttggcaag    4920
taggatccag gaaagagaag agcatagtcc aaaatttacg aagcgcccct gcaaatgtac    4980
cagagagact gaaactgtct atcatgtata tgtacgtgaa agagggaggt ttgagatgga    5040
ttccattttc ttaaggtatt tttaatctcc agttactgag ttctgaccgt gaatgtctaa    5100
gcaaatttt cctgacttgt taaagaata tcaaagtata ttttctgaat ctgttcgagg    5160
cagatatgca tctactttt cccatcagtt caactgcttt atactattat ttgttttagc    5220
ttcttttgct gttgttttgc actcaatcac tcagtggatg acaatttttg agatatgttc    5280
tcctgaattc tacctgacaa agaacaatgt tctagatttt ttaatgagga aataacattt    5340
gagatgtcta atcggaaaa tttctgtgc ttttccttca attcatttgg gatggggtag    5400
actatttctc tgtccatata tccgttgtct tcttgtccaa gaaacttgaa aagctatcat    5460
ctacatttac ctttgtctgt tccctcttac caagctgcgt gattattttc atgttcaaga    5520
ggtaaaagta gaacccgat agtttgcagc ttctgctggg ccttccagtc tcctccatct    5580
gtacaactgt gtgatcaaat aattcctctt tttctcttag agattccgac aagtaagctg    5640
aaagcggagc tcttatttac gatgaatgca tgtgaaatac tacatgatat cttggccaag    5700
agtcgatagt ctaaggggtt gaaaagtgtt tgaacatgaa agaggaaaag agtattgtgg    5760
ttggataaca ccatagagac ctctcaatct gtgtataatc atttctgatt gattcataga    5820
ctgaagcagg acaatcttga aagttgttgt agtgggtagt tgcttctgta tttatcggag    5880
taacgaaact aaaggaaaag gacattgaac ccttttcatt tttcgaaaat tcttcaaatt    5940
ttcttcatta tgtggacttc ctgcacccc attatatctt tgaattctg tcctagaatt    6000
ctctcctgct aaattgcaaa gcatccttcc tttttaatg ttttctcgtc agagctttcc    6060
ttgtctctct gatataaact tgaatcacc ctaatttctg tatctgtgca ggtcgagtga    6120
tttgtcttta aaggcgtttg aatctgctat tctctcgagg ttcaagtctg ttaaacatgt    6180
tcctgtttgg agggaggaaa gacctcaagt actacgaggt ggtgatgaac tcaaacttta    6240
ctaagtatat cctgttggct tgacacagag acaagcattg ttttccttca gattcaacgg    6300
ggatactgag tttaagaatt acattcaaag ccacccatgt gcaaaatttg aagccatctt    6360
cgtatag                                                              6367
```

<210> SEQ ID NO 5
<211> LENGTH: 1503
<212> TYPE: DNA
<213> ORGANISM: Nicotiana benthamiana
<220> FEATURE:
<221> NAME/KEY: CDS
<222> LOCATION: (1)..(1380)

<400> SEQUENCE: 5

| | | | | | | | | | | | | | | | | |
|---|---|---|---|---|---|---|---|---|---|---|---|---|---|---|---|---|
| atg | aga | tcg | tcg | tca | aat | tca | aac | gca | ccc | gat | aaa | caa | tgg | cgc | aat | 48 |
| Met | Arg | Ser | Ser | Ser | Asn | Ser | Asn | Ala | Pro | Asp | Lys | Gln | Trp | Arg | Asn | |
| 1 | | | | 5 | | | | | 10 | | | | | 15 | | |
| tgg | ttg | cct | ctg | ttc | gtt | gcc | cta | gtt | gtt | ata | gca | gaa | att | tct | ttt | 96 |
| Trp | Leu | Pro | Leu | Phe | Val | Ala | Leu | Val | Val | Ile | Ala | Glu | Ile | Ser | Phe | |
| | | | 20 | | | | | 25 | | | | | 30 | | | |
| ctg | gtt | cga | ctc | gac | gtg | gct | gaa | aaa | gcc | aac | tct | tgg | gct | gag | tcg | 144 |
| Leu | Val | Arg | Leu | Asp | Val | Ala | Glu | Lys | Ala | Asn | Ser | Trp | Ala | Glu | Ser | |
| | | 35 | | | | | 40 | | | | | 45 | | | | |
| ttt | tat | cag | ttc | acc | acg | gcg | tct | tgg | tca | acc | tcc | aaa | ctg | gct | gtt | 192 |
| Phe | Tyr | Gln | Phe | Thr | Thr | Ala | Ser | Trp | Ser | Thr | Ser | Lys | Leu | Ala | Val | |
| | 50 | | | | | 55 | | | | | 60 | | | | | |
| gac | ggc | ggc | gat | gtt | gat | gag | gtc | ctg | ttg | ggt | gtt | ttg | agt | ggt | gag | 240 |
| Asp | Gly | Gly | Asp | Val | Asp | Glu | Val | Leu | Leu | Gly | Val | Leu | Ser | Gly | Glu | |
| 65 | | | | 70 | | | | | 75 | | | | | 80 | | |
| ttt | gat | cag | ggc | ttc | cta | cct | tgg | agt | tgc | gag | gag | tgg | ttg | gaa | agg | 288 |
| Phe | Asp | Gln | Gly | Phe | Leu | Pro | Trp | Ser | Cys | Glu | Glu | Trp | Leu | Glu | Arg | |
| | | | 85 | | | | | 90 | | | | | 95 | | | |
| gaa | gat | tat | gtg | gct | tat | gcg | agg | gat | ttt | gat | aat | gaa | cca | att | ttt | 336 |
| Glu | Asp | Tyr | Val | Ala | Tyr | Ala | Arg | Asp | Phe | Asp | Asn | Glu | Pro | Ile | Phe | |
| | | 100 | | | | | 105 | | | | | 110 | | | | |
| gtt | cat | ggg | cct | gga | cag | gaa | ttg | aaa | tct | tgt | tcc | ata | gga | tgt | aag | 384 |
| Val | His | Gly | Pro | Gly | Gln | Glu | Leu | Lys | Ser | Cys | Ser | Ile | Gly | Cys | Lys | |
| | 115 | | | | | 120 | | | | | 125 | | | | | |
| ttt | gga | aca | gat | tcc | aat | aag | aag | cct | gat | gca | gca | ttt | cgg | cta | cca | 432 |
| Phe | Gly | Thr | Asp | Ser | Asn | Lys | Lys | Pro | Asp | Ala | Ala | Phe | Arg | Leu | Pro | |
| 130 | | | | | 135 | | | | | 140 | | | | | | |
| caa | caa | gct | ggc | aca | gct | agt | gtg | cta | cgg | tcc | atg | gag | tca | gct | caa | 480 |
| Gln | Gln | Ala | Gly | Thr | Ala | Ser | Val | Leu | Arg | Ser | Met | Glu | Ser | Ala | Gln | |
| 145 | | | | | 150 | | | | | 155 | | | | | 160 | |
| tac | tat | gca | gag | aac | aac | att | act | ttg | gca | cga | cga | agg | gga | tat | gat | 528 |
| Tyr | Tyr | Ala | Glu | Asn | Asn | Ile | Thr | Leu | Ala | Arg | Arg | Arg | Gly | Tyr | Asp | |
| | | | 165 | | | | | 170 | | | | | 175 | | | |
| gtt | gta | atg | aca | aca | agc | ctc | tct | tca | gat | gtt | cct | gtt | gga | tac | ttc | 576 |
| Val | Val | Met | Thr | Thr | Ser | Leu | Ser | Ser | Asp | Val | Pro | Val | Gly | Tyr | Phe | |
| | | | | 180 | | | | | 185 | | | | | 190 | | |
| tct | tgg | gct | gag | tat | gat | atc | atg | gct | cca | gta | gaa | cct | aaa | aca | gag | 624 |
| Ser | Trp | Ala | Glu | Tyr | Asp | Ile | Met | Ala | Pro | Val | Glu | Pro | Lys | Thr | Glu | |
| | | | 195 | | | | | 200 | | | | | 205 | | | |
| aat | gcc | ttg | gca | gcc | gct | ttc | att | tct | aat | tgc | ggt | gct | cgc | aac | ttc | 672 |
| Asn | Ala | Leu | Ala | Ala | Ala | Phe | Ile | Ser | Asn | Cys | Gly | Ala | Arg | Asn | Phe | |
| | 210 | | | | | 215 | | | | | 220 | | | | | |
| cgt | ttg | caa | gct | tta | gaa | gcc | ctt | gaa | agg | gca | aat | atc | aga | att | gac | 720 |
| Arg | Leu | Gln | Ala | Leu | Glu | Ala | Leu | Glu | Arg | Ala | Asn | Ile | Arg | Ile | Asp | |
| 225 | | | | | 230 | | | | | 235 | | | | | 240 | |
| tct | tat | ggc | agt | tgt | cat | cat | aac | agg | gat | gga | aga | gta | gac | aaa | gtg | 768 |
| Ser | Tyr | Gly | Ser | Cys | His | His | Asn | Arg | Asp | Gly | Arg | Val | Asp | Lys | Val | |
| | | | | 245 | | | | | 250 | | | | | 255 | | |
| gca | gca | ctg | aag | cgt | tac | aag | ttt | agc | ttg | gct | ttt | gag | aat | tct | aat | 816 |
| Ala | Ala | Leu | Lys | Arg | Tyr | Lys | Phe | Ser | Leu | Ala | Phe | Glu | Asn | Ser | Asn | |
| | | | 260 | | | | | 265 | | | | | 270 | | | |

| | | |
|---|---|---|
| gag gag gac tat gta acc gaa aaa ttc ttt cag tct ctg gta gct ggg<br>Glu Glu Asp Tyr Val Thr Glu Lys Phe Phe Gln Ser Leu Val Ala Gly<br>275 280 285 | | 864 |
| tca atc cct gtg gtg gtt ggt gct cca aac atc caa gac ttt gcg cct<br>Ser Ile Pro Val Val Val Gly Ala Pro Asn Ile Gln Asp Phe Ala Pro<br>290 295 300 | | 912 |
| tct cct aat tca gtt tta cac att aaa gag ata aaa gat gct gaa tta<br>Ser Pro Asn Ser Val Leu His Ile Lys Glu Ile Lys Asp Ala Glu Leu<br>305 310 315 320 | | 960 |
| att gcc aat acc atg acg tac ctt gct caa aac cct att gca tct aat<br>Ile Ala Asn Thr Met Thr Tyr Leu Ala Gln Asn Pro Ile Ala Ser Asn<br>325 330 335 | | 1008 |
| gag tca tta agg tgg aag ttt gag ggc cca ttt gat gcc ttc aaa gcc<br>Glu Ser Leu Arg Trp Lys Phe Glu Gly Pro Phe Asp Ala Phe Lys Ala<br>340 345 350 | | 1056 |
| ctg gtt gat atg gca gca gtt cat tca tct tgc cgt ttg tgc atc ttc<br>Leu Val Asp Met Ala Ala Val His Ser Ser Cys Arg Leu Cys Ile Phe<br>355 360 365 | | 1104 |
| ttg gca agt agg atc cag gaa aga gaa gag cat agt cca aaa ttt acg<br>Leu Ala Ser Arg Ile Gln Glu Arg Glu Glu His Ser Pro Lys Phe Thr<br>370 375 380 | | 1152 |
| aag cgc ccc tgc aaa tgt acc aga gag act gaa act gtc tat cat gta<br>Lys Arg Pro Cys Lys Cys Thr Arg Glu Thr Glu Thr Val Tyr His Val<br>385 390 395 400 | | 1200 |
| tat gta cgt gaa aga ggg agg ttt gag atg gat tcc att ttc tta agg<br>Tyr Val Arg Glu Arg Gly Arg Phe Glu Met Asp Ser Ile Phe Leu Arg<br>405 410 415 | | 1248 |
| tcg agt gat ttg tct tta aag gcg ttt gaa tct gct att ctc tcg agg<br>Ser Ser Asp Leu Ser Leu Lys Ala Phe Glu Ser Ala Ile Leu Ser Arg<br>420 425 430 | | 1296 |
| ttc aag tct gtt aaa cat gtt cct gtt tgg agg gag gaa aga cct caa<br>Phe Lys Ser Val Lys His Val Pro Val Trp Arg Glu Glu Arg Pro Gln<br>435 440 445 | | 1344 |
| gta cta cga ggt ggt gat gaa ctc aaa ctt tac taa gtatatcctg<br>Val Leu Arg Gly Gly Asp Glu Leu Lys Leu Tyr<br>450 455 | | 1390 |
| ttggcttgac acagagacaa gcattgtttt ccttcagatt caacggggat actgagttta | | 1450 |
| agaattacat tcaaagccac ccatgtgcaa aatttgaagc catcttcgta tag | | 1503 |

<210> SEQ ID NO 6
<211> LENGTH: 459
<212> TYPE: PRT
<213> ORGANISM: Nicotiana benthamiana

<400> SEQUENCE: 6

Met Arg Ser Ser Asn Ser Asn Ala Pro Asp Lys Gln Trp Arg Asn
1               5                   10                  15

Trp Leu Pro Leu Phe Val Ala Leu Val Val Ile Ala Glu Ile Ser Phe
            20                  25                  30

Leu Val Arg Leu Asp Val Ala Glu Lys Ala Asn Ser Trp Ala Glu Ser
        35                  40                  45

Phe Tyr Gln Phe Thr Thr Ala Ser Trp Ser Thr Ser Lys Leu Ala Val
    50                  55                  60

Asp Gly Gly Asp Val Asp Val Leu Leu Val Leu Ser Gly Glu
65                  70                  75                  80

Phe Asp Gln Gly Phe Leu Pro Trp Ser Cys Glu Glu Trp Leu Glu Arg
                85                  90                  95

Glu Asp Tyr Val Ala Tyr Ala Arg Asp Phe Asp Asn Glu Pro Ile Phe

-continued

```
                 100                 105                 110
    Val His Gly Pro Gly Gln Glu Leu Lys Ser Cys Ser Ile Gly Cys Lys
                    115                 120                 125

Phe Gly Thr Asp Ser Asn Lys Lys Pro Asp Ala Ala Phe Arg Leu Pro
            130                 135                 140

Gln Gln Ala Gly Thr Ala Ser Val Leu Arg Ser Met Glu Ser Ala Gln
    145                 150                 155                 160

Tyr Tyr Ala Glu Asn Asn Ile Thr Leu Ala Arg Arg Arg Gly Tyr Asp
                    165                 170                 175

Val Val Met Thr Thr Ser Leu Ser Ser Asp Val Pro Val Gly Tyr Phe
                180                 185                 190

Ser Trp Ala Glu Tyr Asp Ile Met Ala Pro Val Glu Pro Lys Thr Glu
                195                 200                 205

Asn Ala Leu Ala Ala Ala Phe Ile Ser Asn Cys Gly Ala Arg Asn Phe
                210                 215                 220

Arg Leu Gln Ala Leu Glu Ala Leu Glu Arg Ala Asn Ile Arg Ile Asp
    225                 230                 235                 240

Ser Tyr Gly Ser Cys His His Asn Arg Asp Gly Arg Val Asp Lys Val
                    245                 250                 255

Ala Ala Leu Lys Arg Tyr Lys Phe Ser Leu Ala Phe Glu Asn Ser Asn
                260                 265                 270

Glu Glu Asp Tyr Val Thr Glu Lys Phe Phe Gln Ser Leu Val Ala Gly
                275                 280                 285

Ser Ile Pro Val Val Val Gly Ala Pro Asn Ile Gln Asp Phe Ala Pro
                290                 295                 300

Ser Pro Asn Ser Val Leu His Ile Lys Glu Ile Lys Asp Ala Glu Leu
    305                 310                 315                 320

Ile Ala Asn Thr Met Thr Tyr Leu Ala Gln Asn Pro Ile Ala Ser Asn
                    325                 330                 335

Glu Ser Leu Arg Trp Lys Phe Glu Gly Pro Phe Asp Ala Phe Lys Ala
                340                 345                 350

Leu Val Asp Met Ala Ala Val His Ser Ser Cys Arg Leu Cys Ile Phe
                355                 360                 365

Leu Ala Ser Arg Ile Gln Glu Arg Glu His Ser Pro Lys Phe Thr
            370                 375                 380

Lys Arg Pro Cys Lys Cys Thr Arg Glu Thr Glu Thr Val Tyr His Val
    385                 390                 395                 400

Tyr Val Arg Glu Arg Gly Arg Phe Glu Met Asp Ser Ile Phe Leu Arg
                    405                 410                 415

Ser Ser Asp Leu Ser Leu Lys Ala Phe Glu Ser Ala Ile Leu Ser Arg
                420                 425                 430

Phe Lys Ser Val Lys His Val Pro Val Trp Arg Glu Glu Arg Pro Gln
                435                 440                 445

Val Leu Arg Gly Gly Asp Glu Leu Lys Leu Tyr
    450                 455
```

<210> SEQ ID NO 7
<211> LENGTH: 5937
<212> TYPE: DNA
<213> ORGANISM: Nicotiana benthamiana
<220> FEATURE:
<221> NAME/KEY: Exon1
<222> LOCATION: (1)..(396)
<220> FEATURE:
<221> NAME/KEY: Intron1
<222> LOCATION: (397)..(1400)

```
<220> FEATURE:
<221> NAME/KEY: Exon2
<222> LOCATION: (1401)..(1561)
<220> FEATURE:
<221> NAME/KEY: Intron2
<222> LOCATION: (1562)..(2564)
<220> FEATURE:
<221> NAME/KEY: Exon3
<222> LOCATION: (2565)..(2806)
<220> FEATURE:
<221> NAME/KEY: Variation
<222> LOCATION: (2807)..(2807)
<223> OTHER INFORMATION: G to A substitution in FucT007
<220> FEATURE:
<221> NAME/KEY: Intron3
<222> LOCATION: (2807)..(3463)
<220> FEATURE:
<221> NAME/KEY: Exon4
<222> LOCATION: (3464)..(3568)
<220> FEATURE:
<221> NAME/KEY: Intron4
<222> LOCATION: (3569)..(4057)
<220> FEATURE:
<221> NAME/KEY: Exon5
<222> LOCATION: (4058)..(4214)
<220> FEATURE:
<221> NAME/KEY: Intron5
<222> LOCATION: (4215)..(4832)
<220> FEATURE:
<221> NAME/KEY: Exon6
<222> LOCATION: (4833)..(5060)
<220> FEATURE:
<221> NAME/KEY: Intron6
<222> LOCATION: (5061)..(5681)
<220> FEATURE:
<221> NAME/KEY: Exon6
<222> LOCATION: (5682)..(5937)

<400> SEQUENCE: 7
atggcaacag ttattccaat tcaaagatta ccaagatttg aaggtgttgg gtcatcatca        60
cctacaaacg caccccaaaa gaaatggtcc aattggctac ctctagtagt tggacttgtg       120
gttttagtgg aaattgcatt tctgggtcga ttggacatgg ctgaaaaagc caacctagtc       180
aactcttgga ctgactcatt ttaccagttt acgacgtcgt cttggtcaac ctccaaagtg       240
gaaattaatg aggctgggtt gggtgtgttg aggagtagtg aggttgatca gaatttggaa       300
actgggagct gtgaggagtg gttggaaaag gaggattctg tggagtattc tagagatttt       360
gataaagatc caattttttgt tcatggcggc gaaaaggtga gatagtttct tgtatatgtt       420
tattcttttt actaataaat ggggtgaata gagcagaatg aatatagagg attcatatag       480
ttgaacacga atagtttggg aagttctatg cactaaacaa tgtaatagtt tttgtttttt       540
ttaatgatga gtgaagggga gctttggtgt aacgattaaa gttgttgcca tgtgacctct       600
cgggctcgag ccgtgcaaac agtctctcgc agaaatgcag ggtaaggctg catacaattg       660 accccttgtgg tccggtcctt ccatggaccc cgcacatagc gggagcttag cgcatcgggc       720 tgccttttttg atgatgggtc taagttctat gcactaacga tataaaaaag atttacacca       780
tcaactcact taaaaggtag tagcagctaa ttctccatag aaacattaat tggtaaacga       840
gcatcccttt tagactataa tatggattgt ttgcaattta tgtcttgtta tttattacat       900
cagttagctg ccagaactcg cgcgcgtgtg tgttccaggc ttatcgcttt ggtagatgga       960
atgataaaaa tttgttattt caatgatgc tttggcattt tcatctagtt tttttttatct      1020 tccatgatgt ttacagtgac atatcttata aagtacagaa tattttgacc atatttcaga      1080
acctcttcat tatgggtaaa aatactgata aattttacat acaagtggga atgagtggag      1140
gagtcttgag tatcttcttt tctcttgcct gtgttccttc attacatcga attcttcata      1200
```

```
gagcacttaa gtggaatgag cagaaatcaa tcagtaaaac tgccatttat tgcttaagtt    1260
tatcatgact agttcttgtt cccatgttat ccactggcat gacggtgaga gcaggtaaca    1320
gtacccggtt accatctttc ttcttgactt tttttccctt accatatgcg aaaactgatg    1380
ttccttcaat cattatctag gattggaagt cttgtgccat aggatgtaac tttggtgtgg    1440
attctgataa gaagcctgac gcggcatttg ggacaccaca acagactggc acagctagcg    1500
tgcttcggtc aatggagtct tctcaatact atcctgagaa caacatcgtt accgcacgac    1560
ggtgggtaag cacatcttga aaaagactta aaacattctc accacatttg gcacctgaaa    1620
gataatagca tttgtccaca tttgaatttt catcttgtgt tcattttcta atgaaacata    1680
tctcacttgg aagcaatgtt atcctaggcg aaaagcgcaa aaaactctaa ggcccattag    1740
agctttaagt gcaaagcgta aaaagtaaaa aatatgtata tgtagtccaa gactaataat    1800
tataagcatg aataacacaa ggaataaaga ccagatactc caagaaagat tacgatgcat    1860
cgggagatga ctaacagatt cacatagaca atcctgattt gaaaccacaa ctgaacacag    1920
ttggttataa atctgtaact aaacgttcat taccatctat cagtccaaag cttgactttc    1980
ctaccatttt caacttcttg ttttatgttt gtctttgaac tgtccccaga aattagctat    2040
tggtctccac aaagcaacct catacagaat acttactggt tttggatcct aatatctctc    2100
catgccataa atcgacttaa taatccttcc atactgcata ttttccatcg ttacaaaaag    2160
aagcagttgc atttgctcaa atagcctttg gaaagggcat atacaaatat gcaatcataa    2220
agccctcaac aacaataact acaacaacaa cccagtaaaa tcccacaact gggtctggct    2280
agggtagtag gtacacaaac cttaccccta ctccgaggga gtagagaggt tgtttccgat    2340
agaccctcga ctcaagaaga tgaaaagaga tgatatatca gtaccataac agaaaatcat    2400
agagataata acagcaatca taaagccctc atagacacaa taaccttagg atcatggtgt    2460
ggttataatt taattttttag atctcctata gttcttctct cgatctttat atctttctct    2520
agggaaatct ctaaccaact ttattatttt ttctcatgtt tcagaagggg atatgatatt    2580
ataatgacaa caagcctctc ttcagatgtt cctgttgggt acttctcttg ggcggagtac    2640
gatataatgg ctccggtgca acctaaaact gagaatgcat tagcagctgc ttttatttct    2700
aattgtggtg ctcgcaactt ccggttgcag gctcttgaag tccttgaaag gcaaatatc     2760 aagattcatt cttttggcag ttgtcatcgt aaccgggatg gaaatggtca gtgtatctcc    2820
attatatatg ataatatatt aatggttctt tccttgaagt agttaccatt aaggagctga    2880
ttgtctaaaa tatttcaata taatgggttt ttgaaaagcc atgttactg gtaatagaaa     2940 ccttatattt gtttccttgg taaatgtaca catacacatg taagttttct aaatagtcag    3000
attttctgct agtttgaaga tttcattatg tggattggtt atttgctgt tatgcttgtt     3060 atcttttgaa taacttctag tattttgcaa cccattaaat tgagttgaaa agcagacagt    3120
ttttgcaaat tcattgcaaa caattagac cctaatttgt tagaaaagaa aaatttagag      3180
aaaattcagt tttagtttat ttttctgatg tagaatatgc atgcatgtgg ttaaacttta    3240
cattatatga atttattaga atagagatga aaatcagaca tcttttgtaa atttattgtg    3300
aagaagctag accagggttt gttggaaagg gaaattaaga gaaaaggcag tcttaataaa    3360
tgtgatatta gaatgcagaa tacttttatt catgcctcta gtttaattgt acattatatc    3420
ctgtgaatgc tcacttgtca tcttgttctc aatttcatgg cagtgacaa agtggaaact     3480 ctcaagcact acaaatttag cttcgctttt gagaattcta atgaggagga ttatgtcacc    3540
```

```
gaaaaattct tccagtcttt agtagctggt aataatttt gcctattaat tttggttctg   3600
ctctttacac ttactttccg atgtatctat tattttctat tagcccccac ccctctgcat   3660
tgatgcattt tttttacttt ttctacaatt cataatttta cccaaaagac ataggagata   3720
ttatctatag agcgccacga agaacaaagc aaaagcacaa acctctgagc actttatgtt   3780
acttcaacta cgttttgtac ccgaatttgc attttctggt acggttcaca aatatgctct   3840
gctctatatt catttaaaag ctttaggaa aattttaaat gattttcgt gaagtatcat    3900 tgttaatcat attatttgtg ctcctagtag atatatatta ggctagagct atgcacagaa   3960
tccttttttt atgattttc acaagttaat acaaaattat gatttatggt agtcaacact    4020
attgtgctga taaaggaag ttcttgtaaa cttgcaggat cagtccccgt ggtgattggt    4080
gctccaaaca tcctagactt tgctccttct cctacttcac ttttacacat aaagagctg    4140 aaagacggtg catcagttgc caagactatg aagtaccttg cagaaaatcc tagtgcatat   4200
aatgagtcat taaggtatgc atcaattagt cgtgctcttc ttgatcattt tgaattttct   4260
tgtcctaaat taacttttgt tgtttgtcct gaagattat ccactctaaa aaaaaaaaac    4320 ccttttttcca acatctttct atactttct gttatcatgt tattgagaaa gtaacactgg   4380
catgtctcta tagttacaaa agtttattac cttatcctat tttatgacac actgatagtc   4440
tgttatatag ttttcgtcta actaaaactc ctaaattggg aagatttgtt ttgtgtgtgt   4500
gagtgtgtgt tcccttctgc atatgtggac ttgcatttga ccctttttt tatgaccgag   4560 aaatccgtct aggactgatc cttttgacca accgcagcct tcgaaactcg gtggataata   4620
ggcccgcccc tctatccttc tccacttaaa taccgggctt tgcttttgct tggtgtgggg   4680
gcttgaacct gtgacttaag acacaaatcc tcctcccttt gccacttgag ctaggccgtg   4740
ggagcagttg cattcgacct tttcctttca aatttattaa agattcttac ttcctgggtc   4800
ttgctaacaa atggtttctt ttcattgttt aggtggaaat ttgagggtcc atctgactct   4860
ttcaaagccc tggttgacat ggcagcagtt cactcttctt gtcgtttgtg tatcttctta   4920
gcaactagta ttagggagaa agaagagaag agtccaaaat ttacgaaacg tccctgcaaa   4980
tgtaccagag gttcagaaac tgtctatcat gtatatgtac gtgaaagagg gaggtttgac   5040
atggagtccg ttttcctaag gtattctcga tcaaccatga ctaaatatca tgcatataca   5100
agtgcctttt ctgtttatgt tcctgtgccg cttttcttat gtttaatatg taccatgatg   5160
atcaaattgt ttaccaatat tggaatgaaa aggatccgaa aagagtggaa tgtatataga   5220
gaattcatag agctgaccgc aaatagggg gagacattga tcaaattatt tgagtaacta   5280
ttcactgtgt cttactctcg atgtatgaga agtatatgct tgatagccat tatctatggg   5340
cttataaagt aatttacatg tttgtggttg ggtattccac aaaatcaatg tcaatctatc   5400
taaagtattt cttgatcgat ttgatagact taactaggga agttccagaa aatgattggc   5460
aggtggtgtt tggttcacta gtaaagctag aagatagggc tggggagggt taaagttggg   5520
gggatccggc cgcaaaaaag aaatatggac aaccagtgtc ataatgtgaa ttctctcctg   5580
cacttctcct tttaattgct gagcatatac aaactgtttc gtgtcttatt ggcaattctt   5640
atgttatgtt tgaatcatcg ttattgctgg aaccttttgca ggtcatctaa tttgtcactg   5700
gaggcttttg aatctgcagt actgtcgaag ctcaaatctc taaagcatgt tcctatttgg   5760
aaagacgaaa gacctcaaat acttcatgga ggggatgaac taaagctcta cagaatatat   5820
cctcttggca tgacacaacg acaggcattg tacacctttta aattcaaagg agacgcagat   5880
tttaggaatc acatcgaaag ccacccatgc gcaaactttg aagccatatt tgtatag      5937
```

<210> SEQ ID NO 8
<211> LENGTH: 1545
<212> TYPE: DNA
<213> ORGANISM: Nicotiana benthamiana
<220> FEATURE:
<221> NAME/KEY: CDS
<222> LOCATION: (1)..(1545)

<400> SEQUENCE: 8

| | | | | | | | | | | | | | | | | |
|---|---|---|---|---|---|---|---|---|---|---|---|---|---|---|---|---|
| atg | gca | aca | gtt | att | cca | att | caa | aga | tta | cca | aga | ttt | gaa | ggt | gtt | 48 |
| Met | Ala | Thr | Val | Ile | Pro | Ile | Gln | Arg | Leu | Pro | Arg | Phe | Glu | Gly | Val | |
| 1 | | | | 5 | | | | | 10 | | | | | 15 | | |
| ggg | tca | tca | tca | cct | aca | aac | gca | ccc | caa | aag | aaa | tgg | tcc | aat | tgg | 96 |
| Gly | Ser | Ser | Ser | Pro | Thr | Asn | Ala | Pro | Gln | Lys | Lys | Trp | Ser | Asn | Trp | |
| | | | 20 | | | | | 25 | | | | | 30 | | | |
| cta | cct | cta | gta | gtt | gga | ctt | gtg | gtt | tta | gtg | gaa | att | gca | ttt | ctg | 144 |
| Leu | Pro | Leu | Val | Val | Gly | Leu | Val | Val | Leu | Val | Glu | Ile | Ala | Phe | Leu | |
| | | 35 | | | | | 40 | | | | | 45 | | | | |
| ggt | cga | ttg | gac | atg | gct | gaa | aaa | gcc | aac | cta | gtc | aac | tct | tgg | act | 192 |
| Gly | Arg | Leu | Asp | Met | Ala | Glu | Lys | Ala | Asn | Leu | Val | Asn | Ser | Trp | Thr | |
| 50 | | | | | 55 | | | | | 60 | | | | | | |
| gac | tca | ttt | tac | cag | ttt | acg | acg | tcg | tct | tgg | tca | acc | tcc | aaa | gtg | 240 |
| Asp | Ser | Phe | Tyr | Gln | Phe | Thr | Thr | Ser | Ser | Trp | Ser | Thr | Ser | Lys | Val | |
| 65 | | | | 70 | | | | | 75 | | | | | 80 | | |
| gaa | att | aat | gag | gct | ggg | ttg | ggt | gtg | ttg | agg | agt | agt | gag | gtt | gat | 288 |
| Glu | Ile | Asn | Glu | Ala | Gly | Leu | Gly | Val | Leu | Arg | Ser | Ser | Glu | Val | Asp | |
| | | | | 85 | | | | | 90 | | | | | 95 | | |
| cag | aat | ttg | gaa | act | ggg | agc | tgt | gag | gag | tgg | ttg | gaa | aag | gag | gat | 336 |
| Gln | Asn | Leu | Glu | Thr | Gly | Ser | Cys | Glu | Glu | Trp | Leu | Glu | Lys | Glu | Asp | |
| | | | 100 | | | | | 105 | | | | | 110 | | | |
| tct | gtg | gag | tat | tct | aga | gat | ttt | gat | aaa | gat | cca | att | ttt | gtt | cat | 384 |
| Ser | Val | Glu | Tyr | Ser | Arg | Asp | Phe | Asp | Lys | Asp | Pro | Ile | Phe | Val | His | |
| | | 115 | | | | | 120 | | | | | 125 | | | | |
| ggc | ggc | gaa | aag | gat | tgg | aag | tct | tgt | gcc | ata | gga | tgt | aac | ttt | ggt | 432 |
| Gly | Gly | Glu | Lys | Asp | Trp | Lys | Ser | Cys | Ala | Ile | Gly | Cys | Asn | Phe | Gly | |
| 130 | | | | | 135 | | | | | 140 | | | | | | |
| gtg | gat | tct | gat | aag | aag | cct | gac | gcg | gca | ttt | ggg | aca | cca | caa | cag | 480 |
| Val | Asp | Ser | Asp | Lys | Lys | Pro | Asp | Ala | Ala | Phe | Gly | Thr | Pro | Gln | Gln | |
| 145 | | | | 150 | | | | | 155 | | | | | 160 | | |
| act | ggc | aca | gct | agc | gtg | ctt | cgg | tca | atg | gag | tct | tct | caa | tac | tat | 528 |
| Thr | Gly | Thr | Ala | Ser | Val | Leu | Arg | Ser | Met | Glu | Ser | Ser | Gln | Tyr | Tyr | |
| | | | | 165 | | | | | 170 | | | | | 175 | | |
| cct | gag | aac | aac | atc | gtt | acc | gca | cga | cga | agg | gga | tat | gat | att | ata | 576 |
| Pro | Glu | Asn | Asn | Ile | Val | Thr | Ala | Arg | Arg | Arg | Gly | Tyr | Asp | Ile | Ile | |
| | | | 180 | | | | | 185 | | | | | 190 | | | |
| atg | aca | aca | agc | ctc | tct | tca | gat | gtt | cct | gtt | ggg | tac | ttc | tct | tgg | 624 |
| Met | Thr | Thr | Ser | Leu | Ser | Ser | Asp | Val | Pro | Val | Gly | Tyr | Phe | Ser | Trp | |
| | | 195 | | | | | 200 | | | | | 205 | | | | |
| gcg | gag | tac | gat | ata | atg | gct | ccg | gtg | caa | cct | aaa | act | gag | aat | gca | 672 |
| Ala | Glu | Tyr | Asp | Ile | Met | Ala | Pro | Val | Gln | Pro | Lys | Thr | Glu | Asn | Ala | |
| 210 | | | | | 215 | | | | | 220 | | | | | | |
| tta | gca | gct | gct | ttt | att | tct | aat | tgt | ggt | gct | cgc | aac | ttc | cgg | ttg | 720 |
| Leu | Ala | Ala | Ala | Phe | Ile | Ser | Asn | Cys | Gly | Ala | Arg | Asn | Phe | Arg | Leu | |
| 225 | | | | | 230 | | | | | 235 | | | | | 240 | |
| cag | gct | ctt | gaa | gtc | ctt | gaa | agg | gca | aat | atc | aag | att | cat | tct | ttt | 768 |
| Gln | Ala | Leu | Glu | Val | Leu | Glu | Arg | Ala | Asn | Ile | Lys | Ile | His | Ser | Phe | |
| | | | | 245 | | | | | 250 | | | | | 255 | | |
| ggc | agt | tgt | cat | cgt | aac | cgg | gat | gga | aat | gtg | gac | aaa | gtg | gaa | act | 816 |
| Gly | Ser | Cys | His | Arg | Asn | Arg | Asp | Gly | Asn | Val | Asp | Lys | Val | Glu | Thr | |
| | | | 260 | | | | | 265 | | | | | 270 | | | |

| | | | | | | | | | | | | | | | | |
|---|---|---|---|---|---|---|---|---|---|---|---|---|---|---|---|---|
| ctc | aag | cac | tac | aaa | ttt | agc | ttc | gct | ttt | gag | aat | tct | aat | gag | gag | 864 |
| Leu | Lys | His | Tyr | Lys | Phe | Ser | Phe | Ala | Phe | Glu | Asn | Ser | Asn | Glu | Glu | |
| | | | | 275 | | | | | 280 | | | | | 285 | | |
| gat | tat | gtc | acc | gaa | aaa | ttc | ttc | cag | tct | tta | gta | gct | gga | tca | gtc | 912 |
| Asp | Tyr | Val | Thr | Glu | Lys | Phe | Phe | Gln | Ser | Leu | Val | Ala | Gly | Ser | Val | |
| | 290 | | | | | 295 | | | | | 300 | | | | | |
| ccc | gtg | gtg | att | ggt | gct | cca | aac | atc | cta | gac | ttt | gct | cct | tct | cct | 960 |
| Pro | Val | Val | Ile | Gly | Ala | Pro | Asn | Ile | Leu | Asp | Phe | Ala | Pro | Ser | Pro | |
| 305 | | | | | 310 | | | | | 315 | | | | | 320 | |
| act | tca | ctt | tta | cac | att | aaa | gag | ctg | aaa | gac | ggt | gca | tca | gtt | gcc | 1008 |
| Thr | Ser | Leu | Leu | His | Ile | Lys | Glu | Leu | Lys | Asp | Gly | Ala | Ser | Val | Ala | |
| | | | | 325 | | | | | 330 | | | | | 335 | | |
| aag | act | atg | aag | tac | ctt | gca | gaa | aat | cct | agt | gca | tat | aat | gag | tca | 1056 |
| Lys | Thr | Met | Lys | Tyr | Leu | Ala | Glu | Asn | Pro | Ser | Ala | Tyr | Asn | Glu | Ser | |
| | | | 340 | | | | | 345 | | | | | 350 | | | |
| tta | agg | tgg | aaa | ttt | gag | ggt | cca | tct | gac | tct | ttc | aaa | gcc | ctg | gtt | 1104 |
| Leu | Arg | Trp | Lys | Phe | Glu | Gly | Pro | Ser | Asp | Ser | Phe | Lys | Ala | Leu | Val | |
| | | 355 | | | | | 360 | | | | | 365 | | | | |
| gac | atg | gca | gca | gtt | cac | tct | tct | tgt | cgt | ttg | tgt | atc | ttc | tta | gca | 1152 |
| Asp | Met | Ala | Ala | Val | His | Ser | Ser | Cys | Arg | Leu | Cys | Ile | Phe | Leu | Ala | |
| | 370 | | | | | 375 | | | | | 380 | | | | | |
| act | agt | att | agg | gag | aaa | gaa | gag | aag | agt | cca | aaa | ttt | acg | aaa | cgt | 1200 |
| Thr | Ser | Ile | Arg | Glu | Lys | Glu | Glu | Lys | Ser | Pro | Lys | Phe | Thr | Lys | Arg | |
| 385 | | | | | 390 | | | | | 395 | | | | | 400 | |
| ccc | tgc | aaa | tgt | acc | aga | ggt | tca | gaa | act | gtc | tat | cat | gta | tat | gta | 1248 |
| Pro | Cys | Lys | Cys | Thr | Arg | Gly | Ser | Glu | Thr | Val | Tyr | His | Val | Tyr | Val | |
| | | | | 405 | | | | | 410 | | | | | 415 | | |
| cgt | gaa | aga | ggg | agg | ttt | gac | atg | gag | tcc | gtt | ttc | cta | agg | tca | tct | 1296 |
| Arg | Glu | Arg | Gly | Arg | Phe | Asp | Met | Glu | Ser | Val | Phe | Leu | Arg | Ser | Ser | |
| | | | 420 | | | | | 425 | | | | | 430 | | | |
| aat | ttg | tca | ctg | gag | gct | ttt | gaa | tct | gca | gta | ctg | tcg | aag | ctc | aaa | 1344 |
| Asn | Leu | Ser | Leu | Glu | Ala | Phe | Glu | Ser | Ala | Val | Leu | Ser | Lys | Leu | Lys | |
| | | 435 | | | | | 440 | | | | | 445 | | | | |
| tct | cta | aag | cat | gtt | cct | att | tgg | aaa | gac | gaa | aga | cct | caa | ata | ctt | 1392 |
| Ser | Leu | Lys | His | Val | Pro | Ile | Trp | Lys | Asp | Glu | Arg | Pro | Gln | Ile | Leu | |
| | 450 | | | | | 455 | | | | | 460 | | | | | |
| cat | gga | ggg | gat | gaa | cta | aag | ctc | tac | aga | ata | tat | cct | ctt | ggc | atg | 1440 |
| His | Gly | Gly | Asp | Glu | Leu | Lys | Leu | Tyr | Arg | Ile | Tyr | Pro | Leu | Gly | Met | |
| 465 | | | | | 470 | | | | | 475 | | | | | 480 | |
| aca | caa | cga | cag | gca | ttg | tac | acc | ttt | aaa | ttc | aaa | gga | gac | gca | gat | 1488 |
| Thr | Gln | Arg | Gln | Ala | Leu | Tyr | Thr | Phe | Lys | Phe | Lys | Gly | Asp | Ala | Asp | |
| | | | | 485 | | | | | 490 | | | | | 495 | | |
| ttt | agg | aat | cac | atc | gaa | agc | cac | cca | tgc | gca | aac | ttt | gaa | gcc | ata | 1536 |
| Phe | Arg | Asn | His | Ile | Glu | Ser | His | Pro | Cys | Ala | Asn | Phe | Glu | Ala | Ile | |
| | | | 500 | | | | | 505 | | | | | 510 | | | |
| ttt | gta | tag | | | | | | | | | | | | | | 1545 |
| Phe | Val | | | | | | | | | | | | | | | |

<210> SEQ ID NO 9
<211> LENGTH: 514
<212> TYPE: PRT
<213> ORGANISM: Nicotiana benthamiana

<400> SEQUENCE: 9

Met Ala Thr Val Ile Pro Ile Gln Arg Leu Pro Arg Phe Glu Gly Val
1               5                   10                  15

Gly Ser Ser Ser Pro Thr Asn Ala Pro Gln Lys Lys Trp Ser Asn Trp
                20                  25                  30

Leu Pro Leu Val Val Gly Leu Val Val Leu Val Glu Ile Ala Phe Leu

```
                35                  40                  45
Gly Arg Leu Asp Met Ala Glu Lys Ala Asn Leu Val Asn Ser Trp Thr
 50                  55                  60
Asp Ser Phe Tyr Gln Phe Thr Thr Ser Ser Trp Ser Thr Ser Lys Val
 65                  70                  75                  80
Glu Ile Asn Glu Ala Gly Leu Gly Val Leu Arg Ser Ser Glu Val Asp
                 85                  90                  95
Gln Asn Leu Glu Thr Gly Ser Cys Glu Glu Trp Leu Lys Glu Asp
                100                 105                 110
Ser Val Glu Tyr Ser Arg Asp Phe Asp Lys Asp Pro Ile Phe Val His
                115                 120                 125
Gly Gly Glu Lys Asp Trp Lys Ser Cys Ala Ile Gly Cys Asn Phe Gly
                130                 135                 140
Val Asp Ser Asp Lys Lys Pro Asp Ala Ala Phe Gly Thr Pro Gln Gln
145                 150                 155                 160
Thr Gly Thr Ala Ser Val Leu Arg Ser Met Glu Ser Ser Gln Tyr Tyr
                165                 170                 175
Pro Glu Asn Asn Ile Val Thr Ala Arg Arg Gly Tyr Asp Ile Ile
                180                 185                 190
Met Thr Thr Ser Leu Ser Ser Asp Val Pro Val Gly Tyr Phe Ser Trp
                195                 200                 205
Ala Glu Tyr Asp Ile Met Ala Pro Val Gln Pro Lys Thr Glu Asn Ala
                210                 215                 220
Leu Ala Ala Ala Phe Ile Ser Asn Cys Gly Ala Arg Asn Phe Arg Leu
225                 230                 235                 240
Gln Ala Leu Glu Val Leu Glu Arg Ala Asn Ile Lys Ile His Ser Phe
                245                 250                 255
Gly Ser Cys His Arg Asn Arg Asp Gly Asn Val Asp Lys Val Glu Thr
                260                 265                 270
Leu Lys His Tyr Lys Phe Ser Phe Ala Phe Glu Asn Ser Asn Glu Glu
                275                 280                 285
Asp Tyr Val Thr Glu Lys Phe Phe Gln Ser Leu Val Ala Gly Ser Val
                290                 295                 300
Pro Val Val Ile Gly Ala Pro Asn Ile Leu Asp Phe Ala Pro Ser Pro
305                 310                 315                 320
Thr Ser Leu Leu His Ile Lys Glu Leu Lys Asp Gly Ala Ser Val Ala
                325                 330                 335
Lys Thr Met Lys Tyr Leu Ala Glu Asn Pro Ser Ala Tyr Asn Glu Ser
                340                 345                 350
Leu Arg Trp Lys Phe Glu Gly Pro Ser Asp Ser Phe Lys Ala Leu Val
                355                 360                 365
Asp Met Ala Ala Val His Ser Ser Cys Arg Leu Cys Ile Phe Leu Ala
                370                 375                 380
Thr Ser Ile Arg Glu Lys Glu Glu Lys Ser Pro Lys Phe Thr Lys Arg
385                 390                 395                 400
Pro Cys Lys Cys Thr Arg Gly Ser Glu Thr Val Tyr His Val Tyr Val
                405                 410                 415
Arg Glu Arg Gly Arg Phe Asp Met Glu Ser Val Phe Leu Arg Ser Ser
                420                 425                 430
Asn Leu Ser Leu Glu Ala Phe Glu Ser Ala Val Leu Ser Lys Leu Lys
                435                 440                 445
Ser Leu Lys His Val Pro Ile Trp Lys Asp Glu Arg Pro Gln Ile Leu
450                 455                 460
```

His Gly Gly Asp Glu Leu Lys Leu Tyr Arg Ile Tyr Pro Leu Gly Met
465                 470                 475                 480

Thr Gln Arg Gln Ala Leu Tyr Thr Phe Lys Phe Lys Gly Asp Ala Asp
                485                 490                 495

Phe Arg Asn His Ile Glu Ser His Pro Cys Ala Asn Phe Glu Ala Ile
            500                 505                 510

Phe Val

<210> SEQ ID NO 10
<211> LENGTH: 13089
<212> TYPE: DNA
<213> ORGANISM: Nicotiana benthamiana
<220> FEATURE:
<221> NAME/KEY: Exon1
<222> LOCATION: (1)..(396)
<220> FEATURE:
<221> NAME/KEY: Variation
<222> LOCATION: (224)..(224)
<223> OTHER INFORMATION: G to A substitution in FucT009
<220> FEATURE:
<221> NAME/KEY: Intron1
<222> LOCATION: (397)..(8228)
<220> FEATURE:
<221> NAME/KEY: Exon2
<222> LOCATION: (8229)..(8389)
<220> FEATURE:
<221> NAME/KEY: Intron2
<222> LOCATION: (8390)..(9684)
<220> FEATURE:
<221> NAME/KEY: Exon3
<222> LOCATION: (9685)..(9926)
<220> FEATURE:
<221> NAME/KEY: Intron3
<222> LOCATION: (9927)..(10665)
<220> FEATURE:
<221> NAME/KEY: Exon4
<222> LOCATION: (10666)..(10770)
<220> FEATURE:
<221> NAME/KEY: Intron4
<222> LOCATION: (10771)..(11419)
<220> FEATURE:
<221> NAME/KEY: Exon5
<222> LOCATION: (11420)..(11576)
<220> FEATURE:
<221> NAME/KEY: Intron5
<222> LOCATION: (11577)..(11984)
<220> FEATURE:
<221> NAME/KEY: Exon6
<222> LOCATION: (11985)..(12212)
<220> FEATURE:
<221> NAME/KEY: Intron6
<222> LOCATION: (12213)..(12833)
<220> FEATURE:
<221> NAME/KEY: Exon7
<222> LOCATION: (12834)..(13089)

<400> SEQUENCE: 10
atggcaacag ttattccaat tcaaagaata ccaagatttg aaggtgttgg gtcattatca     60
cctacaaacg ttccccaaaa gaaatggtcc aattggttac ctctagtagt tgcacttgtg    120
gttatagttg aaattgcatt tctgggtcga ctggacatgg ctgaaaaagc caacctggtc    180
aactcttgga ctgactcatt ttaccagttt acgacgtcgt cttggtcaac ctccaacgtg    240 gaattaatg aggctgggtt gggtgtgttg aggagtagta aggttgatcg aatttggca    300 actgggagct gtgaggagtg gttggaaaag gaagattctg tagagtattc tagagatttt    360
gacaaagatc caattttgt tcatggcggc gaaaaggtga tatagttttc ttgtaaatgt    420
ttattttttt agagcagaat gaatatgagg attcatttag ttgaaccgga acagtttagg    480

```
aggcatagtt gattgctctt tttctgatga tgagtattta gttctgtaca gaaagggagc    540
cttggagcaa cggtaaagtt gtctccctag gtcacgggtt cgaataatgg aatcagacac    600
gatgcttcca tcagggtagg ctacctacat tatacctctt cgtgcactag actactgtcc    660
tctagtgtta gttctatgca ctaacgatgt aaaaacgatt tacaccataa ggtcacttaa    720
aaggtagtag cagctaattc ttcatagaaa cattaattgg taatcgatca tctcttttag    780
acgataatat cgattttatt gtcatttatg tcttgctatt tattcatca gttagctgcc     840
agagctcgcg cgagtgtgtg tttgttgcag acttatggct ttggtagatg gaatgatgat    900
aatttggtgt ttcaaatgat gctttggcat cattttctag ttttttgttc ttttattatg    960
cctacagtaa aacatcttat aaagtacaga ctattgacca tattccaaaa cctatatggg   1020
taaaaatact catgaatttt atatactagt agggaataag tggaggagcc ttgagtatct   1080
tctcttctct taccttttt ccttcgttat tgttacgacc ccagttcacc ctctatgaac    1140
atgtcgtgat ggcacctagt tcctacaact aggtaagtct aacaatgcgg aaatttaata   1200
taagtatata acttgcggaa catttaatta aattaagcaa aactagaaga aaatgatata   1260
taagtgccac atggcatata caattcaaaa ataaaacgcg gaagtctaaa atctcatccc   1320
aaaacccgaa aactcacggg aacacaagct aacgaatagt aatacatagc tctaactcca   1380
gaatatctaa agcaaaagta cgaaagaagt ctaaatacta caaacaaagt aaagaaggag   1440
actccttggt ttgcgaacgc tgcagaagta cctcaaagtc ttcgtagctc tcctgacctt   1500
aaggatagtg cacttgagat caagtacctg ggtctgcaca tgaaaaacat gtcagtaagt   1560
gccaggccta acctcggttg ggtggttacg atgaaggtta gggccctact gagataaaat   1620
ataataataa ggctaacaac agtattaaat aagcagaaat aatggaatac aattgtgaag   1680
taagttaggt tacacaagca acaatttaac acatagagga taagataaca cagagtaaaa   1740
ttgttcaata ccagtaccaa taacgaggat ctcctaggat accgtcctat agtccttttc   1800
atcaatccgt ccgaggagct cccgggatac cgtcccatag tccatcatat gagtatatcc   1860
gaaggatctc ccgggatacc gtcccatagt ccaactatca atgtataagg ggatctaccg   1920
ggaatctaac ccgtagtccc atagtaaagt gcaggggat ctatcgggaa tcgaacccgc    1980
aatcccaaag taaatatgca ggggatctat cgggaatcga acccgcagtc ccaaagttaa   2040
tatgcagggg gatctatcgg gaattgaacc cgcagtccca agtaaatat gcagggggat    2100
ctatcgagaa tcgaacccgt agtcccaaag taaatatgta gggggatcta tcgggaattg   2160
aactcgcagt cccaaagtaa atacgcagcc accacaaaag atattcagaa ctggggtgca   2220
aaaatacaag gcaataagta gttctcgcct aacatgcttc acatattaca atcaaggcaa   2280
cttaagcaaa taggcaattt aggtcagcta agcatgctta gatcctttag caactctaac   2340
caccttctct ggaacaaatt tagatcattc tgcttgaaca aatgctgcaa actcctatga   2400
tcagaataaa tctcacaagg cacaccgtac aaataatgac gccagatctt caaggcatga   2460
acaatagtag ctaactcaag gttgtggaca gggtaattct tctcatgtat cttcaactgt   2520
ctggacgcgt aggcaatcac cctactgtcc tgcatcaaca ctctccaagg ccaacccgtg   2580
aggcatcaca ataaactgta caagatctcg aaccagtagg caatatcaga ataggggctg   2640
tagtcaaagc tgtcttgagc ttctgaaagc tcgcctgaca ctcccctgtc cactgaaatg   2700
gggcacccTT ctgggtcaac ctagtcatag gggctgcaat cgatgaaaac ccctccacaa   2760
aacgacggta ataacctgcc aagccaagga aattgcgaat ctcagtggct aagcacggcc   2820
tgggccaact ctgcacggcc tctatcttcc tcggatctac ccgaatgccc tcgctcgaaa   2880
```

```
ccacatggcc taagaatgcc actgaatcta accaaaactc acattttgag aacttcgcat    2940
ataacttctt ctccttcagg gtctgaagtg ctgcttatga tcttcccgac tccggtaata    3000
caccagaata tcatcaataa aaacaataat gaatgagtcg agatatcgcc tgaatacact    3060
gtgcatcaaa tgcataaaag ctgctagggc attggtcaac ccaaatgaca taacaaggaa    3120
ctcgtaatga ccataccgag tcctgaaggt agtcttcgag atatctggct cccgaatctt    3180
caactgatgg taacctgagc gcaagtcaat cttagaaaac acctgtgcgc cctgaagctg    3240
gtcaaacaga tcatcaatac gaggcaaagg ataaccgttc ttcacggtaa ccttgtttaa    3300
ctggcaataa tcaatacaca tatgtataga accatccttc ttcttcacaa acaacacagg    3360
agcaccccac agtgaaacac taggtcgaat aaaacccta tcaaacaatt ccggcaactg    3420
atccttcaat tccttcaact caagaggaac catacgatac ggaggaatgg aaatgggctg    3480
agtgcccggt caacaggtca atgccaaaat caatatctct atcaggcggc atgctcggaa    3540
gatcagctag aaacgcatcg ggataatccc gtaccactgg aattgaatca acaaaagggg    3600
tatcggcact aatatctctc acataagcta aatacgtagc acccccttc tcaatcatac     3660
gctgagcttt aagaaaagag ataactcttc tgagagtgtg atctaaagta ccactccact    3720
caacacgcgg aatacctggc atagccagcg tcacggtcct ggcgtgacaa tcaagaatcg    3780
caaaatggag cgacaaccag tccatgccca agataatatc aaaatcaacc atgttgagta    3840
aaaataaatc tgccgtggtc tcaaaaccac gaatagtaac taaacatgac taataaacgc    3900
ggtccacaac aagggaatcc cccacaggag tagaaacata acggggggca ttcaaagaat    3960
cccgaggcac acccaaatgc ggagcaaatt aagaagacac ataagaataa gtgaagcata    4020
gatcgaagag aattggtaca cctctataac aaaccatgaa aaatacttgt gatgatagaa    4080
tcgaaggcaa cagcctcggt acgggtaggt ggggtagcaa ctggggctgt aacgatggca    4140
tgggaacttt gcggggcacg ctgtggccga gaagtctgtg gatgtgcact cctcccaagt    4200
atggggcaat acctcaccac atggcgtatg tccccacact ggaagtagcc tcgcggctga    4260
cgcgatagtg gaaactaagg ggtacgggta ctctgaaacc cctgaacaca tgaagccctg    4320
tgtgaaatct gggatgcaaa ctgagctggc tgacccacaa aacctctacc atgccgtact    4380
cttcctccaa aataaggact agtgggtctc cccaatctgc gaggcctact cattcctcta    4440
tactctccct cctgacctcg tctgtctcct actcggtaag aggttctcac aactcactga    4500
actgggacca catgctgtgt caccatgaca cctggaacct gaccaatgtg aactcgctgc    4560
tctggagtgg gggcggcggg agtctgagtc cctcccctaa cctgtgaagt agtcggtaca    4620
acttgaatca atcctgcctg aatcaatgta ccaaacacgc tcaggaactg tgccaaagtc    4680
tcttgaaagg ctggcgtagt agtagcaggc gtgtcaagtg cctggactcc ggttggatct    4740
gctggtggtg cctcggtgtc agctcgcgca ggtgctctgg ctgcaccacg tgtgcgtcct    4800
cgacctctgc cccggccttg gcctctgacg gctgcagtag aggtgcgggt gcctggcatc    4860
ccgagtagtg cgtgtcccca ccatctgtga gagaattaaa gacagaagtt tagatccgat    4920
gtcaaaaata tctcacgaca aggaaatcaa tgaagtgaag atttttccta aatagttaca    4980
tagcctctcg gaataagtac agacgtctcc gtaccgatca tcgagactct aataaaccgg    5040
cctgtattct gtgactcata tgaacctaga gctctgatac caacttgtca caatcccagt    5100
tcaccctcca tgaacatgtc gtgatggcac ctagttccta caactaggta agcctaacaa    5160
tgtgaaaatt taatataact tgcggaacat taaattaaat taagcaaaac tagaagaaaa    5220
```

```
tgatatataa gtgtcacctg gtatatacaa ctcaaaaata aaatggaagt ctaaaatctc    5280
atcccaaaac ccggaaactc acgggaacac aagctaacga atagtaatac atggctctaa    5340
ctccagaata tctaaagcaa aattatggaa tgagtctcct tggtctgcga acgctgcaga    5400
agtacctcaa agtctcggta gctcttctga cctcaaggat agtgtgcctg agatgaagta    5460
cctctgtctg cacattaaaa gcatgcgcgg aagaggcatg agtacaccac agctgtactc    5520
agtaagtgcc aagcctaacc tcggttgggt ggtgacgagg aaggtcaggg ccctactgag    5580
atagaatata agaataaggc tgacaatagt atgaaataag cagaaataat ggaatacaac    5640
tatgaagtaa gttaggttac acaagtaaca atttaacaca caaggataa gataacacag       5700
agtaaaaccg ctcgatacca gtaccaataa cgaggatctc ccaggatacc atccagtagt    5760
ccttttcatc aatccatccg aggagctccc ggataccgtc ccgtagtcca tcatatgagt    5820
atatccgaat gatctcccgg aataccgttc catagtccaa ctatcaatgt acaggggat       5880
ctaccgggaa tctaacccgt agtccaaaag taaagtgcag ggggatctac cgggaatctt    5940
acccgtagtc ccaaagtaaa gtgtaggggg atctatcggg aatcgaaccc gcagtcccaa    6000
agtaaatatg caggggatct accgggaatc gaacccgcaa tcccaaagta aatatgcagg    6060
gggatctatc gggaatcgaa cccgcaatcc caaattaaat atgcaggggg atctatcggg    6120
aattgaaccc gcagcctcga agtaaatatg caggggatct accggaaatt gaatccgcac    6180
tcccaaagta aatacgcagc cacaacaaaa gatattcaga accagggtgc taaaatacaa    6240
ggcaacaagt agttctagcc aaacatgttt cacgtagtac aatcaaggca acttaagcaa    6300
ataggcaatt taggttagct tagcatactt tcctagacta acatggctat aatggcaggt    6360
agaacgacac atgctataat ggcaagtaga gtaacacatg ctataatggc aagtagaata    6420
aagcaggtag gaaagaaact cagtctaaat atttaaagta aaactggatt tccgacaatt    6480
agctcgagta cgcgctcgtc acctcacgta caaggcattc aatcaccaga tatcatatcc    6540
taagggaaa ggtccccgac acaaggttag acaagccact ggctccaaat tcaacttgaa     6600
atcacacttt tgccacgagt atccgttttcc aaatggccca aatctattca attcaattac    6660
atatcgtaaa taacatctca aataattgat tttactattt agttcaatga taaaacgcga    6720
aattaggtaa aatgaccaaa acgcccctca gaacaccgtc tcggaatcgg ataattttta    6780
tattttcaga accctcgtac tctcacgagt ctaaccatat gaaaatctcc caaatcgaag    6840
gtgaaacacc ccctcaaaac tcaataattc ggtctatgaa gttatacccca ttttttcatta    6900
aaaatttgaa attaaaggac gaaattaaga ggagatttat ggaaattggt ctaaaatcga    6960
gtgagaaaca cttatccaag tcgcccaggt gaaaatccct tcaaaaatcg ccaaaaaccg    7020
agctctagaa gtcaaaatgt gataaaatgg tgaaaccctc gaatttggga ttaattctgt    7080
ctgcccagtg gtttgtccta tccgatcgcg agccaaacaa tgcgatcgca tagaaggaaa    7140
aatattgttg ccaaatttgt tctatgcgat cgcgggcaaa tcaatgcgat cgcatagaag    7200
gaatttgttg ccaaatttgt tttatgcgat catgggcaaa tcaatgcgat cgcatagaag    7260
gaaaaatatt gttgccaaat tgttctatg cgatcgcggg aaaaacaatg caatcgtata    7320
gaaggaaata ccagatagca gaataacagt tcaaacatag gaaaaaaatg agccgtagcc    7380
catccggaac gcacccgagg cccccaggac ctcaaccaaa cctacggaca tatcccataa    7440
catcattcaa acttgcacca atccttaagc cacctaaaac gtcggaaact cgaattaatc    7500
aatgttttga gcctaagaac ttcaattttc atcgaaacat gctttcgatc aaaaacctaa    7560
ccgaaatacg tccgaatgac ctgaaatttt gcacacacat cccaaataac atgacggagc    7620
```

```
tactgcaact tctggattta cgttctgact ttcggatcaa aaactcacta tcagaccgga    7680
aacttaaaaa tttcaaactt cggcatttca agcctaaatg agctacggac ttccaaaatg    7740
cattcgaaac acgctcccaa ccccgaaatc acctaacgga gctaacggaa ccatcggatt    7800
cccattccga ggtcgtcttc acattcttcc gactacgaac cactttccaa cacttacgct    7860
ctcttttaga gacttaagtg tcccaaaact ctttgaaacc caacaccgaa cgtcccggca    7920
aaccaaaata gcatagacaa acttagggga agcagttaat ggggatcggg gcgtaatttc    7980
cgaaaaacga ccgaccgggt cgtcgcaatt acattgaatt cttcatagag cacttaagtg    8040
gaatgagcag aaatcaatca gtaaaactgc catttactgc ttaagtttat aatgactagt    8100
tcttgttccc atgttatcca ctggtatata ggtgagagca ggtaaccagt acccggttat    8160
catctttctt cttgattttt ttttccttac catatgcgaa aactgatgtt ccttcaatca    8220
ttatctagga ttggaagtct tgtgcagtag gatgtaactt tggtgtggat tctgataaga    8280
agcctgatgc ggcatttggg acaccacaac aggctggcac ggctagcgtg cttcggtcaa    8340
tggagtctgc tcaatactat ccggagaaca acatcgttac cgcacgacgg tgggtaagca    8400
catcttgaaa aaggcttaaa acattctcac cacatttgga acctgaaaga taatagcatt    8460
tgtccacatt tgaattttca tcttgtgatc attttttaat gaaacatatt tcacttggca    8520
gtttttgatt gcaattagtt cctgactgga cctttttttct ttggataagt aaggtagcat    8580
aatattagta actagtaagc agtaccaaga aagtacaaaa attgatactt ccaaagtcta    8640
ctcaaaacct gaatccagcg actccaagaa ctcatttgta ctaactacaa gatctgtttt    8700
atgccggcaa aagagatact gtaaacatct atacttcata aatataatct cctcattttc    8760
cccctcaaaa tatctcatat ttcttttctag ccaaaccgtc aaaacaatgc acgaaataag    8820
cttccagtta ttcttcactc ttttctccac tgtgcttgcc agcttatgag cgcatctccg    8880
aagttttgcg gcattatcca gtattacacc caaaatatat tttttatcag gataccctct    8940
aaatattaag gaataatgac cagatactcc aagaaagatt cgatgcatc atgagatgac    9000 taacagattc acatagtcaa tcctgatttg aaaccacaac tgaacacagt tgggaataaa    9060
tctgtaagta agcttgcatt acaccatcta tcagtccaaa gcttgacttc cctaccattt    9120
tcaacgtttt gttttatgtt tgtctttgaa ctgtccccag aaattagcta ttgatctcca    9180
caaagcaacc tcatatggat tacttactgg ttttggatcc taatatctct ccatgccata    9240
aattgactta ataacagcct tccataatcc atactgcata ttttccatcg ttacgaaaaa    9300
aagcattcac atttgctcaa atagcctttg gaaggggcat ctacaaatat gcaatcataa    9360
agccctcaac aacaataatt acaacaacaa ccaagtaaaa tcccacaatt ggggtctggg    9420
gagggtagtg tgtacgcaaa ccttacctct aactccgata gaccctcggc tcaagaatat    9480 gaaagagac aatatataag taccatcaac aaaaaatcat agagataata acagcaatca    9540
taaagccctc atagacacaa taaccttagg atcatgttgt ggttataatt taatctttag    9600
atctcctata gttcttctct caatctttat atctttctct agggaaatct ctgaccaact    9660
ttattattct ttttcatgtt tcagaagggg atatgatatt gtaatgacag caagcctctc    9720
ttcggatgtt cctgttgggt acttctcttg ggcggagtat gatataatgg ctccagtgca    9780
acctaaaact gagaatgcat tagcagctgc ttttatttct aattgtggtg cttgcaactt    9840
ccggttgcag gctcttgaag tccttgaaag ggcaaatatc aagattgatt cttttggcag    9900
ttgtcatcgt aaccgggacg gaaatggtca gtatctccat tatatatgat aatatattga    9960
```

```
tggttctttt cttgaagtag ttaccattaa ggagctaatt gtctaaaata tttcaatata   10020
atgggttttt gaaaagccat gtttactggt aatagaaacc ttacagtatt tatttccttg   10080
gtaaatgtac acatacacat gtaagtgttc taaatagtca gatgttctgc tagtttgaag   10140
atttcatttt gtggattggt tatattgctg ttacgcttgt tatcttttga atacctcctt   10200
agtattttgc aacccattaa attgggttga aaagcagcag ttttttgcaaa ttcattgcaa   10260
agaaattaga ccctaatttg ttataataga aaaatttaaa caaaatttag ttttagttta   10320
ttcttctgat gtagaatatg catgcctgtc gtttgacttt acattatacg taaatttatt   10380
agaatagagt tgaaaagcag acattttttc taaattaaac cacgtgcatg cataaaaaat   10440
gtctgttttg caacttacta ggatatagtt gaaagcagac atcttttttgt aaatttattg   10500
tgaagaagct agaccaggtt tgttggaaag ggaaattaag agaaaaggca tttcttaata   10560
aatgtcatat tacaatgcag aatatttttta tccatgcctc tagtttaatt gtacattata   10620
tcctgtgaat gcttacttgt catcttgttc tcaatttcat ggcagtggac aaagtggaaa   10680
ctctcaagtg ctacaaattt agcttcgctt ttgagaattc taatgaggag gattatgtca   10740
ccgaaaaatt cttccagtct ttagtagctg gtaataattt ttgcctgtta attttggttc   10800
tgcattttac acttagtttc caatgtatct attcttttct attaacccccc tcccctctgc   10860
attgatgcat tttgttttac tttttctgca attcataatt acacaaaaga cataggagat   10920
attagctata gagcgccatg aagaacaaag caaaaagcac aaacttttttt ttttatgacc   10980
aagaaatccg tctggggccg atcctttgga ccaaatgcaa ccttcgaaat tcggtggata   11040
atgggacctc ccctctatcg ttctccactt aaatgccagg ctttgctttg catggtgtgg   11100
gggcaagcga aaagcacaaa cttctgaaca ctttatgtta cttcaactac gttttgtacc   11160
cgaatttgca ttttctggta cgacgtacaa atatgctctg ctctatattc atttaaaagg   11220
ctttaggaaa atgttaaatg attttacgtg aattatcatt gttaataata ttctttgtgc   11280
tcctagtcaa tatgttttag ggtagaatta tgcacggaat cctgttttta tgattttca    11340
caagttacta cttcaaaatt atgatttatg gtagtcaacg ctattgtgct gataaaagga   11400
agttcatgta aacttgcagg atcagtcccc gtggtgattg gtgctccaaa catcctagac   11460
tttgctcctt ctcctaattc acttttacac attaaagagc tgaaagacgc tgcatcagtt   11520
gccaagatta tgaagtacct tgcagaacat cctagtgcat ataacgagtc attaaggtat   11580
gcatcaattt gtcgtgcttt tcttacgtgc tcttcttgat tatttgaatt ttcctgtcct   11640
aaattaactt ttttttgtttg tcctgaagat ttatccactc tctctaaaaa aaacccctt    11700
ttccaacatc tttctgtact tttctgttat catgttattg agagagtaac actggcctgt   11760
ctctatggtt gcaaaagttt attaccttat cctattttat gacactttaa tatatagttt   11820
tggtctaact aaaactccta aattagtaag attgttctct gtgtgtgagt ttgtgtcccc   11880
ttctgcatgt gtggacttgc atttgacctt tgcctttcaa aatttattta agattcttaa   11940
acttcctggg tcttgctaac aaatggtttc ttttcattgt ttagttggaa atttgagggt   12000
ccatctgact cgttcaaagc cctggttgac atggcagcag ttcactcttc ttgtcgtttg   12060
tgtatcttct tagcaactag tattagggag aaagaagaga agagtccaaa atttacgaaa   12120
cgtccctgca aatgtaccag aggttcagaa actgtctatc atgtatatgt acgtgaaaga   12180
gggaggtttg acatggagtc cgttttccta aggtattttc gatctgccat gactaaatat   12240
catgcatata caagtgcctt tctgtttatg ttcctgtgcc gctgttctta tgtttaatat   12300
gtaccatgat gatcaaattg tttaccaata ttggaatgaa aaggatccaa aaagagtgga   12360
```

-continued

```
atgtatatag aggattcata gagctgaccg caaataggtg tgagacatac tgatcaaatt      12420
atttgagtaa ctattcactt cttactctcg atgtatgaga agtatatgct tggtatccat      12480
ggtctatggg cttataaagt ggtttacatg ttttttggttg ggtattccac aaaatcaatg     12540
tcaatctatc taaagtattt cttgatcgat ttgatagact taactagaga agttccggaa      12600
aatatttggc aactggtgtt tggttcataa taaagctaga agatagggct gggggggggg      12660
ggtaaaattg ggggcatccg gccacgaaaa agaaatatcg acaaccaatg tcataatgtg      12720
aattctctcc tgcacttctc cttttacttg ctgagcatat acaaactgtt tcatgtctca     12780
ttggcaagtc ttctgttatc tttgaatcac cgttattgct ggaatctttg caggtcatct      12840
aatttgtcat tggaggcttt tgaatctgca gtactgtcaa agttcaaatc tctaaagcat      12900
gttcccattt ggaaagaaga aagacctcaa atactacgtg gaggggatga actaaagctc      12960
tacagagtat atcctctcgg catgacacag cgtcaggcat tgtacacctt taaattcaaa     13020
ggagacgcag atttttaggaa tcacattgaa agccacccat gcgcaaactt tgaagccata    13080
tttgtatag                                                              13089

<210> SEQ ID NO 11
<211> LENGTH: 1545
<212> TYPE: DNA
<213> ORGANISM: Nicotiana benthamiana
<220> FEATURE:
<221> NAME/KEY: CDS
<222> LOCATION: (1)..(1545)
<220> FEATURE:
<221> NAME/KEY: Variation
<222> LOCATION: (224)..(224)
<223> OTHER INFORMATION: G to A substitution in FucT009

<400> SEQUENCE: 11 atg gca aca gtt att cca att caa aga ata cca aga ttt gaa ggt gtt        48
Met Ala Thr Val Ile Pro Ile Gln Arg Ile Pro Arg Phe Glu Gly Val
1               5                   10                  15 ggg tca tta tca cct aca aac gtt ccc caa aag aaa tgg tcc aat tgg        96
Gly Ser Leu Ser Pro Thr Asn Val Pro Gln Lys Lys Trp Ser Asn Trp
            20                  25                  30 tta cct cta gta gtt gca ctt gtg gtt ata gtt gaa att gca ttt ctg       144
Leu Pro Leu Val Val Ala Leu Val Val Ile Val Glu Ile Ala Phe Leu
        35                  40                  45 ggt cga ctg gac atg gct gaa aaa gcc aac ctg gtc aac tct tgg act       192
Gly Arg Leu Asp Met Ala Glu Lys Ala Asn Leu Val Asn Ser Trp Thr
    50                  55                  60 gac tca ttt tac cag ttt acg acg tcg tct tgg tca acc tcc aac gtg       240
Asp Ser Phe Tyr Gln Phe Thr Thr Ser Ser Trp Ser Thr Ser Asn Val
65                  70                  75                  80 gaa att aat gag gct ggg ttg ggt gtg ttg agg agt agt gag gtt gat       288
Glu Ile Asn Glu Ala Gly Leu Gly Val Leu Arg Ser Ser Glu Val Asp
                85                  90                  95 cgg aat ttg gca act ggg agc tgt gag gag tgg ttg gaa aag gaa gat       336
Arg Asn Leu Ala Thr Gly Ser Cys Glu Glu Trp Leu Glu Lys Glu Asp
            100                 105                 110 tct gta gag tat tct aga gat ttt gac aaa gat cca att ttt gtt cat       384
Ser Val Glu Tyr Ser Arg Asp Phe Asp Lys Asp Pro Ile Phe Val His
        115                 120                 125 ggc ggc gaa aag gat tgg aag tct tgt gca gta gga tgt aac ttt ggt       432
Gly Gly Glu Lys Asp Trp Lys Ser Cys Ala Val Gly Cys Asn Phe Gly
    130                 135                 140 gtg gat tct gat aag aag cct gat gcg gca ttt ggg aca cca caa cag       480
Val Asp Ser Asp Lys Lys Pro Asp Ala Ala Phe Gly Thr Pro Gln Gln
```

```
Val Asp Ser Asp Lys Lys Pro Asp Ala Ala Phe Gly Thr Pro Gln Gln
145                 150                 155                 160 gct ggc acg gct agc gtg ctt cgg tca atg gag tct gct caa tac tat    528
Ala Gly Thr Ala Ser Val Leu Arg Ser Met Glu Ser Ala Gln Tyr Tyr
                165                 170                 175 ccg gag aac aac atc gtt acc gca cga cga agg gga tat gat att gta    576
Pro Glu Asn Asn Ile Val Thr Ala Arg Arg Arg Gly Tyr Asp Ile Val
            180                 185                 190 atg aca gca agc ctc tct tcg gat gtt cct gtt ggg tac ttc tct tgg    624
Met Thr Ala Ser Leu Ser Ser Asp Val Pro Val Gly Tyr Phe Ser Trp
        195                 200                 205 gcg gag tat gat ata atg gct cca gtg caa cct aaa act gag aat gca    672
Ala Glu Tyr Asp Ile Met Ala Pro Val Gln Pro Lys Thr Glu Asn Ala
    210                 215                 220 tta gca gct gct ttt att tct aat tgt ggt gct tgc aac ttc cgg ttg    720
Leu Ala Ala Ala Phe Ile Ser Asn Cys Gly Ala Cys Asn Phe Arg Leu
225                 230                 235                 240 cag gct ctt gaa gtc ctt gaa agg gca aat atc aag att gat tct ttt    768
Gln Ala Leu Glu Val Leu Glu Arg Ala Asn Ile Lys Ile Asp Ser Phe
                245                 250                 255 ggc agt tgt cat cgt aac cgg gac gga aat gtg gac aaa gtg gaa act    816
Gly Ser Cys His Arg Asn Arg Asp Gly Asn Val Asp Lys Val Glu Thr
            260                 265                 270 ctc aag tgc tac aaa ttt agc ttc gct ttt gag aat tct aat gag gag    864
Leu Lys Cys Tyr Lys Phe Ser Phe Ala Phe Glu Asn Ser Asn Glu Glu
        275                 280                 285 gat tat gtc acc gaa aaa ttc ttc cag tct tta gta gct gga tca gtc    912
Asp Tyr Val Thr Glu Lys Phe Phe Gln Ser Leu Val Ala Gly Ser Val
    290                 295                 300 ccc gtg gtg att ggt gct cca aac atc cta gac ttt gct cct tct cct    960
Pro Val Val Ile Gly Ala Pro Asn Ile Leu Asp Phe Ala Pro Ser Pro
305                 310                 315                 320 aat tca ctt tta cac att aaa gag ctg aaa gac gct gca tca gtt gcc   1008
Asn Ser Leu Leu His Ile Lys Glu Leu Lys Asp Ala Ala Ser Val Ala
                325                 330                 335 aag att atg aag tac ctt gca gaa cat cct agt gca tat aac gag tca   1056
Lys Ile Met Lys Tyr Leu Ala Glu His Pro Ser Ala Tyr Asn Glu Ser
            340                 345                 350 tta agt tgg aaa ttt gag ggt cca tct gac tcg ttc aaa gcc ctg gtt   1104
Leu Ser Trp Lys Phe Glu Gly Pro Ser Asp Ser Phe Lys Ala Leu Val
        355                 360                 365 gac atg gca gca gtt cac tct tct tgt cgt ttg tgt atc ttc tta gca   1152
Asp Met Ala Ala Val His Ser Ser Cys Arg Leu Cys Ile Phe Leu Ala
    370                 375                 380 act agt att agg gag aaa gaa gag aag agt cca aaa ttt acg aaa cgt   1200
Thr Ser Ile Arg Glu Lys Glu Glu Lys Ser Pro Lys Phe Thr Lys Arg
385                 390                 395                 400 ccc tgc aaa tgt acc aga ggt tca gaa act gtc tat cat gta tat gta   1248
Pro Cys Lys Cys Thr Arg Gly Ser Glu Thr Val Tyr His Val Tyr Val
                405                 410                 415 cgt gaa aga ggg agg ttt gac atg gag tcc gtt ttc cta agg tca tct   1296
Arg Glu Arg Gly Arg Phe Asp Met Glu Ser Val Phe Leu Arg Ser Ser
            420                 425                 430 aat ttg tca ttg gag gct ttt gaa tct gca gta ctg tca aag ttc aaa   1344
Asn Leu Ser Leu Glu Ala Phe Glu Ser Ala Val Leu Ser Lys Phe Lys
        435                 440                 445 tct cta aag cat gtt ccc att tgg aaa gaa gaa aga cct caa ata cta   1392
Ser Leu Lys His Val Pro Ile Trp Lys Glu Glu Arg Pro Gln Ile Leu
    450                 455                 460
```

-continued

```
cgt gga ggg gat gaa cta aag ctc tac aga gta tat cct ctc ggc atg    1440
Arg Gly Gly Asp Glu Leu Lys Leu Tyr Arg Val Tyr Pro Leu Gly Met
465                 470                 475                 480 aca cag cgt cag gca ttg tac acc ttt aaa ttc aaa gga gac gca gat    1488
Thr Gln Arg Gln Ala Leu Tyr Thr Phe Lys Phe Lys Gly Asp Ala Asp
                485                 490                 495 ttt agg aat cac att gaa agc cac cca tgc gca aac ttt gaa gcc ata    1536
Phe Arg Asn His Ile Glu Ser His Pro Cys Ala Asn Phe Glu Ala Ile
                500                 505                 510 ttt gta tag                                                        1545
Phe Val

<210> SEQ ID NO 12
<211> LENGTH: 514
<212> TYPE: PRT
<213> ORGANISM: Nicotiana benthamiana

<400> SEQUENCE: 12

Met Ala Thr Val Ile Pro Ile Gln Arg Ile Pro Arg Phe Glu Gly Val
1               5                   10                  15

Gly Ser Leu Ser Pro Thr Asn Val Pro Gln Lys Lys Trp Ser Asn Trp
            20                  25                  30

Leu Pro Leu Val Val Ala Leu Val Ile Val Glu Ile Ala Phe Leu
        35                  40                  45

Gly Arg Leu Asp Met Ala Glu Lys Ala Asn Leu Val Asn Ser Trp Thr
    50                  55                  60

Asp Ser Phe Tyr Gln Phe Thr Thr Ser Ser Trp Ser Thr Ser Asn Val
65                  70                  75                  80

Glu Ile Asn Glu Ala Gly Leu Gly Val Leu Arg Ser Ser Glu Val Asp
                85                  90                  95

Arg Asn Leu Ala Thr Gly Ser Cys Glu Glu Trp Leu Glu Lys Glu Asp
            100                 105                 110

Ser Val Glu Tyr Ser Arg Asp Phe Asp Lys Asp Pro Ile Phe Val His
        115                 120                 125

Gly Gly Glu Lys Asp Trp Lys Ser Cys Ala Val Gly Cys Asn Phe Gly
    130                 135                 140

Val Asp Ser Asp Lys Lys Pro Asp Ala Ala Phe Gly Thr Pro Gln Gln
145                 150                 155                 160

Ala Gly Thr Ala Ser Val Leu Arg Ser Met Glu Ser Ala Gln Tyr Tyr
                165                 170                 175

Pro Glu Asn Asn Ile Val Thr Ala Arg Arg Gly Tyr Asp Ile Val
            180                 185                 190

Met Thr Ala Ser Leu Ser Ser Asp Val Pro Val Gly Tyr Phe Ser Trp
        195                 200                 205

Ala Glu Tyr Asp Ile Met Ala Pro Val Gln Pro Lys Thr Glu Asn Ala
    210                 215                 220

Leu Ala Ala Ala Phe Ile Ser Asn Cys Gly Ala Cys Asn Phe Arg Leu
225                 230                 235                 240

Gln Ala Leu Glu Val Leu Glu Arg Ala Asn Ile Lys Ile Asp Ser Phe
                245                 250                 255

Gly Ser Cys His Arg Asn Arg Asp Gly Asn Val Asp Lys Val Glu Thr
            260                 265                 270

Leu Lys Cys Tyr Lys Phe Ser Phe Ala Phe Glu Asn Ser Asn Glu Glu
        275                 280                 285

Asp Tyr Val Thr Glu Lys Phe Phe Gln Ser Leu Val Ala Gly Ser Val
    290                 295                 300
```

```
Pro Val Val Ile Gly Ala Pro Asn Ile Leu Asp Phe Ala Pro Ser Pro
305                 310                 315                 320

Asn Ser Leu Leu His Ile Lys Glu Leu Lys Asp Ala Ala Ser Val Ala
                325                 330                 335

Lys Ile Met Lys Tyr Leu Ala Glu His Pro Ser Ala Tyr Asn Glu Ser
            340                 345                 350

Leu Ser Trp Lys Phe Glu Gly Pro Ser Asp Ser Phe Lys Ala Leu Val
        355                 360                 365

Asp Met Ala Ala Val His Ser Ser Cys Arg Leu Cys Ile Phe Leu Ala
    370                 375                 380

Thr Ser Ile Arg Glu Lys Glu Lys Ser Pro Lys Phe Thr Lys Arg
385                 390                 395                 400

Pro Cys Lys Cys Thr Arg Gly Ser Glu Thr Val Tyr His Val Tyr Val
                405                 410                 415

Arg Glu Arg Gly Arg Phe Asp Met Gly Ser Val Phe Leu Arg Ser Ser
                420                 425                 430

Asn Leu Ser Leu Glu Ala Phe Glu Ser Ala Val Leu Ser Lys Phe Lys
            435                 440                 445

Ser Leu Lys His Val Pro Ile Trp Lys Glu Arg Pro Gln Ile Leu
        450                 455                 460

Arg Gly Gly Asp Glu Leu Lys Leu Tyr Arg Val Tyr Pro Leu Gly Met
465                 470                 475                 480

Thr Gln Arg Gln Ala Leu Tyr Thr Phe Lys Phe Lys Gly Asp Ala Asp
                485                 490                 495

Phe Arg Asn His Ile Glu Ser His Pro Cys Ala Asn Phe Glu Ala Ile
            500                 505                 510

Phe Val

<210> SEQ ID NO 13
<211> LENGTH: 1536
<212> TYPE: DNA
<213> ORGANISM: Nicotiana benthamiana
<220> FEATURE:
<221> NAME/KEY: CDS
<222> LOCATION: (1)..(1536)
<220> FEATURE:
<221> NAME/KEY: Variation
<222> LOCATION: (910)..(910)
<223> OTHER INFORMATION: G to A substitution in FucT003

<400> SEQUENCE: 13 atg gaa aca gtt att cca att caa aga ata cca aga ttt gaa ggt gtt      48
Met Glu Thr Val Ile Pro Ile Gln Arg Ile Pro Arg Phe Glu Gly Val
1               5                   10                  15 ggg tca tca tcc cct aca aac gtt ccc caa aag aaa tgg tcc aat tgg      96
Gly Ser Ser Ser Pro Thr Asn Val Pro Gln Lys Lys Trp Ser Asn Trp
            20                  25                  30 tta cct cta ata gtt gca ctt gtg gtt ata gtt gaa att gca ttt ctg     144
Leu Pro Leu Ile Val Ala Leu Val Val Ile Val Glu Ile Ala Phe Leu
        35                  40                  45 ggt cga ctg gag atg gct gaa aaa gcc aac ctg gtc aac tct tgg act     192
Gly Arg Leu Glu Met Ala Glu Lys Ala Asn Leu Val Asn Ser Trp Thr
    50                  55                  60 gac tca ttt tac cag ttt acg acg tcg ttt tgg tca acc tcc aaa gtg     240
Asp Ser Phe Tyr Gln Phe Thr Thr Ser Phe Trp Ser Thr Ser Lys Val
65                  70                  75                  80 gaa att aat gag gct ggg ttg ggt gtg ttg agg agt agt gag gtt gat     288
Glu Ile Asn Glu Ala Gly Leu Gly Val Leu Arg Ser Ser Glu Val Asp
```

-continued

|  |  |  | 85 |  |  |  | 90 |  |  |  | 95 |  |  |  |  |
|---|---|---|---|---|---|---|---|---|---|---|---|---|---|---|---|
| cgg | aat | ttg | gca | act | ggg | agc | tgt | gag | gag | tgg | ttg | gaa | aag | gaa | gat | 336 |
| Arg | Asn | Leu | Ala | Thr | Gly | Ser | Cys | Glu | Glu | Trp | Leu | Glu | Lys | Glu | Asp |
|  |  |  | 100 |  |  |  | 105 |  |  |  | 110 |  |  |  |  |

```
tct gtg gag tat tct aga gat ttt gac aaa gat cca att ttt gtt cat     384
Ser Val Glu Tyr Ser Arg Asp Phe Asp Lys Asp Pro Ile Phe Val His
        115                 120                 125 ggc ggc gaa aag gat tgg aag tct tgt gca gta gga tgt aac att ggt     432
Gly Gly Glu Lys Asp Trp Lys Ser Cys Ala Val Gly Cys Asn Ile Gly
130                 135                 140 gtg gat tct gat aag aag cct gat gcg gca ttt ggg acg cca caa cag     480
Val Asp Ser Asp Lys Lys Pro Asp Ala Ala Phe Gly Thr Pro Gln Gln
145                 150                 155                 160 gct ggc acg gct agc gtg ctt cgg tca atg gag tct gct caa tac tat     528
Ala Gly Thr Ala Ser Val Leu Arg Ser Met Glu Ser Ala Gln Tyr Tyr
                165                 170                 175 ccg gag aac aac atc gtt acc gca cga cga agg gga tat gat att gta     576
Pro Glu Asn Asn Ile Val Thr Ala Arg Arg Arg Gly Tyr Asp Ile Val
            180                 185                 190 atg act aca agc ctc tct tcg gat gtt cct gtt ggg tac ttc tct tgg     624
Met Thr Thr Ser Leu Ser Ser Asp Val Pro Val Gly Tyr Phe Ser Trp
        195                 200                 205 gcg gag tat gat ata atg gct cca gtg caa cct aaa act gag aat gca     672
Ala Glu Tyr Asp Ile Met Ala Pro Val Gln Pro Lys Thr Glu Asn Ala
210                 215                 220 tta gca gct gct ttt att tct aat tgt ggt gct cgt aac ttc cgg ttg     720
Leu Ala Ala Ala Phe Ile Ser Asn Cys Gly Ala Arg Asn Phe Arg Leu
225                 230                 235                 240 caa gct ctt gaa gtc ctt gaa agg gca aat atc aag att gat tct ttt     768
Gln Ala Leu Glu Val Leu Glu Arg Ala Asn Ile Lys Ile Asp Ser Phe
                245                 250                 255 ggc agt tgt cat cgc aac cgg gac gga aat gtg gac aaa gtg gaa act     816
Gly Ser Cys His Arg Asn Arg Asp Gly Asn Val Asp Lys Val Glu Thr
            260                 265                 270 ctc aag cgc tac aaa ttt agc ttc gct ttt gag aat tcc aat gag gac     864
Leu Lys Arg Tyr Lys Phe Ser Phe Ala Phe Glu Asn Ser Asn Glu Asp
        275                 280                 285 acc gaa aaa ttc ttc cag tct tta gta gct gga tca gtc ccc gtg gtg     912
Thr Glu Lys Phe Phe Gln Ser Leu Val Ala Gly Ser Val Pro Val Val
290                 295                 300 att ggt gct cca aac atc cta gac ttt gct cct tct cct aat tca ctt     960
Ile Gly Ala Pro Asn Ile Leu Asp Phe Ala Pro Ser Pro Asn Ser Leu
305                 310                 315                 320 tta cac att aaa gag ctg aaa gac gct gca tca gtt gcc aag act atg    1008
Leu His Ile Lys Glu Leu Lys Asp Ala Ala Ser Val Ala Lys Thr Met
                325                 330                 335 aag tac ctt gca gaa aat cct agt gca tat aac gag tca tta agg tgg    1056
Lys Tyr Leu Ala Glu Asn Pro Ser Ala Tyr Asn Glu Ser Leu Arg Trp
            340                 345                 350 aaa ttt gag ggt cca tct gac tcg ttc aaa gcc ctg gtt gac atg gca    1104
Lys Phe Glu Gly Pro Ser Asp Ser Phe Lys Ala Leu Val Asp Met Ala
        355                 360                 365 gca gtt cac tct tct tgt cgt ttg tgt atc ttc tta gca act agt att    1152
Ala Val His Ser Ser Cys Arg Leu Cys Ile Phe Leu Ala Thr Ser Ile
370                 375                 380 agg gag aaa gaa gag aag agt cca aaa ttt acg aaa cgt ccc tgc aaa    1200
Arg Glu Lys Glu Glu Lys Ser Pro Lys Phe Thr Lys Arg Pro Cys Lys
385                 390                 395                 400 tgt acc aga ggt tca gaa act gtc tat cat gta tat gta cgt gaa aga    1248
```

```
Cys Thr Arg Gly Ser Glu Thr Val Tyr His Val Tyr Val Arg Glu Arg
                405                 410                 415 ggg agg ttt gac atg gag tcc att ttc cta agg tca tct aat ttg tca    1296
Gly Arg Phe Asp Met Glu Ser Ile Phe Leu Arg Ser Ser Asn Leu Ser
            420                 425                 430 ttg gag gct ttt gaa tct gca gta ctg tcg aag ttc aaa tct cta aag    1344
Leu Glu Ala Phe Glu Ser Ala Val Leu Ser Lys Phe Lys Ser Leu Lys
        435                 440                 445 cat gtt ccc att tgg aaa gaa gaa aga cct caa ata cta cgt gga ggg    1392
His Val Pro Ile Trp Lys Glu Glu Arg Pro Gln Ile Leu Arg Gly Gly
    450                 455                 460 gaa gaa cta aag ctc tac aga gta tat cct ctc ggc atg aca cag cga    1440
Glu Glu Leu Lys Leu Tyr Arg Val Tyr Pro Leu Gly Met Thr Gln Arg
465                 470                 475                 480 cag gca ttg tac acc ttt aaa ttc aaa gga gac gca gat ttt agg aat    1488
Gln Ala Leu Tyr Thr Phe Lys Phe Lys Gly Asp Ala Asp Phe Arg Asn
            485                 490                 495 cac att gaa agc cac cca tgc gca aac ttt gaa gcc ata ttt gta tag   1536
His Ile Glu Ser His Pro Cys Ala Asn Phe Glu Ala Ile Phe Val
        500                 505                 510

<210> SEQ ID NO 14
<211> LENGTH: 511
<212> TYPE: PRT
<213> ORGANISM: Nicotiana benthamiana

<400> SEQUENCE: 14

Met Glu Thr Val Ile Pro Ile Gln Arg Ile Pro Arg Phe Glu Gly Val
1               5                   10                  15

Gly Ser Ser Ser Pro Thr Asn Val Pro Gln Lys Lys Trp Ser Asn Trp
            20                  25                  30

Leu Pro Leu Ile Val Ala Leu Val Ile Val Glu Ile Ala Phe Leu
        35                  40                  45

Gly Arg Leu Glu Met Ala Glu Lys Ala Asn Leu Val Asn Ser Trp Thr
    50                  55                  60

Asp Ser Phe Tyr Gln Phe Thr Thr Ser Phe Trp Ser Thr Ser Lys Val
65                  70                  75                  80

Glu Ile Asn Glu Ala Gly Leu Gly Val Leu Arg Ser Ser Glu Val Asp
                85                  90                  95

Arg Asn Leu Ala Thr Gly Ser Cys Glu Glu Trp Leu Glu Lys Glu Asp
            100                 105                 110

Ser Val Glu Tyr Ser Arg Asp Phe Asp Lys Asp Pro Ile Phe Val His
        115                 120                 125

Gly Gly Glu Lys Asp Trp Lys Ser Cys Ala Val Gly Cys Asn Ile Gly
    130                 135                 140

Val Asp Ser Asp Lys Lys Pro Asp Ala Ala Phe Gly Thr Pro Gln Gln
145                 150                 155                 160

Ala Gly Thr Ala Ser Val Leu Arg Ser Met Glu Ser Ala Gln Tyr Tyr
                165                 170                 175

Pro Glu Asn Asn Ile Val Thr Ala Arg Arg Gly Tyr Asp Ile Val
            180                 185                 190

Met Thr Thr Ser Leu Ser Ser Asp Val Pro Val Gly Tyr Phe Ser Trp
        195                 200                 205

Ala Glu Tyr Asp Ile Met Ala Pro Val Gln Pro Lys Thr Glu Asn Ala
    210                 215                 220

Leu Ala Ala Ala Phe Ile Ser Asn Cys Gly Ala Arg Asn Phe Arg Leu
225                 230                 235                 240
```

```
Gln Ala Leu Glu Val Leu Glu Arg Ala Asn Ile Lys Ile Asp Ser Phe
            245                 250                 255
Gly Ser Cys His Arg Asn Arg Asp Gly Asn Val Asp Lys Val Glu Thr
        260                 265                 270
Leu Lys Arg Tyr Lys Phe Ser Phe Ala Phe Glu Asn Ser Asn Glu Asp
    275                 280                 285
Thr Glu Lys Phe Phe Gln Ser Leu Val Ala Gly Ser Val Pro Val Val
290                 295                 300
Ile Gly Ala Pro Asn Ile Leu Asp Phe Ala Pro Ser Pro Asn Ser Leu
305                 310                 315                 320
Leu His Ile Lys Glu Leu Lys Asp Ala Ala Ser Val Ala Lys Thr Met
            325                 330                 335
Lys Tyr Leu Ala Glu Asn Pro Ser Ala Tyr Asn Glu Ser Leu Arg Trp
        340                 345                 350
Lys Phe Glu Gly Pro Ser Asp Ser Phe Lys Ala Leu Val Asp Met Ala
    355                 360                 365
Ala Val His Ser Ser Cys Arg Leu Cys Ile Phe Leu Ala Thr Ser Ile
370                 375                 380
Arg Glu Lys Glu Lys Ser Pro Lys Phe Thr Lys Arg Pro Cys Lys
385                 390                 395                 400
Cys Thr Arg Gly Ser Glu Thr Val Tyr His Val Tyr Val Arg Glu Arg
            405                 410                 415
Gly Arg Phe Asp Met Glu Ser Ile Phe Leu Arg Ser Ser Asn Leu Ser
        420                 425                 430
Leu Glu Ala Phe Glu Ser Ala Val Leu Ser Lys Phe Lys Ser Leu Lys
    435                 440                 445
His Val Pro Ile Trp Lys Glu Glu Arg Pro Gln Ile Leu Arg Gly Gly
450                 455                 460
Glu Glu Leu Lys Leu Tyr Arg Val Tyr Pro Leu Gly Met Thr Gln Arg
465                 470                 475                 480
Gln Ala Leu Tyr Thr Phe Lys Phe Lys Gly Asp Ala Asp Phe Arg Asn
            485                 490                 495
His Ile Glu Ser His Pro Cys Ala Asn Phe Glu Ala Ile Phe Val
        500                 505                 510

<210> SEQ ID NO 15
<211> LENGTH: 20
<212> TYPE: DNA
<213> ORGANISM: Artificial
<220> FEATURE:
<223> OTHER INFORMATION: Primer VH031

<400> SEQUENCE: 15
attgtggtgc tcgcaacttc                                              20

<210> SEQ ID NO 16
<211> LENGTH: 19
<212> TYPE: DNA
<213> ORGANISM: Artificial
<220> FEATURE:
<223> OTHER INFORMATION: Primer VH032

<400> SEQUENCE: 16
acctccctct ttcacgtac                                               19

<210> SEQ ID NO 17
<211> LENGTH: 20
```

```
<212> TYPE: DNA
<213> ORGANISM: Artificial
<220> FEATURE:
<223> OTHER INFORMATION: Primer VH033

<400> SEQUENCE: 17
cttctcttgg gctgagtatg                                              20

<210> SEQ ID NO 18
<211> LENGTH: 20
<212> TYPE: DNA
<213> ORGANISM: Artificial
<220> FEATURE:
<223> OTHER INFORMATION: Primer VH034

<400> SEQUENCE: 18
ttaggagaag gcgcaaagtc                                              20

<210> SEQ ID NO 19
<211> LENGTH: 1066
<212> TYPE: DNA
<213> ORGANISM: artificial
<220> FEATURE:
<223> OTHER INFORMATION: sequence encoding FucT silencing RNA
<220> FEATURE:
<221> NAME/KEY: misc_feature
<222> LOCATION: (1)..(426)
<223> OTHER INFORMATION: part of the Nicotiana benthamiana FucT cDNA
      sequence in sense orientation
<220> FEATURE:
<221> NAME/KEY: Intron
<222> LOCATION: (427)..(644)
<223> OTHER INFORMATION: second intron of the A. thaliana XylT gene
<220> FEATURE:
<221> NAME/KEY: misc_feature
<222> LOCATION: (647)..(1066)
<223> OTHER INFORMATION: part of the Nicotiana benthamiana FucT cDNA
      sequence in antisense orientation

<400> SEQUENCE: 19
ctagaggatc cttggcagcg gctttcattt ctaattgtgg tgctcgcaac ttccgtttgc    60
aagctttaga agcccttgaa agggcaaata tcagaattga ctcttatgga agttgtcatc   120
ataacaggga tggaagagtt gacaaagtgg cagcactgaa gcgttaccag tttagcctgg   180
cttttgggaa ttctaatgag gaggactatg taactgaaaa attctttcag tctctggtag   240
ctgggtcaat ccctgtggtg gttggtgctc caaacatcca agactttgcg ccttctccta   300
attcagtttt acacattaaa gagataaaag atgctgaatc aattgccaat accatgaagt   360
accttgctca aaaccctatt gcatataatg agtcattaag gtggaagttt gagggcccat   420
ctgatggatc cactgcacgg tatgctcctc ttcttgttca tggtcatgat ccttatatga   480
gcagggaaag tccagtttag acttgtagtt agttactctt cgttatagga tttggatttc   540
ttgcgtgttt atggttttag tttccctcct ttgatgaata aaattgaatc ttgtatgagt   600
ttcatatcca tgttgtgaat ctttttgcag acgcagctag gtaccggatc catcagatgg   660
gccctcaaac ttccaccttt atgactcatt atatgcaata gggttttgag caaggtactt   720
catggtattg gcaattgatt cagcatcttt tatctcttta atgtgtaaaa ctgaattagg   780
agaaggcgca aagtcttgga tgtttggagc accaaccacc acaggattg acccagctac    840 cagagactga agaattttt cagttacata gtcctcctca ttagaattcc caaaagccag    900
gctaaactgg taacgcttca gtgctgccac tttgtcaact cttccatccc tgttatgatg   960
acaacttcca taagagtcaa ttctgatatt tgccctttca agggcttcta aagcttgcaa  1020
```
acggaagttg cgagcaccac aattagaaat gaaagccgct gccaat         1066

<210> SEQ ID NO 20
<211> LENGTH: 83
<212> TYPE: DNA
<213> ORGANISM: Artificial Sequence
<220> FEATURE:
<223> OTHER INFORMATION: Part of the Nicotiana benthamiana FucTB coding
      sequence from 1183 to 1265

<400> SEQUENCE: 20
gaaactgtct atcatgtata tgtacgtgaa agagggaggt ttgagatgga ttccattttc    60
ttaaggtcga gtgatttgtc ttt                                            83

<210> SEQ ID NO 21
<211> LENGTH: 390
<212> TYPE: DNA
<213> ORGANISM: Artificial Sequence
<220> FEATURE:
<223> OTHER INFORMATION: Sequence encoding FucT silencing RNA

<400> SEQUENCE: 21
gaaactgtct atcatgtata tgtacgtgaa agagggaggt ttgagatgga ttccattttc    60
ttaaggtcga gtgatttgtc tttgatccac tgcacggtat gctcctcttc ttgttcatgg   120
tcatgatcct tatatgagca gggaaagtcc agtttagact tgtagttagt tactcttcgt   180
tataggattt ggatttcttg cgtgtttatg gttttagttt ccctcctttg atgaataaaa   240
ttgaatcttg tatgagtttc atatccatgt tgtgaatctt tttgcagacg cagctaggta   300
ccggatcaaa gacaaatcac tcgaccttaa gaaaatggaa tccatctcaa acctccctct   360
ttcacgtaca tatacatgat agacagtttc                                    390

<210> SEQ ID NO 22
<211> LENGTH: 8
<212> TYPE: PRT
<213> ORGANISM: Artificial Sequence
<220> FEATURE:
<223> OTHER INFORMATION: Synthesized

<400> SEQUENCE: 22

Glu Glu Gln Tyr Asn Ser Thr Tyr
1               5

<210> SEQ ID NO 23
<211> LENGTH: 13
<212> TYPE: PRT
<213> ORGANISM: Artificial Sequence
<220> FEATURE:
<223> OTHER INFORMATION: Synthesized

<400> SEQUENCE: 23

Thr Lys Pro Arg Glu Glu Gln Tyr Asn Ser Thr Tyr Arg
1               5                   10